United States Patent
Andrews et al.

(10) Patent No.: US 12,065,429 B2
(45) Date of Patent: Aug. 20, 2024

(54) SMALL MOLECULE MODULATORS OF IL-17

(71) Applicant: LEO Pharma A/S, Ballerup (DK)

(72) Inventors: Mark Andrews, Ballerup (DK); Mogens Larsen, Ballerup (DK); Alan Jessiman, Ballerup (DK); Patrick Johnson, Valby (DK); Kevin Neil Dack, Ballerup (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 18/526,149

(22) Filed: Dec. 1, 2023

(65) Prior Publication Data

US 2024/0208938 A1 Jun. 27, 2024

(30) Foreign Application Priority Data

Dec. 2, 2022 (EP) .................................. 22211150
Dec. 22, 2022 (EP) .................................. 22216032
Jan. 11, 2023 (EP) .................................. 23151131

(51) Int. Cl.
*C07D 401/14* (2006.01)

(52) U.S. Cl.
CPC ................................. *C07D 401/14* (2013.01)

(58) Field of Classification Search
CPC .................................................. C07D 401/14
See application file for complete search history.

(56) References Cited

U.S. PATENT DOCUMENTS

| | | | |
|---|---|---|---|
| 2022/0235038 A1 | 7/2022 | Fathere et al. | |
| 2023/0159465 A1 | 5/2023 | Li et al. | |
| 2023/0227437 A1 | 7/2023 | Li et al. | |

FOREIGN PATENT DOCUMENTS

| | | |
|---|---|---|
| CN | 112341429 A | 2/2021 |
| CN | 112341435 A | 2/2021 |
| CN | 112341439 A | 2/2021 |
| CN | 112341440 A | 2/2021 |
| CN | 112341441 A | 2/2021 |
| CN | 112341442 A | 2/2021 |
| CN | 112341446 A | 2/2021 |
| CN | 112341450 A | 2/2021 |
| CN | 112341451 A | 2/2021 |
| CN | 112341519 A | 2/2021 |
| CN | 112824399 A | 5/2021 |
| CN | 113683598 A | 11/2021 |
| CN | 113880766 A | 1/2022 |
| CN | 113880767 A | 1/2022 |
| CN | 113943278 A | 1/2022 |
| CN | 113999234 A | 2/2022 |
| CN | 116143777 A | 5/2023 |
| EP | 3 943 495 A1 | 1/2022 |
| WO | WO 2013/116682 A1 | 8/2013 |
| WO | WO 2014/066726 A2 | 5/2014 |
| WO | WO 2018/229079 A1 | 12/2018 |
| WO | WO 2019/138017 A1 | 7/2019 |
| WO | WO 2019/223718 A1 | 11/2019 |
| WO | WO 2020/011731 A1 | 1/2020 |
| WO | WO 2020/120140 A1 | 6/2020 |
| WO | WO 2020/120141 A1 | 6/2020 |
| WO | WO 2020/127685 A1 | 6/2020 |
| WO | WO 2020/146194 A1 | 7/2020 |
| WO | WO 2020/163554 A1 | 8/2020 |
| WO | WO 2020/182666 A1 | 9/2020 |
| WO | WO 2020/260425 A1 | 12/2020 |
| WO | WO 2020/260426 A1 | 12/2020 |
| WO | WO 2020/261141 A1 | 12/2020 |
| WO | WO 2021/055376 A1 | 3/2021 |
| WO | WO 2021/098844 A1 | 5/2021 |
| WO | WO 2021/170627 A1 | 9/2021 |
| WO | WO 2021/170631 A1 | 9/2021 |
| WO | WO 2021/204800 A1 | 10/2021 |
| WO | WO 2021/204801 A1 | 10/2021 |
| WO | WO 2021/220183 A1 | 11/2021 |

(Continued)

OTHER PUBLICATIONS

Mikkola, BMC Cancer, (2022), 22:54, 1 of 14-14 or 14, https;//doi.org/10.1186/s12885-021-08969-0. (Year: 2022).*
Khan, Frontiers in Genetics, Jul. 2015, vol. 6(236), 1-9. (Year: 2015).*
Liu, Frontiers in Immuology, Nov. 2020, vol. 11, article 594735, 1-13, doi: 10.3389/fimmu.2020.594735. (Year: 2020).*
International Search Report for International Application No. PCT/EP2023/083742, dated Feb. 9, 2024 (3 pgs.).
Written Opinion of the International Searching Authority for International Application No. PCT/EP2023/083742 (6 pgs.).
Amatya, N. et al., (2017) 'IL-17 signaling: The Yin and the Yang', Trends in Immunology, 38(5), pp. 310-322.
Gaffen, S.L. et al. (2014) 'The IL-23-il-17 immune axis: From mechanisms to therapeutic testing', Nature Reviews Immunology, 14(9), pp. 585-600.

(Continued)

*Primary Examiner* — D Margaret M Seaman
(74) *Attorney, Agent, or Firm* — FINNEGAN, HENDERSON, FARABOW, GARRETT & DUNNER, LLP

(57) ABSTRACT

The present invention relates to a compound according to formula (I)

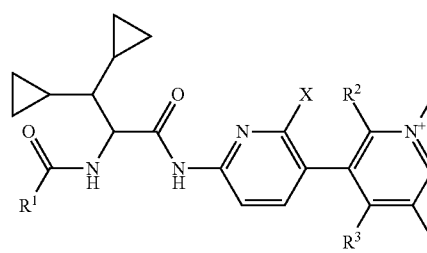

and pharmaceutically acceptable salts, hydrates, or solvates thereof. The invention further relates to said compounds for use in therapy, to pharmaceutical compositions comprising said compounds, to methods of treating diseases, e.g., dermal diseases, with said compounds, and to the use of said compounds in the manufacture of medicaments.

20 Claims, No Drawings

(56) References Cited

FOREIGN PATENT DOCUMENTS

| WO | WO 2021/222404 A1 | 11/2021 |
| WO | WO 2021/239743 A1 | 12/2021 |
| WO | WO 2021/239745 A1 | 12/2021 |
| WO | WO 2021/250194 A1 | 12/2021 |
| WO | WO 2021/255085 A1 | 12/2021 |
| WO | WO 2021/255086 A1 | 12/2021 |
| WO | WO 2021/255174 A1 | 12/2021 |
| WO | WO 2022/091056 A1 | 5/2022 |
| WO | WO 2022/096411 A1 | 5/2022 |
| WO | WO 2022/096412 A1 | 5/2022 |
| WO | WO 2022/128584 A1 | 6/2022 |
| WO | WO 2023/275301 A1 | 1/2023 |
| WO | WO 2023/283453 A1 | 1/2023 |
| WO | WO 2023/025783 A1 | 3/2023 |
| WO | WO 2023/049885 A1 | 3/2023 |
| WO | WO 2023/049886 A1 | 3/2023 |
| WO | WO 2023/049887 A1 | 3/2023 |
| WO | WO 2023/049888 A1 | 3/2023 |
| WO | WO 2023/078319 A1 | 5/2023 |
| WO | WO 2023/111181 A1 | 6/2023 |

OTHER PUBLICATIONS

Goedken, E.R. et al. (2022) Identification and structure-based drug design of cell-active inhibitors of interleukin 17A at a novel C-terminal site. Sci Rep 12, 14561.

Leslie Dakin, 12th Swiss Course on Medicinal Chemistry, Leysin, Oct. 9-14, 2016.

Liu, S. et al. (2016) Binding site elucidation and structure guided design of macrocyclic IL-17A antagonists. Sci. Rep. 6, 30859.

Monin, L. et al., (2017) 'Interleukin 17 family cytokines: Signaling mechanisms, biological activities, and therapeutic implications', Cold Spring Harbor Perspectives in Biology, 10(4).

Onishi, R.M. et al., (2010) 'Interleukin-17 and its target genes: Mechanisms of interleukin-17 function in disease', Immunology, 129(3), pp. 311-321.

* cited by examiner

SMALL MOLECULE MODULATORS OF IL-17

PRIORITY

This application claims priority to European Patent Application No. 22211150.2, filed Dec. 2, 2022, European Patent Application No. 22216032.7, filed Dec. 22, 2022, and European Patent Application No. 23151131.2, filed Jan. 11, 2023, the entire contents of each of which are incorporated herein by reference.

FIELD OF THE INVENTION

This invention relates to novel amino-acid amides and derivatives thereof, to said compounds for use in therapy and to pharmaceutical compositions comprising said compounds.

BACKGROUND OF THE INVENTION

IL-17 (also known as IL-17A or CTLA8) is a pro-inflammatory cytokine involved in anti-microbial defense at epithelial surfaces. IL-17 is comprised of two covalently joined IL-17A subunits (IL-17AA) with an approximate mass of 32 kDa, and signals through a receptor comprising IL17RA and IL17RC subunits. This receptor is predominantly expressed in epithelial and mesenchymal cells. The IL17RA/IL17RC receptor is also used by IL-17 variants IL-17AF and IL-17FF, which both are successively weaker, partial agonists on this receptor (Monin, L., Gaffen, S. L.; 2018, Cold Spring Harb. Perspect. Biol. 10. doi: 10.1101/cshperspect.a028522). Crucial for signaling is the assembly of signaling complexes containing the multifunctional protein ACT1/CIKS, which in turn can recruit TRAF and other proteins.

Via these signaling complexes IL-17 induces cytokines, chemokines, antimicrobial peptides and growth factors via activation of transcription factor NFkB or via MAP kinase-dependent pathways (e.g., IL-6, IL-8, CXCL1, CXCL2, CXCL5, CCL20, G-CSF, BD4) and stabilizes the mRNAs of certain inflammatory cytokines, such as CXCL1. This leads to amplification of their effects. Further, IL-17 acts in concert with IL-1beta, IL-22 and IFNgamma (Amatya, N. et al., Trends in Immunology, 2017, 38, 310-322. doi: 10.1016/j.it.2017.01.006; Onishi, R. M., Gaffen, S. L. Immunology, 2010, 129, 311-321. doi: 10.1111/j.1365-2567.2009.03240.x).

IL-17 is secreted by a variety of immune cells, such as Th17 helper cells, Tc17 cytotoxic cells, ILC3 innate cells, NKT cells, TCRbeta+ natural T cells, and gamma-deltaT-cells (Monin, L., Gaffen, S. L.; 2018, Cold Spring Harb. Perspect. Biol. 10. doi: 10.1101/cshperspect.a028522). Increased, disease-provoking levels of IL-17 are observed in several autoimmune diseases, such as psoriasis, ankylosing spondylitis, spondyloarthritis, and psoriatic arthritis. Other diseases where deregulation of IL-17 is observed are rheumatoid arthritis, systemic lupus erythematosus, asthma, inflammatory bowel disease, autoimmune uveitis, multiple sclerosis, and certain cancers (Gaffen, S. L. et al., Nat Rev Immunol., 2014, 14, 585-600. doi: 10.1038/nri3707; Monin, L., Gaffen, S. L.; 2018, Cold Spring Harb. Perspect. Biol. 10. doi: 10.1101/cshperspect.a028522). Hence, IL-17 is a significant therapeutic target.

Therapeutic, neutralizing antibodies against IL-17A (Secukinumab, Ixekizumab) or receptor IL17RA (Brodalumab) have shown high efficacy in the treatment of psoriasis, ankylosing spondylitis, and psoriatic arthritis. These antibodies have long half-lives in the body.

Although various antibodies against IL-17A or IL-17RA are approved, there are currently no approved, orally available modulators of IL-17.

The following patent applications describe small molecule modulators: WO2013116682, WO2014066726, WO2018229079, WO2019223718, WO2019138017, WO2020011731, WO2020120140, WO2020120141, WO2020127685, WO2020146194, WO2020163554, WO2020182666. WO2020260426, WO2020260425, WO2020261141, WO2021055376, WO2021098844, WO2021204800A, WO2021204801A, WO2021170627, WO2021170631, WO2021220183, WO2021222404, WO2021239743, WO2021239745, WO2021250194, WO2021255174, WO2021255085, WO2021255086, WO2022091056, WO2022096411, WO2022096412, WO2022128584, WO2023025783, WO2023049885, WO2023049886, WO2023049887, WO2023049888, WO2023078319, WO2023111181, WO2023275301, WO2023283453, US20220235038, EP3943495, CN112824399A, CN112341429A, CN112341435A, CN112341439A, CN112341440A, CN112341441A, CN112341442A, CN112341446A, CN112341450A, CN112341451A, CN112341519A, CN113683598A, CN113880767A, CN113880766A, CN113999234A, CN113943278, and CN116143777A all disclose Compounds for Modulating IL-17.

Scientific Reports (2016) 6, 30859 discloses Macrocyclic IL-17A Antagonists, Scientific Reports (2022) 12, 14561 discloses Identification and structure-based drug design of cell-active inhibitors of interleukin 17A at a novel C-terminal site and Leslie Dakin, 12$^{th}$ Swiss Course on Medicinal Chemistry, Leysin, Oct. 9-14, 2016 discloses 'Hit Identification, binding site elucidation and structure guided design of novel macrocyclic IL-17A antagonists'.

Orally available, highly efficacious small molecule IL-17 modulators which bind to IL-17 to decrease its functional ability to activate the IL-17 receptor complex may have a number of advantages compared to monoclonal antibodies. Oral administration and flexible treatment regimen may be two significant aspects in favor of patient convenience and the compounds may exhibit improved safety due to the possibility of faster withdrawal of the drug should adverse events occur.

Therefore, there is a continuous need to develop small molecule modulators of IL-17, particularly small molecules suitable for oral administration.

In addition, some patients may be treated by topical application of small molecule modulators of IL-17. This can be particularly suitable for patients with skin lesions that are readily accessible and limited in body surface area. Topical treatment may also be prescribed for certain patients who could benefit from avoiding systemic modulation of the IL-17 pathway, for example when undergoing treatment for infections or gastrointestinal problems.

SUMMARY OF THE INVENTION

The inventors have surprisingly found that novel compounds of the present invention exhibit modulating effects on the IL-17 signalling pathway.

Compounds of the present invention have advantageous properties such as high metabolic stability, membrane permeability, and/or solubility that make them particularly suitable for oral administration.

Compounds of the present invention may be beneficial in preventing, treating or ameliorating a variety of diseases which involve up-regulation or de-regulation of IL-17, such as for example psoriasis, ankylosing spondylitis, hidradenitis suppurativa, and psoriatic arthritis.

Accordingly, the present invention relates to a compound according to formula (I)

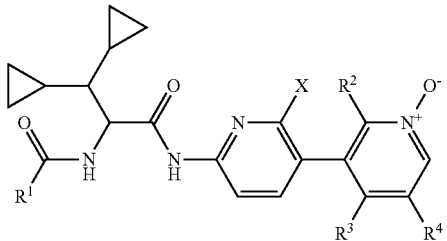

wherein X is fluoro or chloro;
R¹ is selected from

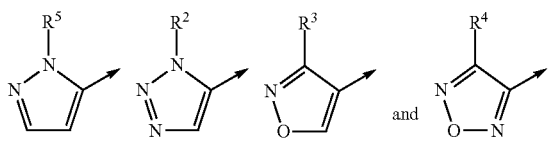

wherein R⁵ is independently selected from (C₁-C₄)alkyl, (C₃-C₄)cycloalkyl, and —CH₂—(C₃-C₄)cycloalkyl, wherein said (C₁-C₄)alkyl, (C₃-C₄)cycloalkyl, and —CH₂—(C₃-C₄)cycloalkyl may optionally be substituted with substituents independently selected from one hydroxy group and 1, 2 or 3 fluoro;

R² is selected from hydrogen, (C₁-C₃)alkyl, cyclopropyl and chloro, wherein said (C₁-C₃)alkyl may optionally be substituted with one or more fluoro;

R³ is selected from hydrogen, (C₁-C₃)alkyl, cyclopropyl, and chloro, wherein said (C₁-C₃)alkyl may optionally be substituted with one or more fluoro; and R⁴ is selected from hydrogen, (C₁-C₃)alkyl, cyclopropyl, (C₁-C₂)alkoxy, cyano, methylsulfone, fluoro, and chloro; wherein said (C₁-C₃)alkyl, and (C₁-C₂)alkoxy may optionally be substituted with one or more fluoro; provided that at least one of R² and R³ is different from hydrogen;

or pharmaceutically acceptable salts thereof.

The invention in one embodiment relates to a compound having the formula (II)

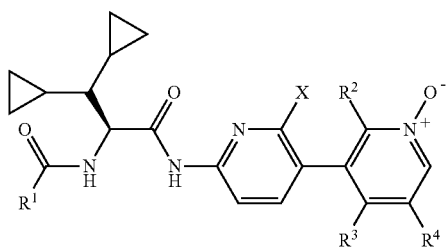

wherein X, R¹, R², R³, R⁴, and R⁵ are as defined as above; or pharmaceutically acceptable salts thereof.

As indicated in the formula (I) and (II) the compounds of the invention are N-oxides.

DETAILED DESCRIPTION OF THE INVENTION

Definitions

Whenever the compound of formula (I) is mentioned herein it should be understood that the compound of formula (II) is a subgroup of the compound of formula (I).

The term "(C$_a$-C$_b$)alkyl" is intended to indicate a hydrocarbon radical obtained when one hydrogen atom is removed from a branched or linear hydrocarbon. Said alkyl comprises (a-b) carbon atoms, such as 1-6, such as 1-4, such as 1-3, such as 2-3 or such as 1-2 carbon atoms. The term includes the subclasses normal alkyl (n-alkyl), secondary, and tertiary alkyl, such as methyl, ethyl, n-propyl, isopropyl, n-butyl, isobutyl, sec.-butyl, and tert.-butyl. n-

The term "(C$_a$-C$_b$)alkoxy" is intended to indicate a radical of the formula —OR', wherein R' is (C$_a$-C$_b$)alkyl as indicated herein, wherein the (C$_a$-C$_b$)alkyl group is appended to the parent molecular moiety through an oxygen atom, e.g., methoxy (—OCH₃), and ethoxy (—OCH₂CH₃).

The term "cyano" is intended to indicate a —CN group attached to the parent molecular moiety through the carbon atom.

The term "(C$_a$-C$_b$)cycloalkyl" is intended to indicate a saturated (C$_a$-C$_b$)cycloalkane hydrocarbon radical, comprising a-b carbon atoms, such h as 3-4 carbon atoms, e.g., cyclopropyl, or cyclobutyl.

If substituents are described as being independently selected from a group, each substituent is selected independent of the other. Each substituent may therefore be identical or different from the other substituent(s).

The term "optionally substituted" means "unsubstituted or substituted", and therefore the general formulas described herein encompasses compounds containing the specified optional substituent(s) as well as compounds that do not contain the optional substituent(s).

As used herein whenever a molecular drawing of a substituent contains an arrow—the arrow indicates the bond attaching the substituent to the rest of the molecule.

The term "pharmaceutically acceptable salt" is intended to indicate salts prepared by reacting a compound of formula (I), which comprise a basic moiety, with a suitable inorganic or organic acid, such as hydrochloric, hydrobromic, hydroiodic, sulfuric, nitric, phosphoric, formic, acetic, 2,2-dichloroacetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxyethanesulfonic acid, toluenesulfonic, sulfamic or fumaric acid.

Pharmaceutically acceptable salts of compounds of formula (I) comprising an acidic moiety may also be prepared by reaction with a suitable base such as sodium hydroxide, potassium hydroxide, magnesium hydroxide, calcium hydroxide, zinc hydroxide, barium hydroxide, ammonia or the like, or suitable non-toxic amines, such as lower alkylamines (such as diethylamine, tetraalkylammonium hydroxide), hydroxy-lower alkylamines (such as diethanolamine, 2-(diethylamino)-ethanol, ethanolamine, triethanolamine, tromethamine, deanol), cycloalkylamines, ethylene diamine, or benzylamines, (such as benethamine and benzathine), betaine, choline hydroxide, N-methyl-glucamine, hydrabamine, 1H-imidazole, 4-(2-hydroxyethyl)- morpholine, piperazine, 1-(2-hydroxyethyl)-pyrrolidine, L-arginine or L-lysine. Further examples of pharmaceutical acceptable salts are listed in Berge, S. M.; J. Pharm. Sci.; (1977), 66(1), 1-19, and in Stahl, P. H. and Wermuth, C. G, Handbook of Pharmaceutical Salts, Properties, Selection and Use, $2^{nd}$ Edition, Wiley-VCH, 2011 both of which are incorporated herein by reference.

The term "solvate" is intended to indicate a species formed by interaction between a compound, e.g., a compound of formula (I) or a pharmaceutically acceptable salt thereof, and a solvent, e.g., alcohol, glycerol or water, wherein said species are in a crystalline form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

In one embodiment the invention relates to a compound of formula (I) or (II) wherein $R^1$ is

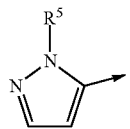

In one embodiment the invention relates to a compound of formula (I) or (II) as above wherein $R^5$ is independently selected from $(C_1-C_4)$alkyl, $(C_3-C_4)$cycloalkyl, and —$CH_2$—$(C_3-C_4)$cycloalkyl, wherein said $(C_1-C_4)$alkyl, $(C_3-C_4)$cycloalkyl, and —$CH_2$—$(C_3-C_4)$cycloalkyl may optionally be substituted with substituents independently selected from 1, 2 or 3 fluoro.

In one embodiment the invention relates to a compound of formula (I) or (II) as above wherein $R^5$ is $(C_1-C_4)$alkyl, wherein said $(C_1-C_4)$alkyl, may optionally be substituted with substituents independently selected from 1, 2 or 3 fluoro.

In one embodiment the invention relates to a compound of formula (I) or (II) as above wherein $R^5$ is $(C_1-C_4)$alkyl.

In one embodiment the invention relates to a compound as above wherein $R^5$ is propan-2-yl.

In one embodiment the invention relates to a compound as above wherein
$R^2$ is selected from hydrogen and methyl.

In one embodiment the invention relates to a compound as above wherein
$R^2$ is selected from hydrogen and methyl;
$R^3$ is selected from hydrogen, methyl, and trifluoromethyl; and
$R^4$ is selected from hydrogen, methyl, cyclopropyl, $(C_1-C_2)$alkoxy, fluoro, and chloro;
wherein said methyl and $(C_1-C_2)$alkoxy may optionally be substituted with one or more fluoro.

In one embodiment the invention relates to a compound as above wherein $R^2$ is methyl.

In one embodiment the invention relates to a compound as above wherein X is chloro.

In one embodiment the invention relates to a compound as above wherein X is fluoro.

In a further embodiment the invention relates to a compound as above wherein the compound is selected from:

N-[(1S)-1-(dicyclopropylmethyl)-2-[[6-fluoro-5-(5-methoxy-2-methyl-1-oxido-pyridin-1-ium-3-yl)-2-pyridyl]amino]-2-oxo-ethyl]-2-isopropyl-pyrazole-3-carboxamide;

N-[(1S)-1-(dicyclopropylmethyl)-2-[[6-fluoro-5-(5-fluoro-2-methyl-1-oxido-pyridin-1-ium-3-yl)-2-pyridyl]amino]-2-oxo-ethyl]-2-isopropyl-pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-isopropyl-pyrazole-3-carboxamide;

N-[(1S)-1-(dicyclopropylmethyl)-2-[[5-(2,4-dimethyl-1-oxido-pyridin-1-ium-3-yl)-6-fluoro-2-pyridyl]amino]-2-oxo-ethyl]-2-isopropyl-pyrazole-3-carboxamide;

N-[(1S)-1-(dicyclopropylmethyl)-2-[[5-(2-ethyl-1-oxido-pyridin-1-ium-3-yl)-6-fluoro-2-pyridyl]amino]-2-oxo-ethyl]-2-isopropyl-pyrazole-3-carboxamide;

N-[(1S)-1-(dicyclopropylmethyl)-2-[[6-fluoro-5-[1-oxido-4-(trifluoromethyl)pyridin-1-ium-3-yl]-2-pyridyl]amino]-2-oxo-ethyl]-2-isopropyl-pyrazole-3-carboxamide;

N-[(1S)-2,2-dicyclopropyl-1-[[5-(2-cyclopropyl-1-oxido-pyridin-1-ium-3-yl)-6-fluoro-2-pyridyl]carbamoyl]ethyl]-2-isopropyl-pyrazole-3-carboxamide;

N-[(1S)-1-(dicyclopropylmethyl)-2-[[5-[5-(difluoromethoxy)-2-methyl-1-oxido-pyridin-1-ium-3-yl]-6-fluoro-2-pyridyl]amino]-2-oxo-ethyl]-2-isopropyl-pyrazole-3-carboxamide;

N-[(1S)-1-(dicyclopropylmethyl)-2-[[6-fluoro-5-[5-(fluoromethoxy)-2-methyl-1-oxido-pyridin-1-ium-3-yl]-2-pyridyl]amino]-2-oxo-ethyl]-2-isopropyl-pyrazole-3-carboxamide;

N-[(1S)-1-(dicyclopropylmethyl)-2-[[5-(5-ethoxy-2-methyl-1-oxido-pyridin-1-ium-3-yl)-6-fluoro-2-pyridyl]amino]-2-oxo-ethyl]-2-isopropyl-pyrazole-3-carboxamide;

N-[(1S)-1-[[5-(5-chloro-2-methyl-1-oxido-pyridin-1-ium-3-yl)-6-fluoro-2-pyridyl]carbamoyl]-2,2-dicyclopropyl-ethyl]-2-isopropyl-pyrazole-3-carboxamide;

N-[(1S)-1-(dicyclopropylmethyl)-2-[[6-fluoro-5-[2-methyl-1-oxido-5-(trifluoromethyl)pyridin-1-ium-3-yl]-2-pyridyl]amino]-2-oxo-ethyl]-2-isopropyl-pyrazole-3-carboxamide;

N-[(1S)-2,2-dicyclopropyl-1-[[5-(2-cyclopropyl-5-methyl-1-oxido-pyridin-1-ium-3-yl)-6-fluoro-2-pyridyl]carbamoyl]ethyl]-2-isopropyl-pyrazole-3-carboxamide;

N-[(1S)-2,2-dicyclopropyl-1-[[5-(5-cyclopropyl-2-methyl-1-oxido-pyridin-1-ium-3-yl)-6-fluoro-2-pyridyl]carbamoyl]ethyl]-2-isopropyl-pyrazole-3-carboxamide;

N-[(1S)-1-(dicyclopropylmethyl)-2-[[6-fluoro-5-(4-methyl-1-oxido-pyridin-1-ium-3-yl)-2-pyridyl]amino]-2-oxo-ethyl]-2-isopropyl-pyrazole-3-carboxamide;

N-[(1S)-1-(dicyclopropylmethyl)-2-[[6-fluoro-5-(2-methyl-1-oxido-pyridin-1-ium-3-yl)-2-pyridyl]amino]-2-oxo-ethyl]-2-isopropyl-pyrazole-3-carboxamide;

N-[(1S)-1-[[6-chloro-5-(2,5-dimethyl-1-oxido-pyridin-1-ium-3-yl)-2-pyridyl]carbamoyl]-2,2-dicyclopropyl-ethyl]-2-isopropyl-pyrazole-3-carboxamide;

N-[(1S)-1-[[6-chloro-5-(5-fluoro-2-methyl-1-oxido-pyridin-1-ium-3-yl)-2-pyridyl]carbamoyl]-2,2-dicyclopropyl-ethyl]-2-isopropyl-pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-propyl-pyrazole-3-carboxamide;

2-tert-butyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-isopropyl-isoxazole-4-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-isopropyl-triazole-4-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(2,2-difluoroethyl)pyrazole-3-carboxamide;

2-cyclobutyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(difluoromethyl)pyrazole-3-carboxamide;

2-cyclopropyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-isobutyl-pyrazole-3-carboxamide;

2-(cyclopropylmethyl)-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(3-hydroxybutyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(4,4,4-trifluoro-3-hydroxy-butyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[(3,3-difluorocyclobutyl)methyl]pyrazole-3-carboxamide;

4-cyclopropyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-1,2,5-oxadiazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(3-hydroxypropyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[(1S*)-2,2-difluoro-1-methyl-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[(1S*)-2,2-difluoro-1-methyl-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[2-fluoro-1-(fluoromethyl)ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-methyl-isoxazole-4-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-ethyl-isoxazole-4-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-4-methyl-1,2,5-oxadiazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-ethyl-pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-methyl-pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(2,2,2-trifluoroethyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-sec-butyl-pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(2,2-difluoropropyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[(1S)-2-hydroxy-1-methyl-ethyl]pyrazole-3-carboxamide N-[(1S)-2,2-dicyclopropyl-1-[[5-(4-cyclopropyl-1-oxido-pyridin-1-ium-3-yl)-6-fluoro-2-pyridyl]carbamoyl]ethyl]-2-isopropyl-pyrazole-3-carboxamide;

N-[(1S)-1-(dicyclopropylmethyl)-2-[[5-[5-(difluoromethyl)-4-methyl-1-oxido-pyridin-1-ium-3-yl]-6-fluoro-2-pyridyl]amino]-2-oxo-ethyl]-2-isopropyl-pyrazole-3-carboxamide;

N-[(1S)-1-(dicyclopropylmethyl)-2-[[5-[5-(difluoromethyl)-2-methyl-1-oxido-pyridin-1-ium-3-yl]-6-fluoro-2-pyridyl]amino]-2-oxo-ethyl]-2-isopropyl-pyrazole-3-carboxamide;

N-[(1S)-1-(dicyclopropylmethyl)-2-[[6-fluoro-5-[5-fluoro-1-oxido-4-(trifluoromethyl)pyridin-1-ium-3-yl]-2-pyridyl]amino]-2-oxo-ethyl]-2-isopropyl-pyrazole-3-carboxamide;

N-[(1S)-1-(dicyclopropylmethyl)-2-[[5-[4-(difluoromethyl)-1-oxido-pyridin-1-ium-3-yl]-6-fluoro-2-pyridyl]amino]-2-oxo-ethyl]-2-isopropyl-pyrazole-3-carboxamide;

N-[(1S)-1-(dicyclopropylmethyl)-2-[[5-(4,5-dimethyl-1-oxido-pyridin-1-ium-3-yl)-6-fluoro-2-pyridyl]amino]-2-oxo-ethyl]-2-isopropyl-pyrazole-3-carboxamide;

N-[(1S)-1-(dicyclopropylmethyl)-2-[[5-(4-ethyl-1-oxido-pyridin-1-ium-3-yl)-6-fluoro-2-pyridyl]amino]-2-oxo-ethyl]-2-isopropyl-pyrazole-3-carboxamide;

Atropisomer 1 of N-[(1S)-1-(dicyclopropylmethyl)-2-[[6-fluoro-5-[2-methyl-1-oxido-4-(trifluoromethyl)pyridin-1-ium-3-yl]-2-pyridyl]amino]-2-oxo-ethyl]-2-isopropyl-pyrazole-3-carboxamide;

Atropisomer 2 of N-[(1S)-1-(dicyclopropylmethyl)-2-[[6-fluoro-5-[2-methyl-1-oxido-4-(trifluoromethyl)pyridin-1-ium-3-yl]-2-pyridyl]amino]-2-oxo-ethyl]-2-isopropyl-pyrazole-3-carboxamide;

Atropisomer 1 of N-[(1S)-1-[[6-chloro-5-(2,4-dimethyl-1-oxido-pyridin-1-ium-3-yl)-2-pyridyl]carbamoyl]-2,2-dicyclopropyl-ethyl]-2-isopropyl-pyrazole-3-carboxamide;

Atropisomer 2 of N-[(1S)-1-[[6-chloro-5-(2,4-dimethyl-1-oxido-pyridin-1-ium-3-yl)-2-pyridyl]carbamoyl]-2,2-dicyclopropyl-ethyl]-2-isopropyl-pyrazole-3-carboxamide;

N-[(1S)-1-(dicyclopropylmethyl)-2-[[6-fluoro-5-(2-methyl-5-methylsulfonyl-1-oxido-pyridin-1-ium-3-yl)-2-pyridyl]amino]-2-oxo-ethyl]-2-isopropyl-pyrazole-3-carboxamide;

N-[(1S)-1-[[5-(5-cyano-2-methyl-1-oxido-pyridin-1-ium-3-yl)-6-fluoro-2-pyridyl]carbamoyl]-2,2-dicyclopropyl-ethyl]-2-isopropyl-pyrazole-3-carboxamide; and N-[(1S)-1-(dicyclopropylmethyl)-2-[[6-fluoro-5-(5-methoxy-2-ethyl-1-oxido-pyridin-1-ium-3-yl)-2-pyridyl]amino]-2-oxo-ethyl]-2-isopropyl-pyrazole-3-carboxamide;

or pharmaceutically acceptable salts thereof.

In one or more embodiments of the present invention, the compounds of general formula (I) have an ($EC_{50}$) value in a HEK Blue™ IL-17 assay of less than 1 micromolar, or of less than 100 nanomolar.

The compounds of formula (I) may be obtained in crystalline form either directly by concentration from an organic solvent or by crystallisation or recrystallisation from an organic solvent or mixture of said solvent and a co-solvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

Compounds of formula (I) comprise asymmetrically substituted (chiral) carbon atoms which give rise to the existence of isomeric forms, e.g., enantiomers and possibly diastereomers. The present invention relates to all such isomers, either in optically pure form or as mixtures thereof (e.g., racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g., high pressure liquid chromatography using chiral stationary phases. Enantiomers may be separated from each other by selective crystallization of their diasteromeric salts which may be formed with optically active amines, or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials. Furthermore, when a double bond or a fully or partially saturated ring system is present in the molecule geometric isomers may be formed. Any geometric isomer, as separated, pure or partially purified geometric isomers or mixtures thereof are included within the scope of the invention.

In the compounds of general formula (I), the atoms may exhibit their natural isotopic abundances, or one or more of the atoms may be artificially enriched in a particular isotope having the same atomic number, but an atomic mass or mass number different from the atomic mass or mass number found in nature. The present invention includes all suitable isotopic variations of the compounds of general formula (I). For example, different isotopic forms of hydrogen include $^1H$, $^2H$, and $^3H$, different isotopic forms of carbon include $^{12}C$, $^{13}C$, and $^{14}C$ and different isotopic forms of nitrogen include $^{14}N$ and $^{15}N$. Enriching for deuterium ($^2H$) may for example increase in-vivo half-life or reduce dosage regimens, or may provide a compound useful as a standard for characterization of biological samples. Isotopically enriched compounds within general formula (I) can be prepared by conventional techniques well known to a person skilled in the art or by processes analogous to those described in the general procedures and examples herein using appropriate isotopically enriched reagents and/or intermediates.

Solvates and hydrates form part of the invention claimed.

WO2023275301 discloses that Il 17 modulators may be useful in the treatment and/or prophylaxis of a pathological disorder that is mediated by a pro-inflammatory IL-17 cytokine or is associated with an increased level of a pro-inflammatory IL-17 cytokine. Generally, the pathological condition may be selected from the group consisting of infections (viral, bacterial, fungal, and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury, pelvic inflammatory disease, Alzheimer's Disease, Crohn's disease, inflammatory bowel disease, irritable bowel syndrome, ulcerative colitis, Castleman's disease, axial spondyloarthritis, ankylosing spondylitis, and other spondyloarthropathies, dermatomyositis, myocarditis, uveitis, exophthalmos, autoimmune thyroiditis, Peyronie's Disease, coeliac disease, gall bladder disease, Pilonidal disease, peritonitis, psoriasis, atopic dermatitis, hidradenitis suppurativa, vasculitis, surgical adhesions, stroke, autoimmune diabetes, Type I Diabetes, lyme arthritis, meningoencephalitis, immune mediated inflammatory disorders of the central, and peripheral nervous system such as multiple sclerosis, and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers, and hematologic malignancies, and in particular acute myelogenous leukaemia, chronic myelogenous leukemia, chronic lymphatic leukemia, gastric cancer, and colon cancer), heart disease including ischaemic diseases such as myocardial infarction as well as atherosclerosis, intravascular coagulation, bone resorption, osteoporosis, periodontitis, hypochlorhydia, and pain (particularly pain associated with inflammation).

WO2022091056 discloses that IL 17 modulators may be used in the treatment, or prevention of autoimmune diseases and of inflammatory conditions, in particular inflammatory conditions with an etiology including an autoimmune component such as arthritis (for example rheumatoid arthritis, arthritis chronica progrediente, and arthritis deformans) and rheumatic diseases, including inflammatory conditions, and rheumatic diseases involving bone loss, inflammatory pain, spondyloarthropathies including ankylosing spondylitis, and non-radiographic axial spondyloarthritis, Reiter syndrome, reactive arthritis, psoriatic arthritis, and enterophathis arthritis, osteoarthritis, tendinopathy, hypersensitivity (including both airways hypersensitivity, and dermal hypersensitivity) and allergies, including eczema, and dermatitis, as well as asthma; in particular autoimmune diseases such as autoimmune hematological disorders (including e.g., hemolytic anemia, aplastic anemia, pure red cell anemia, and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven Johnson syndrome, idiopathic sprue, autoimmune inflammatory bowel disease (including e.g., ulcerative colitis, Crohn's disease, and Irritable Bowel Syndrome), endocrine ophthalmopathy, Grave's disease, sarcoidosis, primary biliary cirrhosis, juvenile diabetes (diabetes mellitus type I), uveitis (anterior and posterior), keratoconjunctivitis sicca and vernal keratoconjunctivitis, Behcet disease, lichen planopilaris, lichen planus, hidradenitis suppurativa, acne, recurrent aphthous stomatitis, and periodontitis, pyoderma gangraenosum, and other neutrophil dermatoses, *Pityriasis rubra* pilaris, bullous pemphigoid and ichthyosis, endometriosis, non-alcoholic steatohepatitis, interstitial lung fibrosis, glomerulonephritis (with and without nephrotic syndrome, e.g., including idiopathic nephrotic syndrome or minimal change nephropathy), tumors, multiple sclerosis, autism, depressiona DNA, Alzheimer's disease, inflammatory disease of skin and cornea, myositis, loosening of bone implants, metabolic disorders, such as atherosclerosis, diabetes, and dislipidemia.

WO 2009/089036 discloses that modulators of IL-17 activity may be administered to inhibit or reduce the severity of ocular inflammatory disorders, in particular ocular surface inflammatory disorders including Dry Eye Syndrome (DES). Consequently, the compounds in accordance with the present invention are useful in the treatment and/or prevention of an IL-17-mediated ocular inflammatory disorder, in particular an IL-17-mediated ocular surface inflammatory disorder including Dry Eye Syndrome. Ocular surface inflammatory disorders include Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory conditions, conjunctival scarring disorders, ocular autoimmune conditions, Pemphigoid syndrome, Stevens-Johnson syndrome, ocular allergy, severe allergic (atopic) eye disease, conjunctivitis, and microbial keratitis. Particular categories of Dry Eye Syndrome include keratoconjunctivitis sicca (KCS), Sjogren syndrome, Sjogren syndrome-associated keratoconjunctivitis sicca, non-Sjogren syndrome-associated keratoconjunctivitis sicca, keratitis sicca, sicca syndrome, xerophthalmia, tear film disorder, decreased tear production, aqueous tear deficiency (ATD), meibomian gland dysfunction, and evaporative loss.

WO2021239743 discloses that IL 17 modulators may be useful for treating acute lung injury, Alzheimer's Disease, ankylosing spondylitis, axial spondyloarthritis, and other spondyloarthropathies, arthritis, asthma (including severe asthma), atopic dermatitis, autoimmune diabetes other autoimmune disorders, autoimmune thyroiditis, bone resorption, cancer (both solid tumours such as melanomas, sarcomas, squamous cell carcinomas, transitional call cancers, ovarian cancers, and hematologic malignancies, and in particular acute myelogenous leukaemia, chronic lymphocytic leukemia, gastric cancer, and colon cancer), Castleman's disease, contact dermatitis, Crohn's Disease, chronic myelogenous leukemia, chronic obstructive pulmonary disease (CORD), coeliac disease, cystic fibrosis, dermatomyositis, discoid lupus erythematosus, eczema, enthesitis-related arthritis, endotoxic shock associated with infection, exophthalmos, fibrosing disorders including pulmonary fibrosis, gall bladder disease, giant cell arteritis, graft-versus-host disease, heart disease including ischaemic diseases such as myocardial infarction as well as atherosclerosis, hepatoblastomas, hypochlorhydia, immune mediated inflammatory disorders of the central and peripheral nervous system such as multiple sclerosis and Guillain-Barr syndrome, infections (viral, bacterial, fungal, and parasitic), inflammatory bowel disease, intravascular coagulation, irritable bowel syndrome, liver fibrosis, lyme arthritis, meningoencephalitis, myocarditis, meningoencephalitis, osteoporosis, pancreatitis, Parkinson's disease, pelvic inflammatory disease, pain (particularly pain associated with inflammation), periodontitis, peritonitis, Peyronie's Disease, Pilonidal disease, psoriasis, psoriatic arthritis (PsA), renal fibrosis, rheumatoid arthritis, scleroderma or systemic sclerosis, stroke, surgical adhesions, systemic lupus erythematosus (SLE), systemic onset juvenile idiopathic arthritis (JIA), trauma (surgery), transplant rejection, Type I diabetes, ulcerative colitis, uveitis, and vasculitis.

The compounds of the present invention may be useful for treating the above mentioned diseases or disorders.

The compounds of the present invention may thus be useful for preventing, treating or ameliorating any of the following diseases: psoriasis, ankylosing spondylitis, spondyloarthritis or psoriatic arthritis, lichen planus, Sjögren's syndrome, acne, vitiligo, alopecia areata, ichthyosis, acute and chronic liver diseases, gout, osteoarthritis, systemic lupus erythematosus (SLE), lupus nephritis (LN), discoid lupus erythematosus (DLE)), multiple sclerosis, plaque psoriasis, pustular psoriasis, rheumatoid arthritis, *Pityriasis rubra* pilaris, pyoderma gangrenosum, hidradenitis suppurativa, discoid lupus erythematosus, papulopustolar rosacea, atopic dermatitis, Ichthyosis, bullous pemphigoid, scleroderma, tendinopathy, chronic wounds, and cancer.

In an embodiment the invention relates to the use of a compound of general formula (I) as defined above, in the manufacture of a medicament for the prophylaxis, treatment or amelioration of any of the following diseases: psoriasis, ankylosing spondylitis, spondyloarthritis or psoriatic arthritis, lichen planus, lupus nephritis, Sjögren's syndrome, acne, vitiligo, alopecia areata, ichthyosis, acute and chronic liver diseases, gout, osteoarthritis, SLE, LN, DLE, multiple sclerosis, plaque psoriasis, pustular psoriasis, rheumatoid arthritis, *Pityriasis rubra* pilaris, pyoderma gangrenosum, hidradenitis suppurativa, discoid lupus erythematosus, Papulopustolar rosacea, atopic dermatitis, Ichthyosis, bullous pemphigoid, scleroderma, tendinopathy, chronic wounds, and cancer.

In an embodiment the invention relates to the use of a compound of general formula (I) as defined above, in the manufacture of a medicament for the prophylaxis, treatment or amelioration of autoimmune diseases, such as psoriasis, ankylosing spondylitis, spondyloarthritis, hidradenitis suppurativa or psoriatic arthritis.

In an embodiment the invention relates to a method of preventing, treating or ameliorating autoimmune diseases, such as psoriatic arthritis, lichen planus, lupus nephritis, Sjögren's syndrome, acne, vitiligo, alopecia areata, ichthyosis, acute and chronic liver diseases, gout, osteoarthritis, SLE (besides LN and DLE), multiple sclerosis, plaque psoriasis, pustular psoriasis, rheumatoid arthritis, *Pityriasis rubra* pilaris, pyoderma gangrenosum, hidradenitis suppurativa, discoid lupus erythematosus, Papulopustolar rosacea, atopic dermatitis, Ichthyosis, bullous pemphigoid, scleroderma, tendinopathy, chronic wounds, and cancer, the method comprising administering to a person suffering from at least one of said diseases an effective amount of one or more compounds according to general formula (I), optionally together with a pharmaceutically acceptable carrier or one or more excipients, optionally in combination with other therapeutically active compounds.

In an embodiment the invention relates to a method of preventing, treating or ameliorating autoimmune diseases, such as psoriasis, ankylosing spondylitis, spondyloarthritis, hidradenitis suppurativa or psoriatic arthritis, the method comprising administering to a person suffering from at least one of said diseases an effective amount of one or more compounds according to general formula (I), optionally together with a pharmaceutically acceptable carrier or one or more excipients, optionally in combination with other therapeutically active compounds.

Besides being useful for human treatment, the compounds of the present invention may also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of Formula (I), optionally together with one or more other therapeutically active compound(s), together with a pharmaceutically acceptable excipient, vehicle or carrier(s). The excipient must be "acceptable" in the sense of being compatible with the other ingredients of the composition and not deleterious to the recipient thereof.

Conveniently, the active ingredient comprises from 0.0001-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.001 mg and 1000 mg, preferably between 0.01 mg and 300 mg of a compound of Formula (I).

A suitable dosage of the compound of the invention will depend, inter alia, on the age and condition of the patient, the severity of the disease to be treated and other factors well known to the practising physician. The compound may be administered either orally, parenterally, topically, transdermally or intradermally and other routes according to different dosing schedules, e.g., daily, weekly or with monthly intervals. In general, a single dose will be in the range from 0.001 to 400 mg/kg body weight.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g., those in a form suitable for oral, rectal, parenteral transdermal, intradermal, ophthalmic, topical, nasal, sublingual or buccal administration.

The formulations may conveniently be presented in dosage unit form and may be prepared by but not restricted to any of the methods well known in the art of pharmacy, e.g., as disclosed in Remington, *The Science and Practice of Pharmacy*, 21 ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient.

A tablet may be made by compressing, moulding or freeze drying the active ingredient optionally with one or more accessory ingredients. Compressed tablets may be prepared by compressing, in a suitable machine, the active ingredient(s) in a free-flowing form; for example with a lubricant; a disintegrating agent or a dispersing agent. Moulded tablets may be made by moulding, in a suitable machine, a mixture of the powdered active ingredient and suitable carrier. Freeze dried tablets may be formed in a freeze-dryer from a solution of the drug substance.

Formulations suitable for parenteral administration conveniently comprise a sterile oily or aqueous preparation of the active ingredients, which is preferably isotonic with the blood of the recipient, e.g., isotonic saline, isotonic glucose solution or buffer solution. Liposomal formulations are also suitable for parenteral administration.

Transdermal formulations may be in the form of a plaster, patch, microneedles, liposomal or nanoparticulate delivery systems or other cutaneous formulations applied to the skin.

Formulations suitable for ophthalmic administration may be in the form of a sterile aqueous preparation of the active ingredients. Liposomal formulations or biodegradable polymer systems may also be used to present the active ingredient for ophthalmic administration.

Formulations suitable for topical, such as dermal, intradermal or ophthalmic administration include liquid or semisolid preparations, solutions or suspensions.

Formulations suitable for nasal or buccal administration include powder, self-propelling, and spray formulations, such as aerosols and atomisers.

All references, including publications, patent applications, and patents, cited herein are hereby incorporated by reference in their entirety and to the same extent as if each reference were individually and specifically indicated to be incorporated by reference, regardless of any separately provided incorporation of particular documents made elsewhere herein.

Methods of Preparation

The compounds of the present invention can be prepared in a number of ways well known to those skilled in the art of synthesis. The compounds of the invention could for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used.

The compounds of the present invention or any intermediate could be purified, if required, using standard methods well known to a synthetic organist chemist, e.g., methods described in "Purification of Laboratory Chemicals", 6$^{th}$ ed. 2009, W. Amarego and C. Chai, Butterworth-Heinemann.

Starting materials are either known or commercially available compounds, or may be prepared by routine synthetic methods well known to a person skilled in the art. Unless otherwise noted, reagents and solvents were used as received from commercial suppliers. The organic solvents used were usually anhydrous. The solvent ratios indicated refer to vol:vol unless otherwise noted. Thin layer chromatography was performed using Merck 6OF254 silica-gel TLC plates. Visualisation of TLC plates was performed using UV light (254 nm) or by an appropriate staining technique.

Proton nuclear magnetic resonance spectra were obtained at the stated frequencies in the solvents indicated. Tetramethylsilane was used as an internal standard for proton spectra. The value of a multiplet, either defined doublet (d), triplet (t), quartet (q) or (m) at the approximate midpoint is given unless a range is quoted. (br) indicates a broad peak, whilst (s) indicates a singlet.

Mass spectra were obtained using the following methods. LCMS Method 1 was used, unless otherwise stated.

LCMS Method 1:
Column: Acquity UPLC HSS T3 1.8 µm; 2.1×50 mm
Flow: 0.7 mL/min
Column temp: 30° ° C.
Mobile phases: A: 10 mM Ammonium acetate+0.1% formic acid, B: 100% Acetonitrile+0.1% formic acid
UV: 240-400 nm
Injection volume: 1 µl
Gradient:

| Time (min) | A % | B % |
|---|---|---|
| 0.0 | 99% | 1% |
| 0.5 | 94% | 6% |
| 1.0 | 94% | 6% |
| 2.6 | 5% | 95% |
| 3.8 | 5% | 95% |
| 3.81 | 99% | 1% |
| 4.8 | 99% | 1% |

UPLC (inlet method): XEV Metode 1 CM
MS—method: Pos_50_1000 or Neg_50_1000
Instruments: Waters Acquity UPLC, Waters XEVO G2-XS QTof, Waters PDA (Photodiode Array)

LCMS Method 2:
Mass spectra were obtained on a Waters Quattro micro API/Waters SQD2/Waters Quattro Premier Spectrometer using electrospray ionization and atmospheric-pressure chemical ionization with the column and solvents indicated.

LCMS Method 3:
Column: Waters Acquity UPLC HSS T3 1.8 µm, 2.1×50 mm.
Column temperature: 60° C.
UV: PDA 210-400 nm.
Injection volume: 2 µl.
Eluents: A: 10 mM Ammonium acetate with 0.1% formic acid, B: 100% Acetonitrile with 0.1% formic acid.
Gradient:

| Time (min) | A % | B % | Flow (mL/min) |
|---|---|---|---|
| 0.0 | 95 | 5 | 1.2 |
| 0.9 | 5 | 95 | 1.2 |
| 0.91 | 5 | 95 | 1.3 |
| 1.2 | 5 | 95 | 1.3 |
| 1.21 | 5 | 95 | 1.2 |
| 1.4 | 95 | 5 | 1.2 |

MS: Electrospray switching between positive and negative ionisation.
Instruments: Waters ACQUITY, Waters SQD, Waters PDA (Photodiode array)

LCMS Method 4:
Column: Waters ACQUITY BEH 1.7 µm, 2.1×50 mm.
Column temperature: 60° C.
UV: PDA 210-400 nm.
Injection volume: 2 µl.
Eluents: A: 10 mM Ammonium Bicarbonate, B: 100% Acetonitrile
Gradient:

| Time (min) | % A | % B | Flow (mL/min) |
|---|---|---|---|
| 0.0 | 95 | 5 | 1.2 |
| 0.9 | 5 | 95 | 1.2 |
| 0.91 | 5 | 95 | 1.3 |
| 1.2 | 5 | 95 | 1.3 |
| 1.21 | 5 | 95 | 1.2 |
| 1.4 | 95 | 5 | 1.2 |

MS: Electrospray positive or negative ionisation.
Instruments: Waters ACQUITY, Waters QDa (MS detector), Waters PDA (Photodiode Array)

Basic Preparative HPLC Conditions:
Column: XBridge Prep C18 5 µm OBD, 19×150 mm
Eluents: Ammonium formate (50 mM)/acetonitrile, 10-100% acetonitrile
Flow: 30 mL/min Acidic Preparative HPLC Conditions:
Column: XTerra® RP-18 5 µm OBD, 19×150 mm
Eluents: 0.1% formic acid in water/acetonitrile, 10-100% acetonitrile
Flow: 30 mL/min The following abbreviations have been used throughout:
ABPR automated back pressure regulator
Boc tert-butoxycarbonyl
BOP (benzotriazol-1-yloxy)tris(dimethylamino)phosphonium hexafluorophosphate
CBz benzyloxycarbonyl
CDI carbonyldiimidazole
DCC dicyclohexylcarbodiimide
DCM dichloromethane
DEA diethylamine
DEAD diethyl azodicarboxylate
DIAD diisopropyl azodicarboxylate
DIPEA diisopropylethylamine
DMF N,N-dimethylformamide
DMSO dimethylsulfoxide
dppf 1,1'-bis(diphenylphosphino)ferrocene
EDC N-(3-dimethylaminopropyl)-N'-ethylcarbodiimide
EtOAc ethyl acetate
EtOH ethanol
HATU 1-[bis(dimethylamino)methylene]-1H-1,2,3-triazolo[4,5-b]pyridinium 3-oxide hexafluorophosphate HBTU N,N,N',N'-tetramethyl-O-(1H-benzotriazol-1-yl)uronium hexafluorophosphate
HPLC high-performance liquid chromatography
KOAc potassium acetate
LCMS liquid chromatography-mass spectrometry
mCPBA meta-chloroperoxybenzoic acid
MeCN acetonitrile
MeOH methanol
MHz megahertz
NBS N-bromosuccinimide
NMR nuclear magnetic resonance
ppm parts per million
PyBOP (benzotriazol-1-yloxy)tripyrrolidinophosphonium hexafluorophosphate
RuPhos Pd G2 Chloro(2-dicyclohexylphosphino-2',6'-diisopropoxy-1,1'-biphenyl)[2-(2'-amino-1,1'-biphenyl)]palladium(II)
SFC supercritical fluid chromatography
TFA trifluoroacetic acid
THF tetrahydrofuran
TLC thin layer chromatography
T3P propanephosphonic acid anhydride General Methods Compounds of the invention may be prepared according to the following non-limiting general methods and examples:

Scheme 1

Synthesis of compounds of general formula (I), wherein X, $R^1$, $R^2$, $R^3$ and $R^4$ are as previously defined, PG represents a suitable protecting group, $Q^1$ represents a suitable halogen, such as Br, and $Q^2$ represents a suitable halogen, such as Br, or a boronic acid or ester.

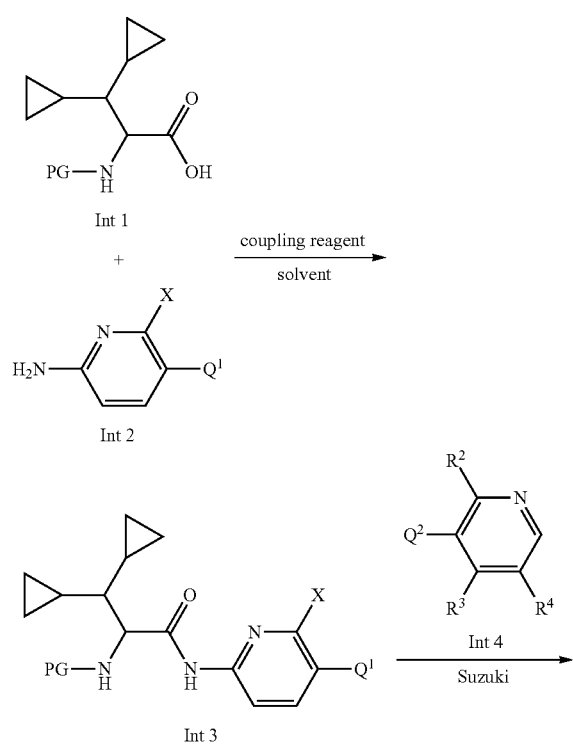

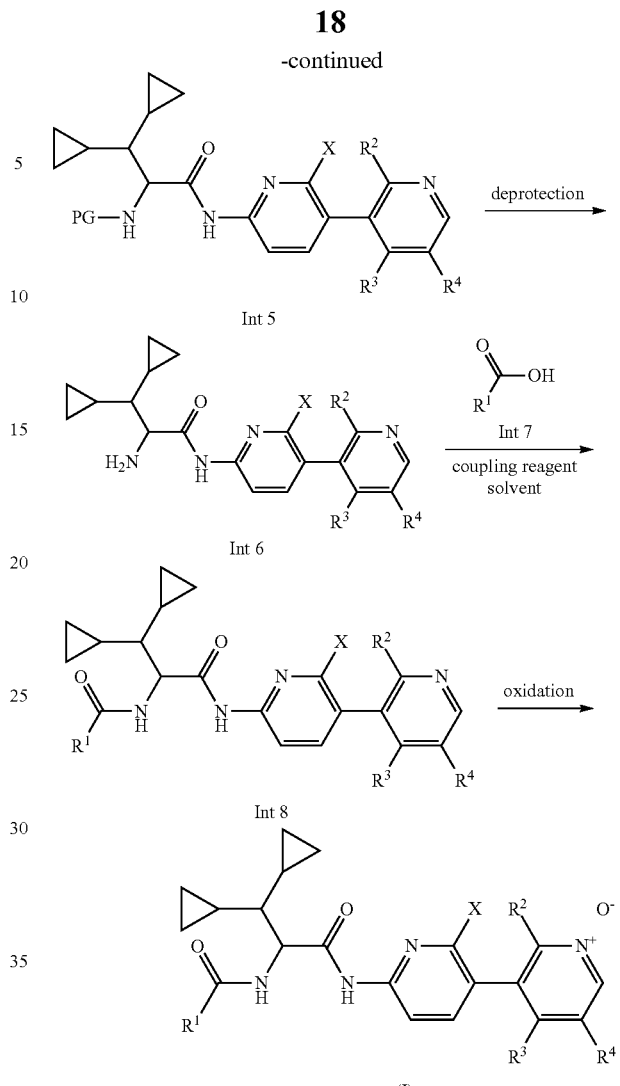

Compounds of general formula (I) can be prepared as shown in Scheme 1. Compounds of general formula (Int 1), which are synthesized in a racemic form or an enantiomerically pure form as described in WO2021250194, are coupled with aminopyridines of general formula (Int 2), which are either commercially available or synthesized, in the presence of a coupling reagent such as $POCl_3$ and a base, such as pyridine, to form compounds of formula (Int 3). Compounds of general formula (Int 3) may be reacted with compounds of formula (Int 4), which are either commercially available or synthesized, to give compounds of general formula (Int 5). When $Q^2$ is a boronic acid or ester, the reaction takes place in the presence of a catalyst, such as [1,1'-bis(diphenylphosphino)ferrocene]palladium(II) dichloride $PdCl_2(dppf)$, or bis(triphenylphosphine)palladium(II) dichloride, $PdCl_2(PPh_3)_2$, in the presence of an aqueous base, such as $K_2CO_3$, $K_3PO_4$ or $Na_2CO_3$, in a suitable solvent, such as dioxane, DMF or toluene, at a suitable temperature, such as between 80 and 100° C. When both $Q^1$ and $Q^2$ are a halogen, such as Br, one of the compounds of general formula (Int 3) and (Int 4) will first be converted to a boronic ester or acid by reaction with a reagent, such as bis(pinacolato)diboron, in the presence of a catalyst, such as [1,1'-bis(diphenylphosphino)ferrocene]palladium(II) dichloride $PdCl_2(dppf)$, and a suitable base, such as potassium acetate, in a suitable anhydrous solvent, such as dioxane, at a suitable temperature, such as between 80 and 100° C. The resulting boronic ester or acid, which may be isolated or not, and purified or not, is reacted with the other compound of general formula (Int 3) or (Int 4) in the presence of a catalyst, such as [1,1'-bis(diphenylphosphino) ferrocene]palladium(II) dichloride $PdCl_2(dppf)$, in the presence of an aqueous base, such as $K_2CO_3$, $K_3PO_4$ or $Na_2CO_3$, in a suitable solvent, such as dioxane, DMF or toluene, at a suitable temperature, such as between 80 and 100° C. Those skilled in the art will appreciate other metal mediated coupling reaction will also give rise to compounds of general formula (Int 5).

Protecting groups (PG), such as Cbz, on compounds of general formula (Int 5) can be removed by methods known to those skilled in the art to give compounds of general formula (Int 6). Compounds of general formula (Int 6) are coupled with compounds of general formula (Int 7), which are either commercially available or synthesized, in the presence of a coupling reagent such as HATU, HBTU, CDI, T3P, PyBOP, BOP, DCC, or EDC and in most of the cases in the presence of a base, such as DIPEA or triethylamine, in a suitable solvent, such as DMF or acetonitrile to form compounds of general formula (Int 8). Compounds of general formula (Int 8) can be oxidised by a suitable reagent, such as mCPBA or urea-hydrogen peroxide complex, in a suitable solvent, such as DCM, to give the N-oxides of general formula (I).

Scheme 2

Alternative synthesis of compounds of formula (Int 3), wherein X, $R^1$, $R^2$, $R^3$ and $R^4$ are as previously defined, PG represents a suitable protecting group and $Q^1$ and $Q^3$ represent suitable halogens such as Cl or Br.

Compounds of general formula (Int 3) can be prepared as shown in Scheme 2. Compounds of general formula (Int 1) are reacted with an ammonia equivalent, such as ammonium chloride, in the presence of a coupling reagent such as T3P, CDI, DCC, HATU, HBTU, and EDC and in the majority of cases, in the presence of a base, such as DIPEA or triethylamine, in a suitable solvent, such as DMF or acetonitrile or reacted with ammonium bicarbonate in the presence of tert-butoxycarbonyl tert-butyl carbonate and pyridine in a solvent, such as 1,4-dioxane, to form compounds of formula (Int 9). Compounds of formula (Int 9) can be reacted with compounds of formula (Int 10) in the presence of tetrakis (triphenylphosphine)-palladium(0) or palladium (II) acetate and 4,5-bis(diphenylphosphino)-9,9-dimethylxanthene and a base, such as $K_2CO_3$ or $Cs_2CO_3$, in a solvent, such as THF or DMF, to form compounds of formula (Int 3).

Scheme 3

Alternative synthesis of compounds of general formula (Int 8), wherein X, $R^1$, $R^2$, $R^3$ and $R^4$ are as previously defined, PG represents a suitable protecting group, $Q^1$ represents a suitable halogen, such as Br, and $Q^2$ represents a suitable halogen, such as Br, or a boronic acid or ester.

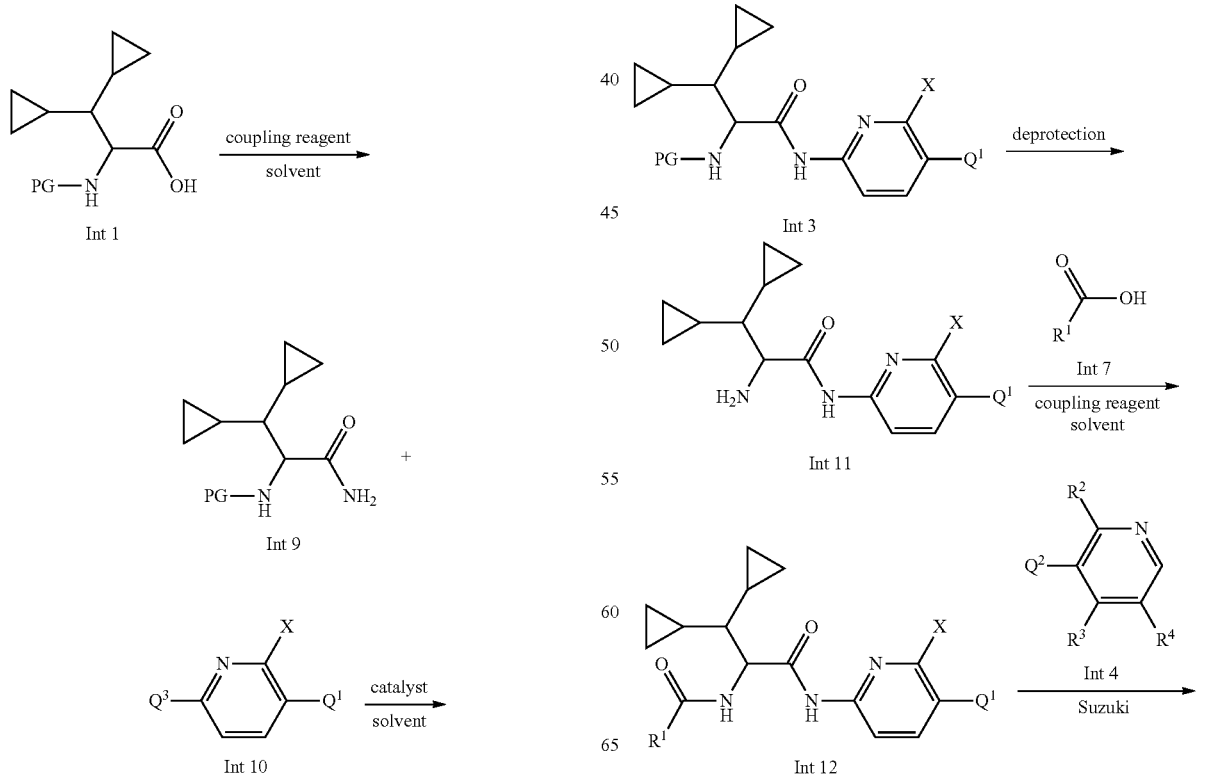

-continued

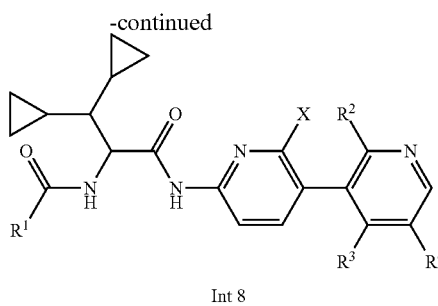

Int 8

Compounds of general formula (Int 8) can be prepared as shown in Scheme 3. Protecting groups (PG), such as Boc, on compounds of general formula (Int 3) can be removed by methods known to those skilled in the art to give compounds of general formula (Int 11). Compounds of general formula (Int 11) are coupled with compounds of general formula (Int 7), which are either commercially available or synthesized, in the presence of a coupling reagent such as HATU, HBTU, CDI, T3P, PyBOP, BOP, DCC, or EDC and in most of the cases in the presence of a base, such as DIPEA or triethylamine, in a suitable solvent, such as DMF or acetonitrile to form compounds of general formula (Int 12). Compounds of general formula (Int 12) may be reacted with compounds of formula (Int 4), which are either commercially available or synthesized, to give compounds of general formula (Int 8). When $Q^2$ is a boronic acid or ester, the reaction takes place in the presence of a catalyst, such as [1,1'-bis(diphenylphosphino)ferrocene]palladium(II) dichloride PdCl$_2$(dppf), or bis(triphenylphosphine)palladium(II) dichloride, PdCl$_2$(PPh$_3$)$_2$, in the presence of an aqueous base, such as K$_2$CO$_3$, K$_3$PO$_4$ or Na$_2$CO$_3$, in a suitable solvent, such as dioxane, DMF or toluene, at a suitable temperature, such as between 80 and 100° C. When both $Q^1$ and $Q^2$ are a halogen, such as Br, one of the compounds of general formula (Int 12) and (Int 4) will first be converted to a boronic ester or acid by reaction with a reagent, such as bis(pinacolato)diboron, in the presence of a catalyst, such as [1,1'-bis(diphenylphosphino)ferrocene]palladium(II) dichloride PdCl$_2$(dppf), and a suitable base, such as potassium acetate, in a suitable anhydrous solvent, such as dioxane, at a suitable temperature, such as between 80 and 100° C. The resulting boronic ester or acid, which may be isolated or not, and purified or not, is reacted with the other compound of general formula (Int 12) or (Int 4) in the presence of a catalyst, such as [1,1'-bis(diphenylphosphino)ferrocene]palladium(II) dichloride PdCl$_2$(dppf), in the presence of an aqueous base, such as K$_2$CO$_3$, K$_3$PO$_4$, or Na$_2$CO$_3$, in a suitable solvent, such as dioxane, DMF or toluene, at a suitable temperature, such as between 80 and 100° C. Those skilled in the art will appreciate other metal mediated coupling reaction will also give rise to compounds of general formula (Int 8).

Scheme 4

Alternative synthesis of compounds of general formula (Int 5), wherein X, $R^1$, $R^2$, $R^3$ and $R^4$ are as previously defined, OR represents an active ester, such as a pentafluorophenol ester, PG represents a suitable protecting group, $Q^1$ represents a suitable halogen, such as Br, Hal represents a suitable halogen, such as Cl or Br, and $Q^2$ represents a suitable halogen, such as Br, or a boronic acid or ester.

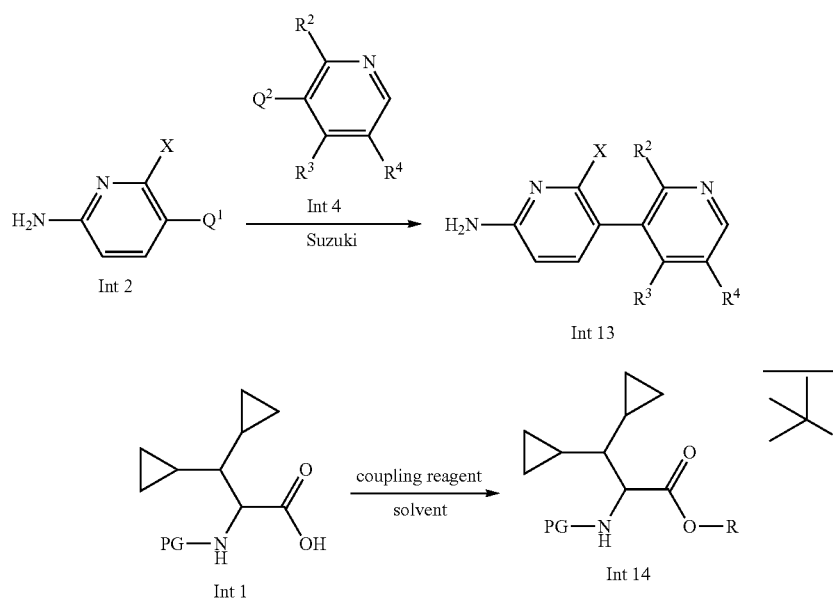

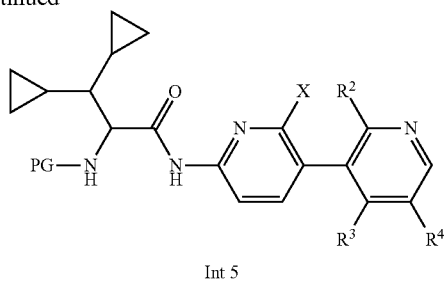

Int 5

Compounds of general formula (Int 5) can be prepared as shown in Scheme 4. Compounds of general formula (Int 2) may be reacted with compounds of formula (Int 4), which are either commercially available or synthesized, to give compounds of general formula (Int 13). When $Q^2$ is a boronic acid or ester, the reaction takes place in the presence of a catalyst, such as [1,1'-bis(diphenylphosphino)ferrocene]palladium(II) dichloride PdCl$_2$(dppf), or bis(triphenylphosphine)palladium(II) dichloride, PdCl$_2$(PPh$_3$)$_2$, in the presence of an aqueous base, such as K$_2$CO$_3$, K$_3$PO$_4$ or Na$_2$CO$_3$, in a suitable solvent, such as dioxane, DMF or toluene, at a suitable temperature, such as between 80 and 100° C. When both $Q^1$ and $Q^2$ are a halogen, such as Br, one of the compounds of general formula (Int 2) and (Int 4) will first be converted to a boronic ester or acid by reaction with a reagent, such as bis(pinacolato)diboron, in the presence of a catalyst, such as [1,1'-bis(diphenylphosphino)ferrocene]palladium(II) dichloride PdCl$_2$(dppf), and a suitable base, such as potassium acetate, in a suitable anhydrous solvent, such as dioxane, at a suitable temperature, such as between 80 and 100° C. The resulting boronic ester or acid, which may be isolated or not, and purified or not, is reacted with the other compound of general formula (Int 2) or (Int 4) in the presence of a catalyst, such as [1,1'-bis(diphenylphosphino)ferrocene]palladium(II) dichloride PdCl$_2$(dppf), in the presence of an aqueous base, such as K$_2$CO$_3$, K$_3$PO$_4$ or Na$_2$CO$_3$, in a suitable solvent, such as dioxane, DMF or toluene, at a suitable temperature, such as between 80 and 100° C.

Compounds of general formula (Int 1) can be reacted to form activated esters of general formula (Int 14). Typically this could be a reaction of a compound of general formula (Int 1) with (2,3,4,5,6-pentafluorophenyl) 2,2,2-trifluoroacetate in a solvent such as DCM, in the presence of a suitable base such as pyridine or triethylamine in a solvent such as MeCN or DCM, or with 1-hydroxypyrrolidine-2,5-dione in the presence of a coupling reagent such as EDC or DCC in a suitable solvent such as DCM or THF. Compounds of general formula (Int 14) can be reacted with compounds of general formula (Int 13) in the presence of a suitable alkylmagnesium halide, such as ${}^t$BuMgCl or ${}^t$BuMgBr, in a suitable solvent, such as THF, to give the compounds of general formula (Int 5).

Scheme 5

Alternative synthesis of compounds of general formula (I), wherein X, $R^1$, $R^2$, $R^3$ and $R^4$ are as previously defined, PG represents a suitable protecting group.

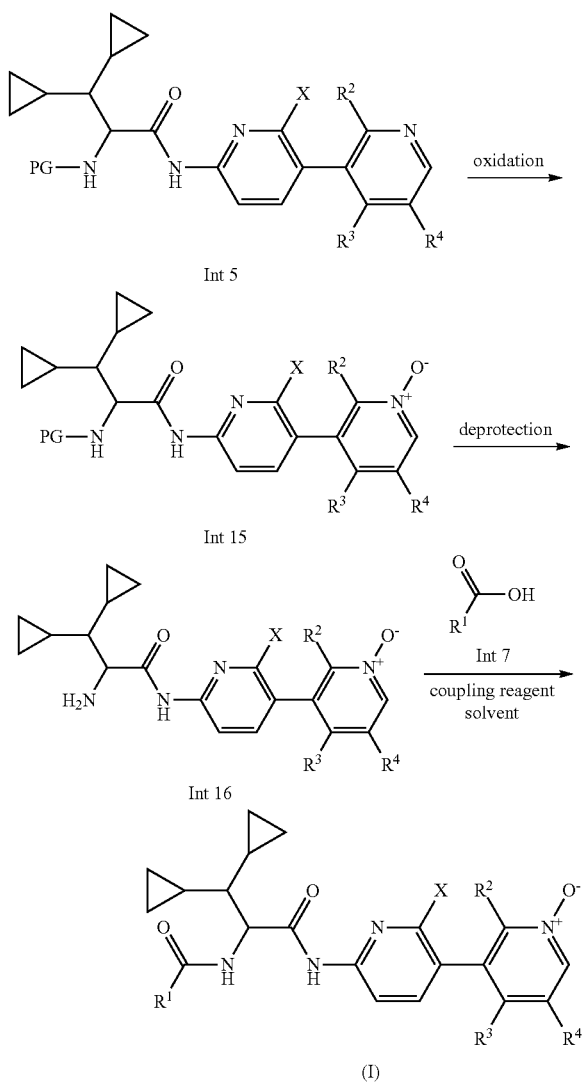

Compounds of general formula (I) can be prepared as shown in Scheme 5. Compounds of general formula (Int 5) can be oxidised by a suitable reagent, such as mCPBA or urea-hydrogen peroxide complex, in a suitable solvent, such as DCM, to give the N-oxides of general formula (Int 15). Protecting groups (PG), such as Cbz, on compounds of general formula (Int 15) can be removed by methods known to those skilled in the art to give compounds of general formula (Int 16). Compounds of general formula (Int 16) are coupled with compounds of general formula (Int 7), which are either commercially available or synthesized, in the presence of a coupling reagent such as HATU, HBTU, CDI, T3P, PyBOP, BOP, DCC, or EDC and in most of the cases in the presence of a base, such as DIPEA or triethylamine, in a suitable solvent, such as DMF or acetonitrile to form compounds of general formula (I).

Scheme 6

Preparation of compounds of formula (Int 7) wherein $R^5$ is as previously defined and Alk is a suitable alkyl group, such as methyl or ethyl.

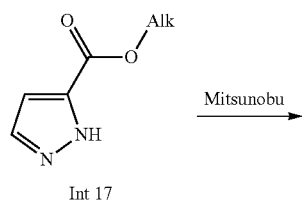

Int 17

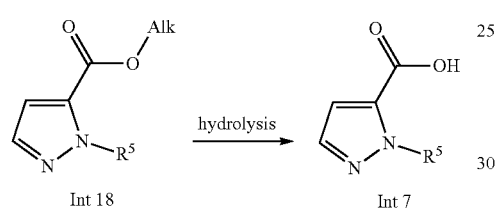

Int 18     Int 7

Compounds of general formula (Int 7) can be prepared as shown in Scheme 6. Compounds of formula (Int 17) that are commercial or synthesized can be reacted with alcohols, that are commercial or synthesized, under Mitsunobu conditions, namely in the presence of a phosphine, such as triphenylphosphine, and a diazodicarboxylate, such as DEAD or DIAD, in a suitable solvent, such as toluene or THF, to give compounds of formula (Int 18). Those skilled in the art will appreciate that some of the embodiments of $R^5$ will undergo literature precedented transformation or deprotection before hydrolysis with an appropriate base such as LiOH or NaOH in a suitable solvent, such as MeOH or THF, to give compounds of general formula (Int 7).

Preparations

Preparation 1: (2S)-2-amino-N-(5-bromo-6-fluoro-2-pyridyl)-3,3-dicyclopropyl-propanamide hydrochloride salt

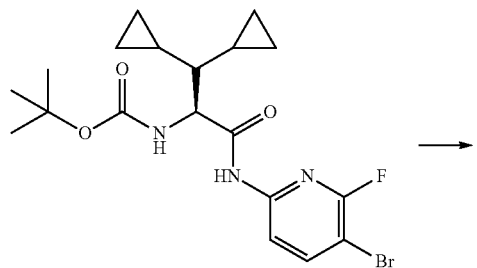

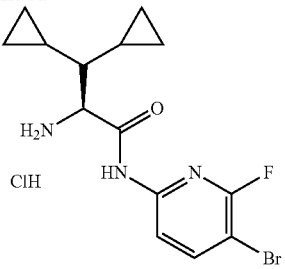

Tert-butyl N-[(1S)-1-[(5-bromo-6-fluoro-2-pyridyl)carbamoyl]-2,2-dicyclopropyl-ethyl]carbamate (Preparation 90 from WO2021250194) (5.07 g, 11.5 mmol) was suspended in MeOH (34.4 mL), 4 M HCl in dioxane (34.4 mL, 138 mmol) was added and the mixture was stirred for 1 hour at room temperature. 30 mL of MeOH was added, the mixture was concentrated in vacuo and dried under reduced pressure to give the title compound (4.36 g, 100%) as a yellow foam. LCMS (METHOD 3) (ES): m/z 342.4, 344.4 [M+H]+, RT=0.56 min.

Preparation 2: N-[(1S)-1-[(5-bromo-6-fluoro-2-pyridyl)carbamoyl]-2,2-dicyclopropyl-ethyl]-2-isopropyl-pyrazole-3-carboxamide

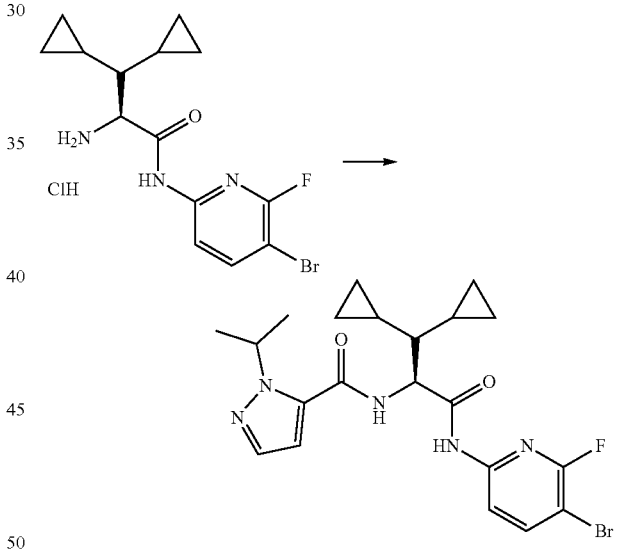

To a mixture of 2-isopropylpyrazole-3-carboxylic acid (1.94 g, 12.6 mmol), the amine of Preparation 1 (4.36 g, 11.5 mmol) and DIPEA (4.44 g, 5.99 mL, 34.4 mmol) in MeCN (57.3 mL) was added HATU (4.79 g, 12.6 mmol). The mixture was stirred for 1 hour at room temperature, then concentrated in vacuo. 50 mL of water was added, and the mixture was extracted with EtOAc (3×100 mL). The combined organic phases were washed with brine (25 mL), dried (MgSO4), filtered, and concentrated in vacuo, affording a yellowish solid. The solid was suspended in MeCN (50 mL) and left to stand at room temperature overnight. The solid was collected by filtration, washed with MeCN (2×5 mL) and dried under reduced pressure to give the title compound (4.99 g, 89%) as a colorless solid. LCMS (METHOD 3) (ES): m/z 476.5, 478.5 [M−H]−, RT=0.90 min; 1H NMR (400 MHZ, DMSO-d6) δ 11.04 (s, 1H), 8.46 (d, J=8.4 Hz, 1H), 8.24 (t, J=8.9 Hz, 1H), 7.97 (dd, J=8.6, 1.4 Hz, 1H), 7.51 (d, J=1.9 Hz, 1H), 6.91 (d, J=2.0 Hz, 1H), 5.37 (hept, J=6.6 Hz, 1H), 4.87 (t, J=8.0 Hz, 1H), 1.37 (d, J=6.6 Hz, 3H), 1.34 (d, J=6.6 Hz, 3H), 1.02-0.90 (m, 1H), 0.90-0.78 (m, 1H), 0.78-0.68 (m, 1H), 0.52-0.42 (m, 1H), 0.42-0.05 (m, 7H).

Preparation 3: N-[(1S)-1-(dicyclopropylmethyl)-2-[[6-fluoro-5-(5-methoxy-2-methyl-3-pyridyl)-2-pyridyl]amino]-2-oxo-ethyl]-2-isopropyl-pyrazole-3-carboxamide

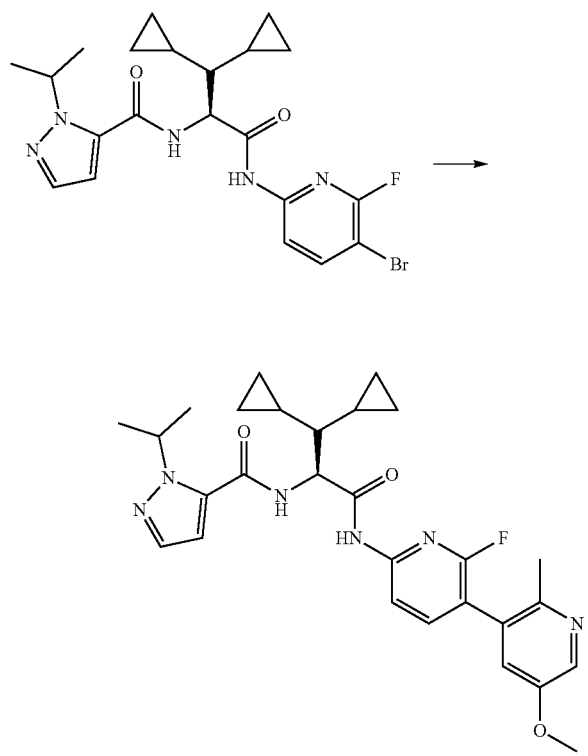

Pd(dppf)Cl$_2$ (33 mg, 0.045 mmol) was added to a degassed mixture of the compound of Preparation 2 (432 mg, 0.903 mmol), bis(pinacolato)diboron (275 mg, 1.08 mmol), and KOAc (266 mg, 2.71 mmol) in dry dioxane (15 mL) in a 2-necked flask. The mixture was stirred at 100° C. under N$_2$ for 1 hour, then cooled to room temperature and evaporated. EtOAc (30 mL) was added to the residue, the mixture was washed with water (15 mL), dried (Na$_2$SO$_4$) and evaporated to give a crude mixture of boronic acid and boronic ester (340 mg) that was used without further purification.

A mixture of the boronic acid and ester (340 mg), 3-bromo-5-methoxy-2-methyl-pyridine (233 mg, 1.15 mmol, K$_2$CO$_3$ (265 mg, 1.92 mmol) and Pd(dppf)Cl$_2$ (28 mg, 0.038 mmol) in degassed THF and water (15 mL:3 mL) in a 2-necked flask fitted with a condenser was stirred at 80° C. for 1 hour under N$_2$. The mixture was cooled to room temperature, diluted with EtOAc (20 mL), washed with brine (15 mL), dried (Na$_2$SO$_4$) and evaporated. Purification by column chromatography (EtOAc:heptane) gave the title compound (310 mg, 66%) as a colorless syrup. LCMS (METHOD 3) (ES): m/z 521.7 [M+H]$^+$, RT=0.95 min.

Preparation 4: N-[(1S)-1-(dicyclopropylmethyl)-2-[[6-fluoro-5-(5-fluoro-2-methyl-3-pyridyl)-2-pyridyl]amino]-2-oxo-ethyl]-2-isopropyl-pyrazole-3-carboxamide

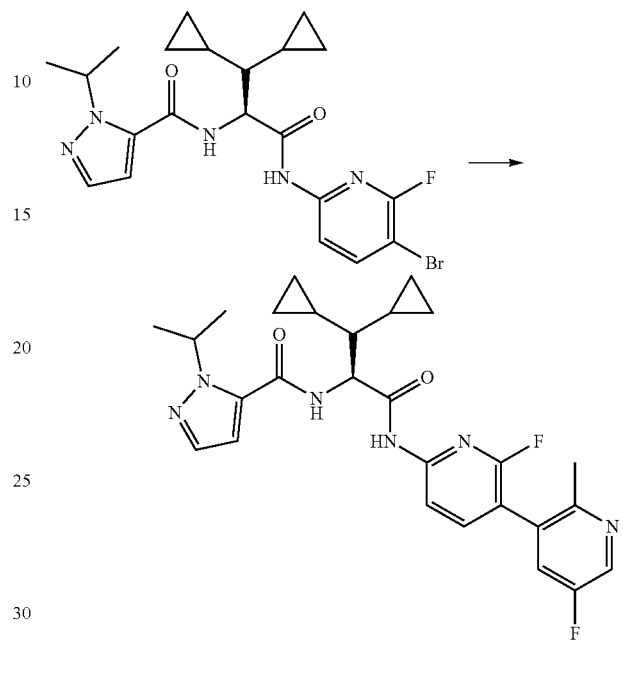

According to the method of Preparation 3 the compound of Preparation 2 (457 mg, 0.96 mmol) was reacted with bis(pinacolato)diboron to give a crude mixture of boronic acid and boronic ester. This mixture was then reacted with 3-bromo-5-fluoro-2-methyl-pyridine (180 mg, 0.94 mmol) according to the method of Preparation 3 to give the title compound (412 mg, 86%) as a colorless solid. LCMS (METHOD 3) (ES): m/z 509.7 [M+H]$^+$, RT=0.87 min; $^1$H NMR (600 MHZ, DMSO-d$_6$) δ 10.83 (s, 1H), 8.29 (d, J=2.9 Hz, 1H), 8.25 (d, J=8.5 Hz, 1H), 7.89 (dd, J=8.2, 1.7 Hz, 1H), 7.79 (dd, J=10.1, 8.1 Hz, 1H), 7.52 (dd, J=9.2, 2.9 Hz, 1H), 7.28 (d, J=1.9 Hz, 1H), 6.69 (d, J=2.0 Hz, 1H), 5.15 (hept, J=6.6 Hz, 1H), 4.68 (t, J=8.0 Hz, 1H), 2.11 (s, 3H), 1.15 (d, J=6.6 Hz, 3H), 1.11 (d, J=6.6 Hz, 3H), 0.81-0.71 (m, 1H), 0.68-0.60 (m, 1H), 0.54 (td, J=9.5, 7.5 Hz, 1H), 0.30-0.22 (m, 1H), 0.20-0.13 (m, 1H), 0.12--0.10 (m, 6H).

Preparation 5: N-[(1S)-1-(dicyclopropylmethyl)-2-[[5-(2,5-dimethyl-3-pyridyl)-6-fluoro-2-pyridyl]amino]-2-oxo-ethyl]-2-isopropyl-pyrazole-3-carboxamide

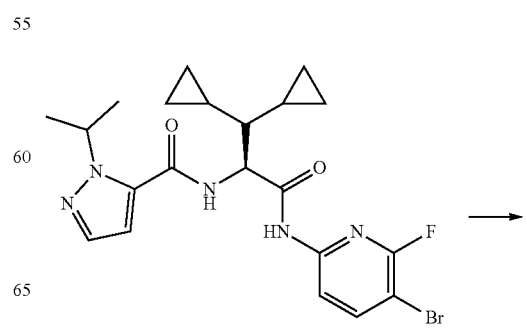

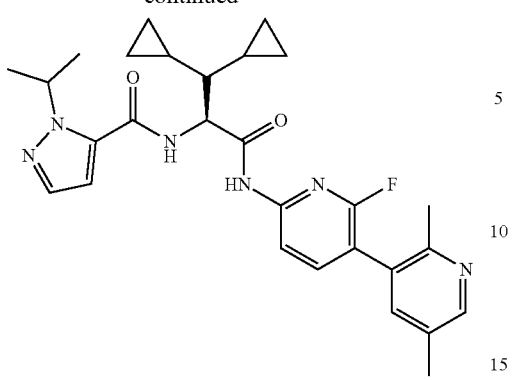

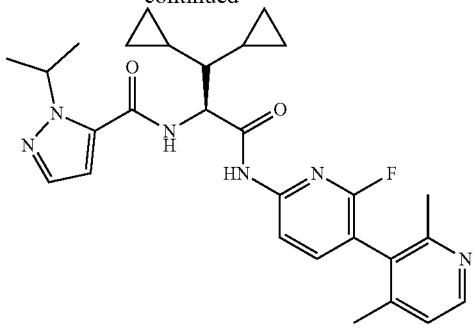

According to the method of Preparation 3 the compound of Preparation 2 (598 mg, 1.25 mmol) was reacted with bis(pinacolato)diboron to give a crude mixture of boronic acid and boronic ester. A solution of this crude mixture and 3-bromo-2,5-dimethyl-pyridine (326 mg, 1.75 mmol) in THF (15 mL) was placed in a 20 mL microwave vial and K$_2$CO$_3$ (432 mg, 3.13 mmol) dissolved in water (3 mL) was added. The mixture was degassed for 10 min with N$_2$, Pd(dppf)Cl$_2$ (46 mg, 0.063 mmol) was added, the vial was capped, and the mixture was stirred at 80° ° C. for 30 minutes. The mixture was cooled to room temperature, diluted with EtOAc (50 mL), washed with water (10 mL) and brine (10 mL), dried (MgSO$_4$), filtered, and concentrated in vacuo. The residue was dissolved in DCM (4 mL) and purified by column chromatography (heptane/EtOAc) to give the title compound (398 mg, 58%) as a colorless solid. LCMS (METHOD 3) (ES): m/z 503.5 [M−H]$^-$, RT=0.77 min; $^1$H NMR (600 MHZ, CDCl$_3$) δ 8.51 (s, 1H), 8.39 (d, J=2.3 Hz, 1H), 8.17 (dd, J=8.1, 1.3 Hz, 1H), 7.71 (dd, J=9.5, 8.1 Hz, 1H), 7.53 (d, J=2.0 Hz, 1H), 7.32 (d, J=2.2 Hz, 1H), 7.02 (d, J=7.9 Hz, 1H), 6.59 (d, J=2.0 Hz, 1H), 5.50 (hept, J=6.6 Hz, 1H), 4.89 (dd, J=7.9, 5.1 Hz, 1H), 2.40 (s, 3H), 2.34 (s, 3H), 1.51 (d, J=6.7 Hz, 3H), 1.49 (d, J=6.6 Hz, 3H), 0.97-0.76 (m, 3H), 0.70-0.52 (m, 4H), 0.44-0.34 (m, 2H), 0.32-0.21 (m, 2H).

Preparation 6: N-[(1S)-1-(dicyclopropylmethyl)-2-[[5-(2,4-dimethyl-3-pyridyl)-6-fluoro-2-pyridyl]amino]-2-oxo-ethyl]-2-isopropyl-pyrazole-3-carboxamide

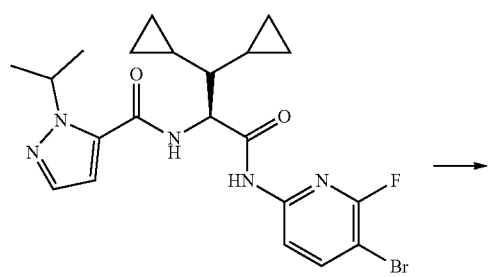

According to the method of Preparation 3 the compound of Preparation 2 (957 mg, 2.00 mmol) was reacted with bis(pinacolato)diboron to give a crude mixture of boronic acid and boronic ester. A solution of this crude mixture and 3-bromo-2,4-dimethyl-pyridine (231 mg, 1.24 mmol) was reacted according to the method of Preparation 5 to give the title compound (237 mg, 36%) as a mixture of atropisomers as a pale yellow oil. LCMS (METHOD 3) (ES): m/z 503.5 [M−H]$^-$, RT=0.75 and 0.76 min.

Preparation 7: N-[(1S)-1-(dicyclopropylmethyl)-2-[[5-(2-ethyl-3-pyridyl)-6-fluoro-2-pyridyl]amino]-2-oxo-ethyl]-2-isopropyl-pyrazole-3-carboxamide

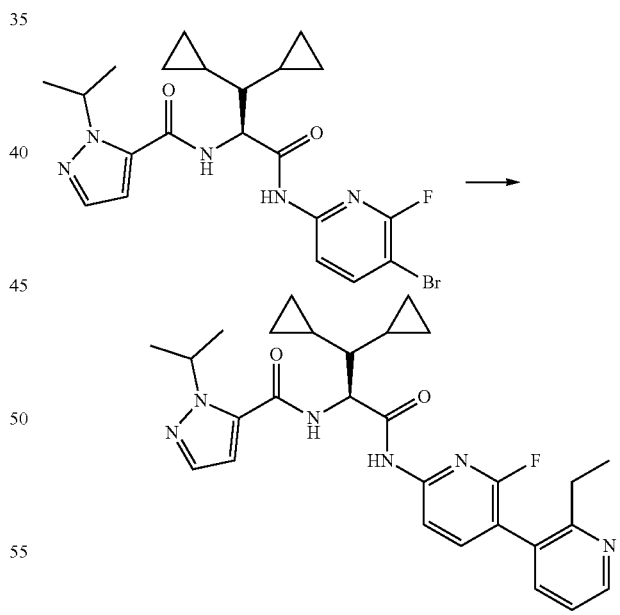

According to the method of Preparation 3 the compound of Preparation 2 (95 mg, 0.198 mmol) was reacted with bis(pinacolato)diboron to give a crude mixture of boronic acid and boronic ester. A solution of this crude mixture and 3-bromo-2-ethyl-pyridine (41.5 mg, 0.223 mmol) was reacted according to the method of Preparation 5 to give the title compound (40 mg, 40%) as a beige solid. LCMS (METHOD 3) (ES): m/z 505.7 [M+H]$^+$, RT=0.86 min.

Preparation 8: N-[(1S)-1-(dicyclopropylmethyl)-2-[[6-fluoro-5-[4-(trifluoromethyl)-3-pyridyl]-2-pyridyl]amino]-2-oxo-ethyl]-2-isopropyl-pyrazole-3-carboxamide Preparation 9: N-[(1S)-2,2-dicyclopropyl-1-[[5-(2-cyclopropyl-3-pyridyl)-6-fluoro-2-pyridyl]carbamoyl]ethyl]-2-isopropyl-pyrazole-3-carboxamide

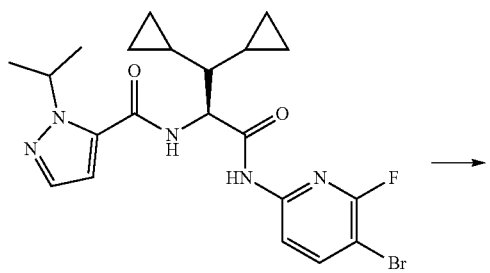

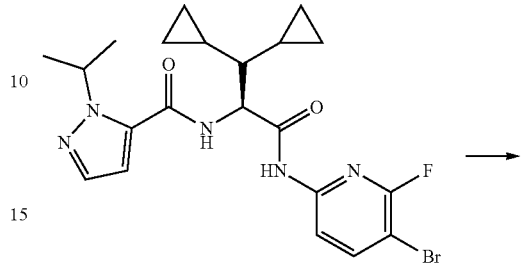

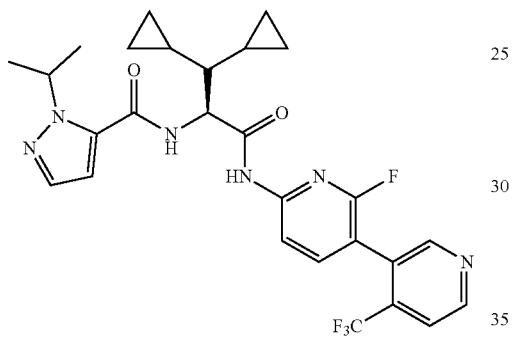

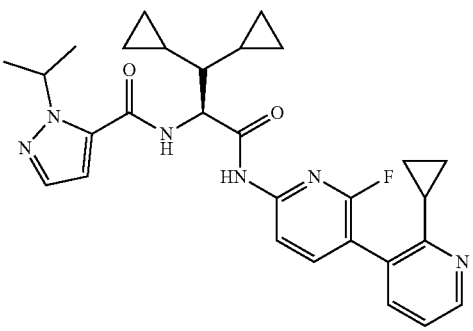

A mixture of the compound of Preparation 2 (339 mg, 0.709 mmol), bis(pinacolato)diboron (450 mg, 1.77 mmol) and KOAc (452 mg, 4.61 mmol) in dry dioxane (50 mL) was degassed with $N_2$ for 20 min. Pd(dppf)Cl$_2$ (104 mg, 0.142 mmol) was added, and the mixture was degassed for another 20 min. The mixture was stirred at 100° C. for 4 hours then a degassed solution of K$_2$CO$_3$ (245 mg, 1.77 mmol) in water (1 mL) and 3-bromo-4-(trifluoromethyl)pyridine (320 mg, 1.42 mmol) were added, and the reaction mixture was stirred at 100° C. for 20 hours. The mixture was filtered through a PTFE-filter, water (10 mL) was added, and the mixture was extracted with EtOAc (3×100 mL). The combined organic extracts were dried over Na$_2$SO$_4$ and concentrated in vacuo. The residue was dissolved in DMF and purified by prep basic HPLC to give the title compound (140 mg, 36%) as a brown solid. LCMS (METHOD 4) (ES): m/z 545.6 [M+H]$^+$, RT=0.80 min; $^1$H NMR (400 MHZ, DMSO-d$_6$) δ 10.88 (s, 1H), 8.73 (d, J=5.1 Hz, 1H), 8.60 (s, 1H), 8.27 (d, J=8.4 Hz, 1H), 7.90 (dd, J=8.2, 1.7 Hz, 1H), 7.84-7.76 (m, 1H), 7.70 (d, J=5.2 Hz, 1H), 7.30 (d, J=2.0 Hz, 1H), 6.70 (d, J=2.0 Hz, 1H), 5.17 (hept, J=6.6 Hz, 1H), 4.68 (t, J=7.9 Hz, 1H), 1.17 (d, J=6.6 Hz, 3H), 1.13 (d, J=6.6 Hz, 3H), 0.84-0.72 (m, 1H), 0.71-0.60 (m, 1H), 0.55 (q, J=8.9 Hz, 1H), 0.33-0.23 (m, 1H), 0.21--0.11 (m, 7H).

According to the method of Preparation 3 the compound of Preparation 2 (65 mg, 0.136 mmol) was reacted with bis(pinacolato)diboron to give a crude mixture of boronic acid and boronic ester. A solution of this crude mixture and 3-bromo-2-cyclopropyl-pyridine (40 mg, 0.20 mmol) was reacted according to the method of Preparation 5 to give the title compound (26 mg, 37%) as a beige solid. LCMS (METHOD 4) (ES): m/z 517.3 [M+H]$^+$, RT=0.87 min.

Preparation 10: N-[(1S)-1-(dicyclopropylmethyl)-2-[[5-[5-(difluoromethoxy)-2-methyl-3-pyridyl]-6-fluoro-2-pyridyl]amino]-2-oxo-ethyl]-2-isopropyl-pyrazole-3-carboxamide

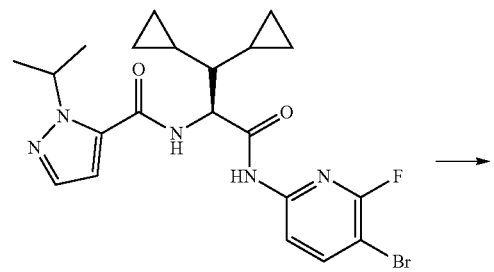

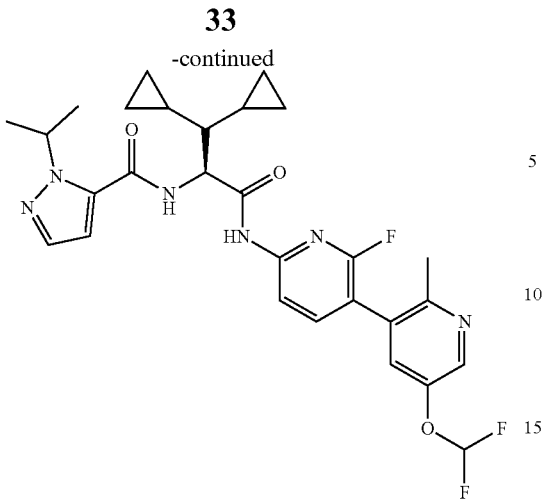

According to the method of Preparation 3 the compound of Preparation 2 (63 mg, 0.131 mmol) was reacted with bis(pinacolato)diboron to give a crude mixture of boronic acid and boronic ester. A solution of this crude mixture and 3-bromo-5-(difluoromethoxy)-2-methyl-pyridine (36 mg, 0.151 mmol) was reacted according to the method of Preparation 5 to give the title compound (43 mg, 59%) as an off-white solid. LCMS (METHOD 4) (ES): m/z 557.6 [M+H]$^+$, RT=0.79 min.

Preparation 11: benzyl N-[(1S)-1-[(5-bromo-6-fluoro-2-pyridyl)carbamoyl]-2,2-dicyclopropyl-ethyl]carbamate

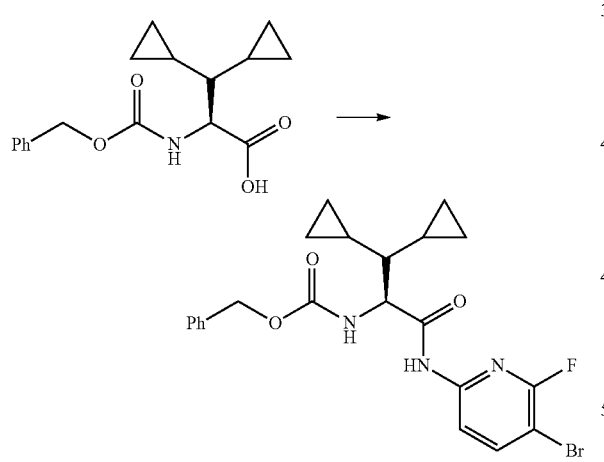

POCl$_3$ (11.1 g, 6.76 mL, 72.5 mmol) was added dropwise over 15 min to a solution of (2S)-2-(benzyloxycarbonylamino)-3,3-dicyclopropyl-propanoic acid (Preparation 349 from WO2021250194) (20.0 g, 65.9 mmol) and 5-bromo-6-fluoro-pyridin-2-amine (12.6, 65.9 mmol) in pyridine (78.2 g, 80.0 mL, 989 mmol) at 5-10° C. under N$_2$ with mechanical stirring in a 3-necked 1 L flask. The resulting orange mixture was stirred for 30 min at 5-10° C., then diluted (very slowly) with ice-water (400 mL) and stirred for 1 hour. The yellow/orange precipitate was filtered off and dried. The crude material dissolved in boiling EtOAc and precipitated by the slow addition of heptane to give the title compound (24.7 g, 79%) as a colorless solid. LCMS (METHOD 3) (ES): m/z 476.5, 478.5 [M+H]$^+$, RT=0.94 min; $^1$H NMR (400 MHZ, DMSO-d$_6$) δ 10.87 (s, 1H), 8.23 (t, J=8.9 Hz, 1H), 7.95 (dd, J=8.5, 1.4 Hz, 1H), 7.57 (d, J=8.7 Hz, 1H), 7.43-7.14 (m, 5H), 5.05 (s, 2H), 4.46 (dd, J=8.8, 6.2 Hz, 1H), 1.06-0.88 (m, 1H), 0.88-0.73 (m, 1H), 0.64-0.50 (m, 1H), 0.51-0.40 (m, 1H), 0.40-0.29 (m, 1H), 0.28-0.10 (m, 5H), 0.08-0.01 (m, 1H).

Preparation 12: 3-bromo-5-(fluoromethoxy)-2-methyl-pyridine

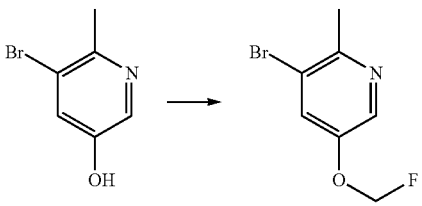

Bromo(fluoro)methane (900 mg, 8.0 mmol) was bubbled through a mixture of 5-bromo-6-methyl-pyridin-3-ol (500 mg, 2.7 mmol) and Cs$_2$CO$_3$ (1700 mg, 5.3 mmol) in dry DMF (4 mL) at room temperature in a 20 mL microwave vial until approximately 1 gram was absorbed. The vial was then capped and stirred at 60° C. for 18 hours. The resulting yellow suspension was diluted with water (50 mL), extracted with EtOAc (3×25 mL), washed with brine (20 mL), dried (Na$_2$SO$_4$) and evaporated to give the title compound (250 mg, 43%) as a yellow oil containing DMF. GCMS (ES): m/z 218.97, 220.97 [M]$^+$, RT=8.27 min; $^1$H NMR (400 MHZ, CDCl$_3$) δ 8.50-8.24 (m, 1H), 7.78-7.49 (m, 1H), 5.71 (d, J=53.7 Hz, 2H), 2.66 (s, 3H).

Preparation 13: benzyl N-[(1S)-1-(dicyclopropylmethyl)-2-[[6-fluoro-5-[5-(fluoromethoxy)-2-methyl-3-pyridyl]-2-pyridyl]amino]-2-oxo-ethyl]carbamate

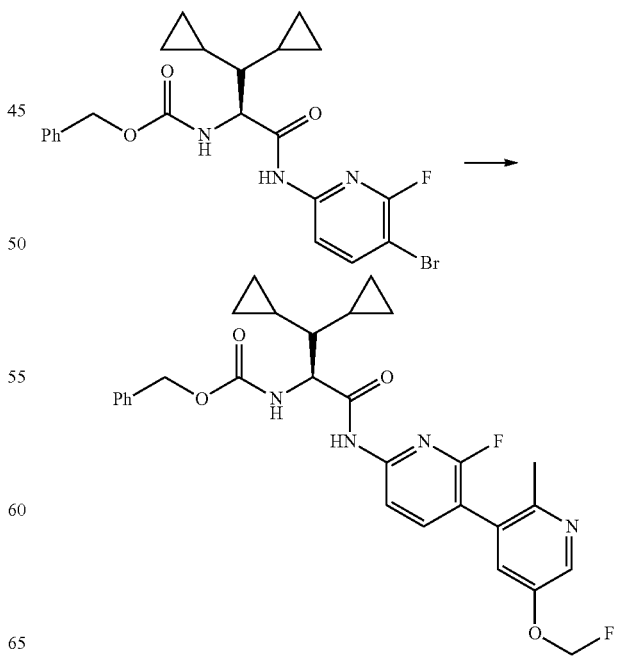

According to the method of Preparation 3 the bromo compound of Preparation 11 (475 mg, 1.00 mmol) was reacted to give a crude mixture of boronic acid and boronic ester. A solution of this crude mixture and 3-bromo-5-(fluoromethoxy)-2-methyl-pyridine, from Preparation 12, (250 mg, 1.1 mmol) was reacted according to the method of Preparation 5 to give the title compound (170 mg, 35%) as a brown solid. LCMS (METHOD 4) (ES): m/z 537.5 [M+H]$^+$, RT=0.80 min.

Preparation 14: benzyl N-[(1S)-1-(dicyclopropylmethyl)-2-[[5-(5-ethoxy-2-methyl-3-pyridyl)-6-fluoro-2-pyridyl]amino]-2-oxo-ethyl]carbamate

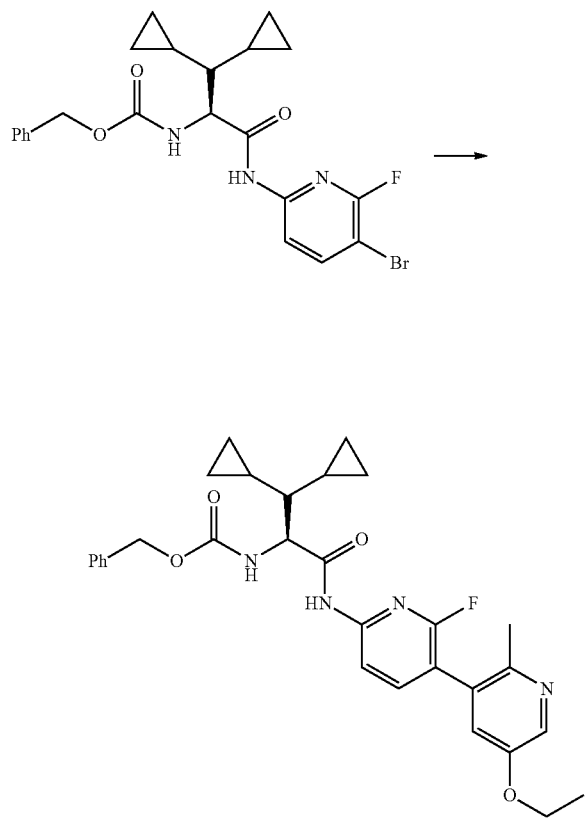

Preparation 15: N-[(1S)-1-(dicyclopropylmethyl)-2-[[6-fluoro-5-[5-(fluoromethoxy)-2-methyl-3-pyridyl]-2-pyridyl]amino]-2-oxo-ethyl]-2-isopropyl-pyrazole-3-carboxamide

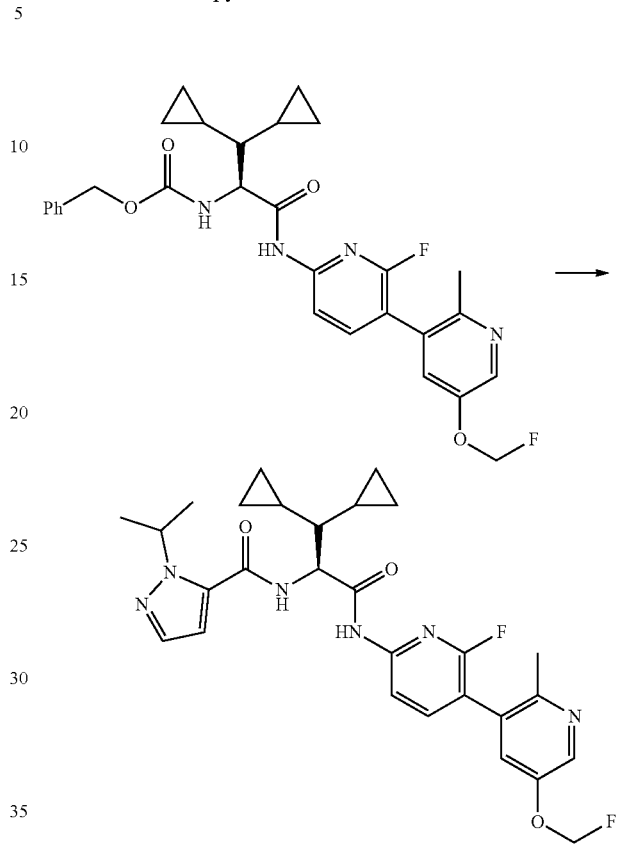

Triethylsilane (74 mg, 0.100 mL, 0.634 mmol) was added to a degassed mixture of the compound of Preparation 13 (170 mg, 0.317 mmol) and 10% Pd/C (20 mg) in MeOH (12 mL) in a capped microwave vial. The mixture was stirred for 1 hour, then filtered and evaporated to give crude (2S)-2-amino-3,3-dicyclopropyl-N-[6-fluoro-5-[5-(fluoromethoxy)-2-methyl-3-pyridyl]-2-pyridyl]propanamide as a clear oil. LCMS (METHOD 4) (ES): m/z 403.5 [M+H]$^+$, RT=0.69 min. This was taken up in dry MeCN (2 mL) and DIPEA (0.11 mL, 82 mg, 0.63 mmol) and 2-isopropylpyrazole-3-carboxylic acid (63 mg, 0.41 mmol) were added, followed by HATU (156 mg, 0.410 mmol). The mixture was stirred at room temperature for 1 hour, the solvent was evaporated, the residue was redissolved in EtOAc (20 mL), washed with sat. aq. NaHCO$_3$ (5 mL), dried (Na$_2$SO$_4$) and evaporated. The residue was purified by column chromatography (EtOAc:heptane) to give the title compound (84 mg, 49%) as a colorless solid. LCMS (METHOD 4) (ES): m/z 539.5 [M+H]$^+$, RT=0.76 min; $^1$H NMR (600 MHZ, DMSO-d$_6$) δ 11.04 (s, 1H), 8.48 (d, J=8.5 Hz, 1H), 8.38 (d, J=2.8 Hz, 1H), 8.12 (dd, J=8.2, 1.8 Hz, 1H), 8.01 (dd, J=10.1, 8.2 Hz, 1H), 7.53 (d, J=2.9 Hz, 1H), 7.51 (d, J=2.0 Hz, 1H), 6.92 (d, J=2.0 Hz, 1H), 5.93 (d, J=53.8 Hz, 2H), 5.38 (hept, J=6.6 Hz, 1H), 4.90 (t, J=8.0 Hz, 1H), 2.32 (d, J=0.9 Hz, 3H), 1.38 (d, J=6.6 Hz, 3H), 1.35 (d, J=6.7 Hz, 3H), 1.03-0.94 (m, 1H), 0.92-0.83 (m, 1H), 0.76 (td, J=9.5, 7.5 Hz, 1H), 0.54-0.45 (m, 1H), 0.43-0.35 (m, 1H), 0.36-0.19 (m, 5H), 0.19-0.12 (m, 1H).

According to the method of Preparation 3 the bromo compound of Preparation 11 (378 mg, 0.79 mmol) was reacted to give a crude mixture of boronic acid and boronic ester. A solution of this crude mixture and 3-bromo-5-ethoxy-2-methyl-pyridine, (180 mg, 0.83 mmol) was reacted according to the method of Preparation 5 to give the title compound (400 mg, 95%) as a clear oil. LCMS (METHOD 4) (ES): m/z 533.6 [M+H]$^+$, RT=0.84 min.

Preparation 16: N-[(1S)-1-(dicyclopropylmethyl)-2-[[5-(5-ethoxy-2-methyl-3-pyridyl)-6-fluoro-2-pyridyl]amino]-2-oxo-ethyl]-2-isopropyl-pyrazole-3-carboxamide

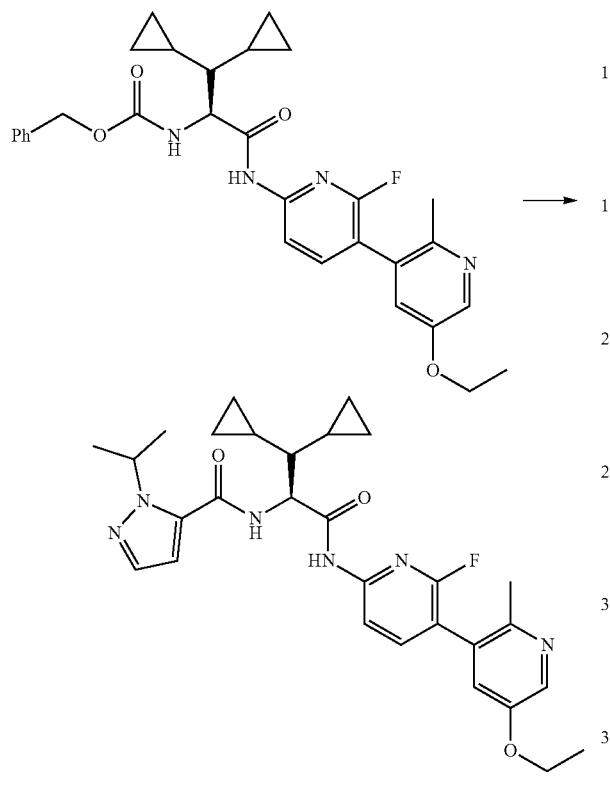

According to the method of Preparation 15, the compound of Preparation 14 (400 mg, 0.751 mmol) was reacted to give the title compound (228 mg, 57%) as a colorless solid. LCMS (METHOD 4) (ES): m/z 535.6 [M+H]⁺, RT=0.79 min; ¹H NMR (600 MHZ, DMSO-d₆) δ 10.79 (s, 1H), 8.24 (d, J=8.5 Hz, 1H), 7.99 (d, J=2.9 Hz, 1H), 7.87 (dd, J=8.2, 1.7 Hz, 1H), 7.75 (dd, J=10.1, 8.1 Hz, 1H), 7.28 (d, J=2.0 Hz, 1H), 7.07 (d, J=2.9 Hz, 1H), 6.69 (d, J=2.0 Hz, 1H), 5.16 (hept, J=6.7 Hz, 1H), 4.67 (t, J=8.0 Hz, 1H), 3.87 (q, J=7.0 Hz, 2H), 2.03 (s, 3H), 1.15 (d, J=6.6 Hz, 3H), 1.13-1.08 (m, 6H), 0.80-0.71 (m, 1H), 0.69-0.60 (m, 1H), 0.53 (td, J=9.5, 7.6 Hz, 1H), 0.31-0.22 (m, 1H), 0.20-0.13 (m, 1H), 0.12--0.04 (m, 5H), -0.04--0.11 (m, 1H).

Preparation 17: (2,3,4,5,6-pentafluorophenyl) (2S)-2-(benzyloxycarbonylamino)-3,3-dicyclopropyl-propanoate

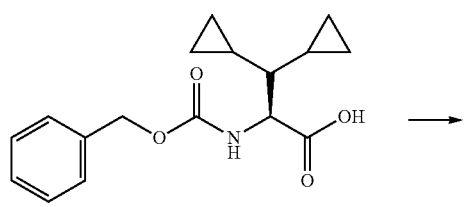

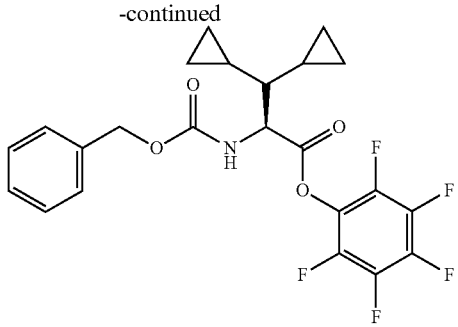

(2,3,4,5,6-Pentafluorophenyl) 2,2,2-trifluoroacetate (4.15 g, 14.8 mmol) was added to a solution of (2S)-2-(benzyloxycarbonylamino)-3,3-dicyclopropyl-propanoic acid (Preparation 349 from WO2021250194) (3.0 g, 9.89 mmol) and pyridine (2.4 mL, 29.7 mmol) in DCM (30 mL) at room temperature, and the reaction mixture was stirred for 16 hours. The reaction mixture was diluted with H₂O (50 mL) and extracted with DCM (3×30 mL). The combined organic phase was dried over MgSO₄, filtered, and concentrated in vacuo. The obtained crude compound was purified by column chromatography (eluting with EtOAc in hexane) to afford the title compound (3.50 g, 57% yield). LCMS (METHOD 2) (ESI): m/z 470.3 [M+H]⁺, RT=2.30 min. (Acquity BEH C18 (50 mm×2.1 mm), 0.05% formic acid in MeCN, 0.05% formic acid in H₂O).

Preparation 18: 5-bromo-6-fluoro-pyridin-2-amine

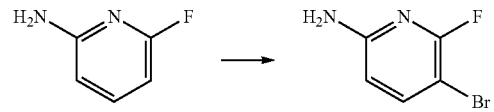 [SMILES: Nc1cccc(F)n1 ; Nc1ccc(Br)c(F)n1]

NBS (30.5 g, 171 mmol) was added portion-wise to a solution of 6-fluoropyridin-2-amine (19.2 g, 171 mmol) in MeCN (130 mL) at 10° C. On complete addition the reaction mixture was stirred for a further 15 minutes at room temperature. The reaction mixture was concentrated under reduced pressure, diluted with H₂O (200 mL) and extracted with Et₂O (2×250 mL). The combined organic layers were filtered through a small silica gel plug, dried over Na₂SO₄, filtered, and concentrated in vacuo. The residue was re-dissolved in hot EtOAc (50 mL) and treated with activated charcoal. The charcoal was filtered off, and the solution was heated and diluted with heptane (180 mL). On cooling the title compound crystallized and was isolated (29.1 g, 89% yield) as a colorless solid. LCMS (METHOD 3) (ES): m/z 191.0 [M+H]⁺, RT=0.56 min; ¹H NMR (400 MHZ, CDCl₃) δ 7.60 (t, J=8.6 Hz, 1H), 6.26 (dd, J=8.4, 1.4 Hz, 1H), 4.57 (s, 2H).

Preparation 19: 6-fluoro-5-(4,4,5,5-tetramethyl-1,3,2-dioxaborolan-2-yl)pyridin-2-amine

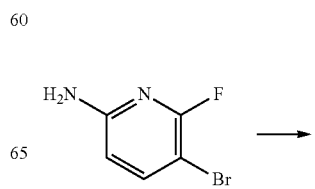

-continued

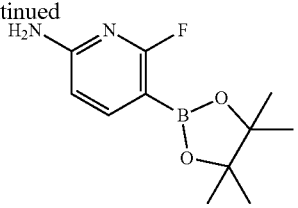

KOAc (3.78 g, 38.5 mmol) was added to a solution of the product from Preparation 18 (3.68 g, 19.3 mmol) and 4,4,5,5-tetramethyl-2-(4,4,5,5-tetramethyl-1,3,2-dioxaborolan-2-yl)-1,3,2-dioxaborolane (7.34 g, 28.9 mmol) in 1,4-dioxane (40 mL). The reaction mixture was degassed and purged with nitrogen for 10 minutes. Pd(dppf)Cl$_2$ (0.7 g, 0.96 mmol) was added, and the reaction mixture was stirred at 100° C. for 18 hours under nitrogen. The cooled reaction mixture was concentrated in vacuo to low volume and diluted with EtOAc (150 mL). The organic phase was washed with H$_2$O (2×40 mL), dried over Na$_2$SO$_4$ and concentrated in vacuo. The obtained crude compound was slurried in heptane (50 mL) for 30 minutes, filtered, and dried in vacuo to afford the title compound (3.70 g, 81% yield) as an off-white solid. LCMS (METHOD 4) (ES): m/z 239.3 [M+H]$^+$, RT=0.58 min.

Preparation 20: 5-(5-chloro-2-methyl-3-pyridyl)-6-fluoro-pyridin-2-amine

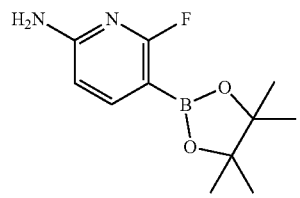

→

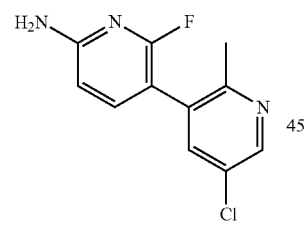

K$_3$PO$_4$ (1.75 g, 8.23 mmol) was added to a solution of the compound of Preparation 19 (1.0 g, 4.12 mmol) and 3-bromo-5-chloro-2-methylpyridine (0.85 g, 4.12 mmol) in 1,4-dioxane (10 mL) and H$_2$O (3 mL). The reaction mixture was thoroughly degassed and purged with nitrogen for 15 minutes. Pd(dppf)Cl$_2$·DCM (336 mg, 0.41 mmol) was added and the sealed reaction mixture was stirred under microwave conditions at 120° C. for 1.5 hours. The cooled reaction mixture was filtered through Celite™ and washed with EtOAc (40 mL). The reaction mixture was washed with brine solution (10 mL), dried over Na$_2$SO$_4$, filtered, and concentrated in vacuo. The obtained crude compound was purified by column chromatography (eluting with EtOAc in hexane) to afford the title compound (700 mg, 52% yield). LCMS (METHOD 2) (ESI): m/z 238.4 [M+H]$^+$, RT=1.46 min. (Acquity BEH C18 (50 mm×2.1 mm), 0.05% formic acid in MeCN, 0.05% formic acid in H$_2$O).

Preparation 21: benzyl N-[(1S)-1-[[5-(5-chloro-2-methyl-3-pyridyl)-6-fluoro-2-pyridyl]carbamoyl]-2,2-dicyclopropyl-ethyl]carbamate

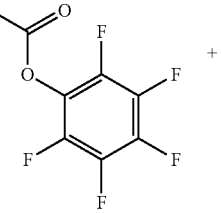

+

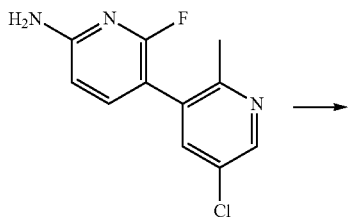

→

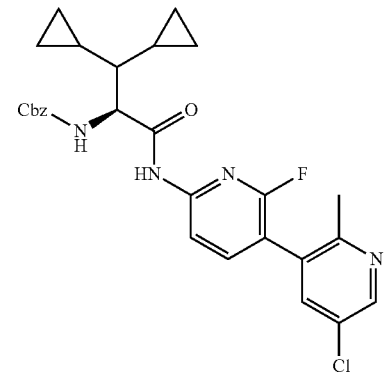

Tert-butylmagnesium chloride (1.0 M in THF, 2.76 mL) was added to a solution of the compound of Preparation 20 (600 mg, 1.84 mmol) in THF (7 mL) at 0° ° C. The reaction mixture was stirred for 10 minutes. The compound of Preparation 17 (865 mg, 1.84 mmol) was added, and the reaction mixture was stirred for 2 hours at room temperature. The reaction mixture was quenched with saturated aq. NH$_4$Cl (10 mL) and extracted with EtOAc (2×20 mL). The combined organic phase was washed with brine solution (10 mL), dried over Na$_2$SO$_4$, filtered, and concentrated in vacuo. The obtained crude compound was purified by column chromatography (eluting with EtOAc in hexane) to afford the title compound (700 mg, 68% yield). LCMS (METHOD 2) (ESI): m/z 523.4 [M+H]$^+$, RT=2.49 min. (Acquity BEH C18 (50 mm×2.1 mm), 0.05% formic acid in MeCN, 0.05% formic acid in H$_2$O).

Preparation 22: benzyl N-[(1S)-1-[[5-(5-chloro-2-methyl-1-oxido-pyridin-1-ium-3-yl)-6-fluoro-2-pyridyl]carbamoyl]-2,2-dicyclopropyl-ethyl]carbamate

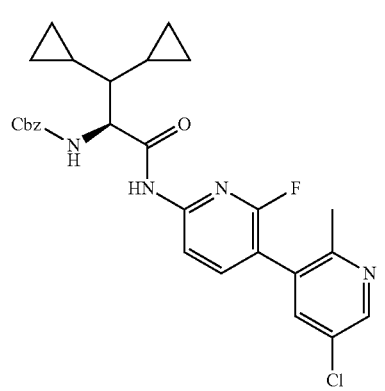

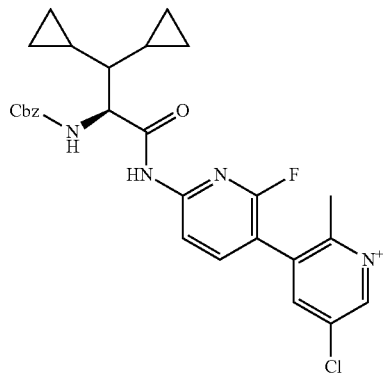

mCPBA (278 mg, 1.62 mmol) was added to a solution of the compound of Preparation 21 (600 mg, 1.08 mmol) in DCM (7 mL) at 0° C. On complete addition the reaction was stirred for 2 hours at room temperature. The reaction mixture was quenched with aq. NaHCO$_3$ (10 mL) and extracted with DCM (2×50 mL). The combined organic phase was dried over Na$_2$SO$_4$, filtered, and concentrated in vacuo to afford the crude title compound (490 mg, 76% yield), that was used without further purification. LCMS (METHOD 2) (ESI): m/z 539.4 [M+H]$^+$, RT=1.94 min. (Acquity BEH C18 (50 mm×2.1 mm), 0.05% formic acid in MeCN, 0.05% formic acid in H$_2$O).

Preparation 23: (2S)-2-amino-N-[5-(5-chloro-2-methyl-1-oxido-pyridin-1-ium-3-yl)-6-fluoro-2-pyridyl]-3,3-dicyclopropyl-propanamide

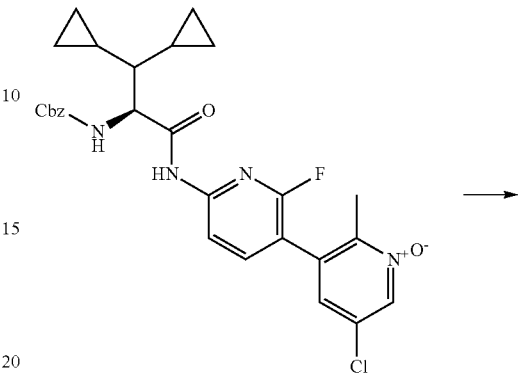

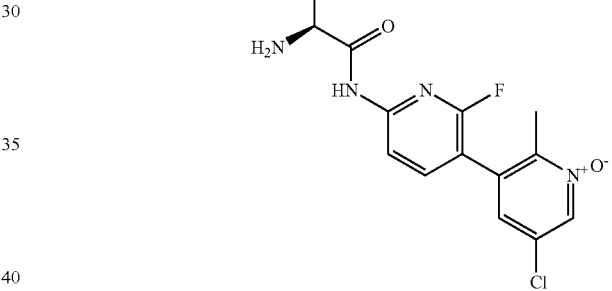

Hydrogen bromide (47% aqueous solution, 0.4 mL) was added to a solution of the compound of Preparation 22 (500 mg, 9.27 mmol) in DCM (5 mL) at 0° C. The reaction was slowly warmed to room temperature then stirred at 50° C. for 2 hours. The cooled reaction mixture was concentrated in vacuo then azeotroped with toluene and dried in vacuo to leave the crude title compound (300 mg, impurities visible, no yield calculated) that was used without further purification. LCMS (METHOD 2) (ESI): m/z 405.4 [M+H]$^+$, RT=1.69 min. (YMC TRIART C18 50 mm×2.1 mm, 1.9 μm), 0.05% TFA in MeCN, 0.05% TFA in H$_2$O).

Preparation 24: 6-fluoro-5-[2-methyl-5-(trifluoromethyl)-3-pyridyl]pyridin-2-amine

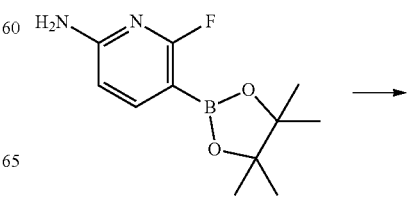

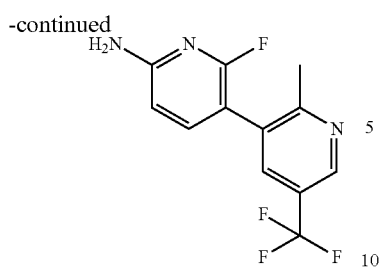

According to the method of Preparation 20 the compound of Preparation 19 (397 mg, 1.67 mmol) was reacted with 3-bromo-2-methyl-5-(trifluoromethyl)pyridine (400 mg, 1.67 mmol) to afford the title compound (250 mg, 55% yield) after purification by column chromatography (eluting with EtOAc in pet. ether). LCMS (METHOD 2) (ESI): m/z 272.4 [M+H]$^+$, RT=1.69 min. (YMC TRIART C18 50 mm×2.1 mm, 1.9 μm), 0.05% formic acid in MeCN, 0.05% formic acid in H$_2$O).

Preparation 25: benzyl N-[(1S)-1-(dicyclopropylmethyl)-2-[[6-fluoro-5-[2-methyl-5-(trifluoromethyl)-3-pyridyl]-2-pyridyl]amino]-2-oxo-ethyl]carbamate the title compound (310 mg, 60% yield) after purification by column chromatography (eluting with EtOAc in hexane). LCMS (METHOD 2) (ESI): m/z 557.6 [M+H]$^+$, RT=2.16 min. (YMC TRIART C18 50 mm×2.1 mm, 1.9 μm), 0.05% formic acid in MeCN, 0.05% formic acid in H$_2$O).

Preparation 26: (2S)-2-amino-3,3-dicyclopropyl-N-[6-fluoro-5-[2-methyl-5-(trifluoromethyl)-3-pyridyl]-2-pyridyl]propenamide

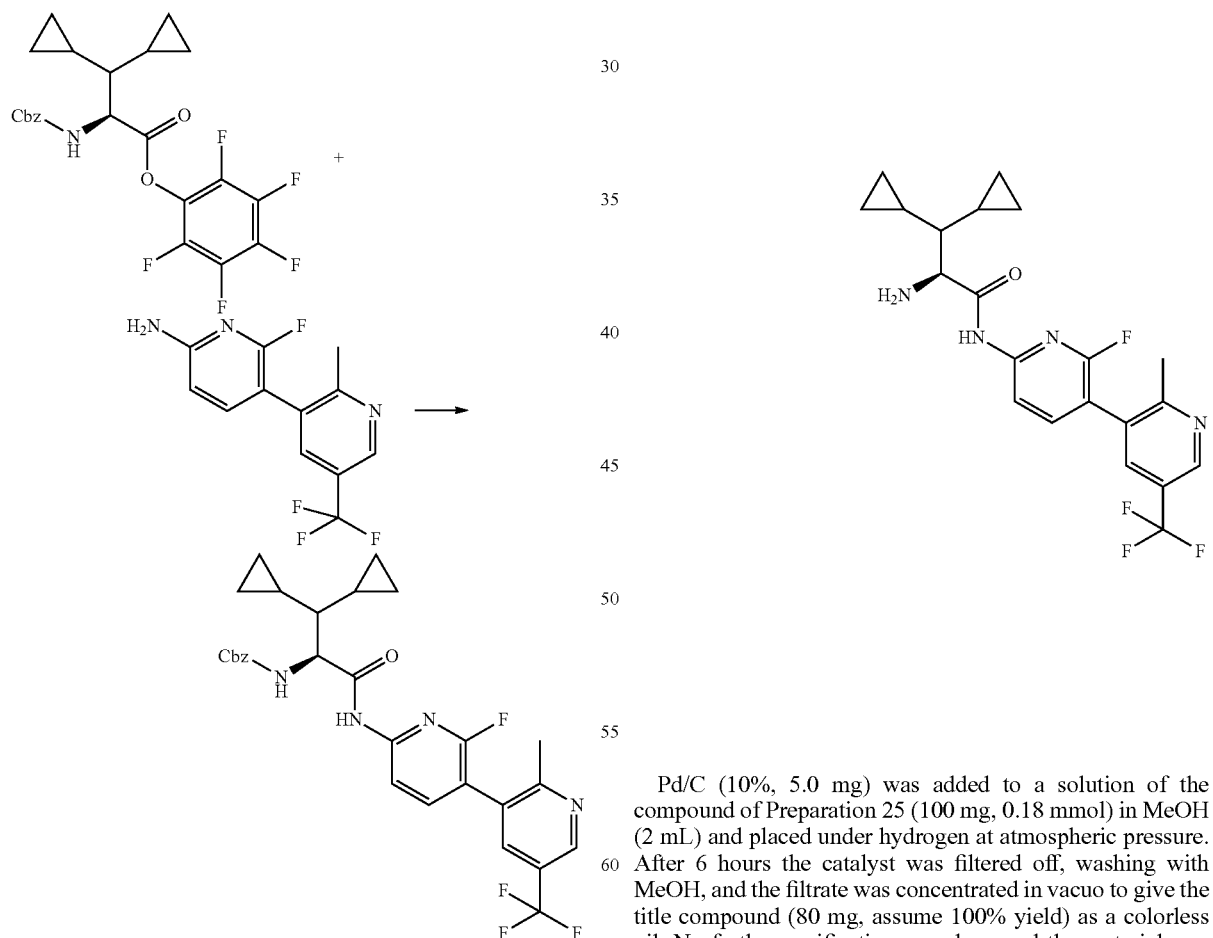

According to the method of Preparation 21 the compound of Preparation 24 (250 mg, 0.92 mmol) was reacted with the compound of Preparation 17 (432 mg, 0.92 mmol) to afford Pd/C (10%, 5.0 mg) was added to a solution of the compound of Preparation 25 (100 mg, 0.18 mmol) in MeOH (2 mL) and placed under hydrogen at atmospheric pressure. After 6 hours the catalyst was filtered off, washing with MeOH, and the filtrate was concentrated in vacuo to give the title compound (80 mg, assume 100% yield) as a colorless oil. No further purification was done and the material was used directly in the next step. LCMS (METHOD 2) (ESI): m/z 423.5 [M+H]$^+$, RT=1.82 min. (Acquity BEH C18 (50 mm×2.1 mm), 0.05% formic acid in MeCN, 0.05% formic acid in H$_2$O).

Preparation 27: N-[(1S)-1-(dicyclopropylmethyl)-2-[[6-fluoro-5-[2-methyl-5-(trifluoromethyl)-3-pyridyl]-2-pyridyl]amino]-2-oxo-ethyl]-2-isopropyl-pyrazole-3-carboxamide

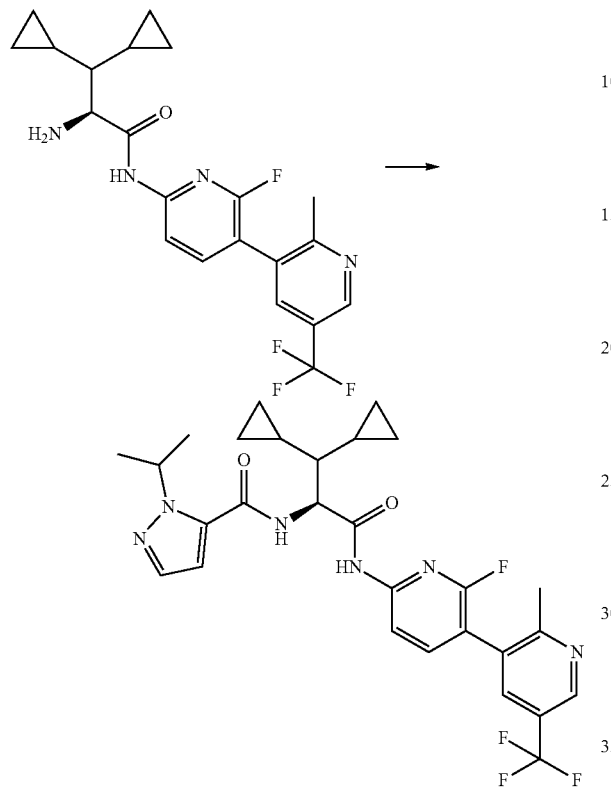

HATU (153 mg, 0.40 mmol) was added to a solution of the compound of Preparation 26 (113 mg, 0.27 mmol), 2-isopropylpyrazole-3-carboxylic acid (41.2 mg, 0.27 mmol) and DIPEA (0.14 mL, 0.80 mmol) in DMF (5 mL) at 0° C. The reaction mixture was stirred and allowed to warm to room temperature over 6 hours. The reaction mixture was quenched with ice/H$_2$O (50 mL) and extracted with DCM (2×100 mL). The combined organic phase was dried over Na$_2$SO$_4$, filtered, and concentrated in vacuo. The obtained crude compound was purified by column chromatography (eluting with EtOAc in hexane) to afford the title compound (149 mg, assume 100% yield) as a colorless oil. LCMS (METHOD 2) (ESI): m/z 559.5 [M+H]$^+$, RT=2.41 min. (Acquity BEH C18 (50 mm×2.1 mm), 0.05% formic acid in MeCN, 0.05% formic acid in H$_2$O)

Preparation 28: 3-bromo-2-cyclopropyl-5-methyl-pyridine

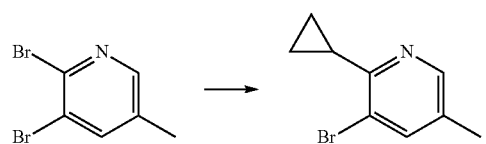

K$_3$PO$_4$ (6.30 g, 30.0 mmol) was added to a solution of 2,3-dibromo-5-methylpyridine (2.50 g, 10.0 mmol), cyclopropylboronic acid (0.86 g, 10.0 mmol), triphenyl phosphine (0.52 g, 2.0 mmol) in MeCN (5 mL) and MeOH (2.5 mL). The reaction mixture was thoroughly degassed and purged with nitrogen for 15 minutes. Pd(OAc)$_2$ (224 mg, 1.0 mmol) was added and the reaction mixture was stirred at 100° C. for 16 hours. The reaction mixture was quenched with H$_2$O (50 mL) and extracted with EtOAc (3×100 mL). The combined organic phase was dried over Na$_2$SO$_4$, filtered, and concentrated in vacuo. The obtained crude compound was purified by column chromatography (eluting with EtOAc in hexane) to afford the title compound (1.3 g, 62% yield). LCMS (METHOD 2) (ESI): m/z 214.3 [M+H]$^+$, RT=2.06 min. (YMC TRIART C18 50 mm×2.1 mm, 1.9 µm), 0.05% formic acid in MeCN, 0.05% formic acid in H$_2$O).

Preparation 29: 5-(2-cyclopropyl-5-methyl-3-pyridyl)-6-fluoro-pyridin-2-amine

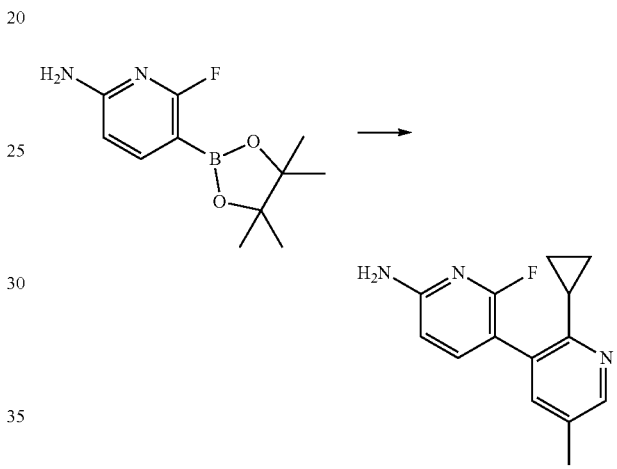

According to the method of Preparation 20 the compound of Preparation 19 (1.00 g, 4.20 mmol) was reacted with the compound of Preparation 28 (0.89 g, 4.20 mmol) to afford the title compound (600 mg, 59% yield) after purification by column chromatography (eluting with EtOAc in hexane). LCMS (METHOD 2) (ESI): m/z 244.2 [M+H]$^+$, RT=1.23 min. (YMC TRIART C18 50 mm×2.1 mm, 1.9 µm), 0.05% formic acid in MeCN, 0.05% formic acid in H$_2$O).

Preparation 30: benzyl N-[(1S)-2,2-dicyclopropyl-1-[[5-(2-cyclopropyl-5-methyl-3-pyridyl)-6-fluoro-2-pyridyl]carbamoyl]ethyl]carbamate

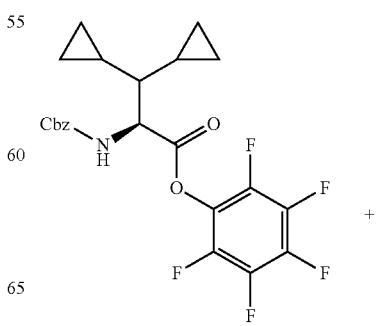

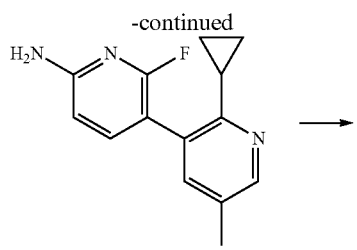

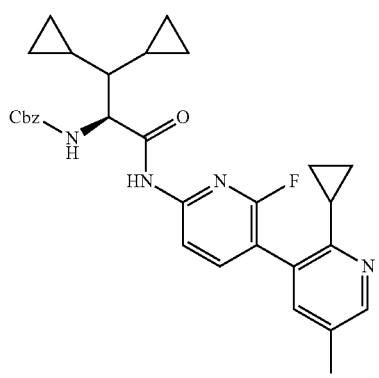

According to the method of Preparation 21 the compound of Preparation 29 (600 mg, 2.47 mmol) was reacted with the compound of Preparation 17 (1.16 g, 2.47 mmol) to afford the title compound (800 mg, 61% yield) after purification by column chromatography (eluting with EtOAc in hexane). LCMS (METHOD 2) (ESI): m/z 529.5 [M+H]+, RT=2.06 min. (YMC TRIART C18 50 mm×2.1 mm, 1.9 μm), 0.05% formic acid in MeCN, 0.05% formic acid in H2O).

Preparation 31: (2S)-2-amino-3,3-dicyclopropyl-N-[5-(2-cyclopropyl-5-methyl-3-pyridyl)-6-fluoro-2-pyridyl]propenamide

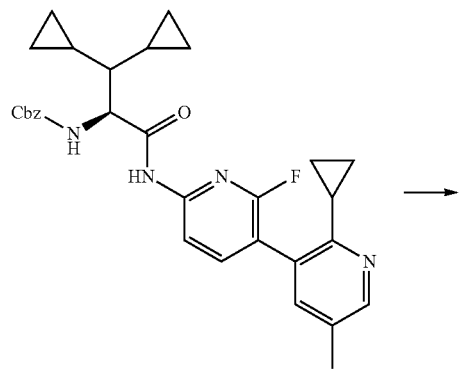

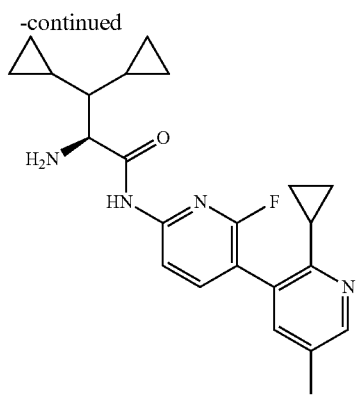

According to the method of Preparation 26 the compound of Preparation 30 (100 mg, 0.19 mmol) was reacted in THF/EtOAc to afford the title compound (80 mg, 62% yield). LCMS (METHOD 2) (ESI): m/z 395.4 [M+H]+, RT=1.71 min. (Acquity BEH C18 (50 mm×2.1 mm), 0.05% formic acid in MeCN, 0.05% formic acid in H2O).

Preparation 32: N-[(1S)-2,2-dicyclopropyl-1-[[5-(2-cyclopropyl-5-methyl-3-pyridyl)-6-fluoro-2-pyridyl]carbamoyl]ethyl]-2-isopropyl-pyrazole-3-carboxamide According to the method of Preparation 27 the compound of Preparation 31 (70.0 mg, 0.18 mmol) was reacted with 2-isopropylpyrazole-3-carboxylic acid (27.4 mg, 0.18 mmol) to afford the title compound (90 mg, 82% yield) after purification by column chromatography (eluting with EtOAc in hexane). LCMS (METHOD 2) (ESI): m/z 531.5

[M+H]+, RT=1.97 min. (YMC TRIART C18 50 mm×2.1 mm, 1.9 μm), 0.05% formic acid in MeCN, 0.05% formic acid in H₂O).

Preparation 33: 3-bromo-5-cyclopropyl-2-methyl-pyridine and 5-bromo-3-cyclopropyl-2-methyl-pyridine

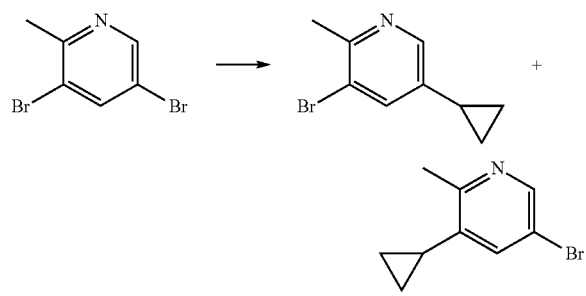

K₃PO₄ (6.30 g, 30.0 mmol) was added to a solution of 3,5-dibromo-2-methylpyridine (2.50 g, 10.0 mmol) and cyclopropylboronic acid (0.86 g, 10.0 mmol) in toluene (15 mL). The reaction mixture was thoroughly degassed and purged with nitrogen for 15 minutes. Pd(dppf)Cl₂·DCM (0.73 g, 1.0 mmol) was added and the reaction mixture was stirred at 100° C. for 1 hour. The reaction mixture was quenched with H₂O (50 mL) and extracted with EtOAc (3×100 mL). The combined organic phase was dried over Na₂SO₄, filtered, and concentrated in vacuo. The obtained crude compound was purified by column chromatography (eluting with EtOAc in hexane), to afford the title compounds (900 mg, 43% yield) as a mix of regioisomers. LCMS (METHOD 2) (ESI): m/z 214.1 [M+H]+, RT=1.76 and 2.02 min. (YMC TRIART C18 50 mm×2.1 mm, 1.9 μm), 0.05% formic acid in MeCN, 0.05% formic acid in H₂O).

Preparation 34: 5-(5-cyclopropyl-2-methyl-3-pyridyl)-6-fluoro-pyridin-2-amine and 5-(5-cyclopropyl-6-methyl-3-pyridyl)-6-fluoro-pyridin-2-amine

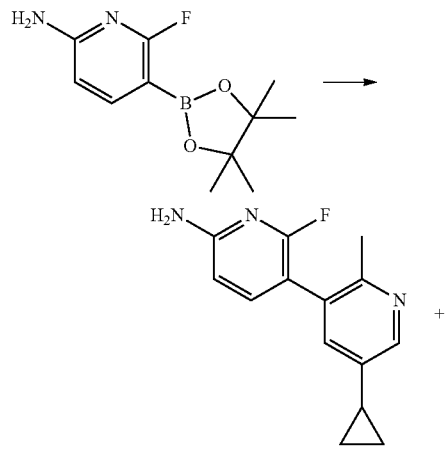

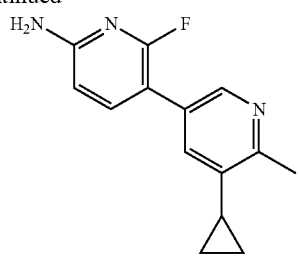

According to the method of Preparation 20 the compound of Preparation 19 (500 mg, 2.10 mmol) was reacted with the compounds of Preparation 33 (445 mg, 2.10 mmol) to afford the title compounds (350 mg, 68% yield) after purification by column chromatography (eluting with EtOAc in hexane). LCMS (METHOD 2) (ESI): m/z 244.5 [M+H]+, RT=3.86 and 4.13 min. (Acquity BEH C18 (50 mm×2.1 mm), 0.05% formic acid in MeCN, 0.05% formic acid in H₂O).

Preparation 35: benzyl N-[(1S)-2,2-dicyclopropyl-1-[[5-(5-cyclopropyl-2-methyl-3-pyridyl)-6-fluoro-2-pyridyl]carbamoyl]ethyl]carbamate and benzyl N-[(1S)-2,2-dicyclopropyl-1-[[5-(5-cyclopropyl-6-methyl-3-pyridyl)-6-fluoro-2-pyridyl]carbamoyl]ethyl]carbamate

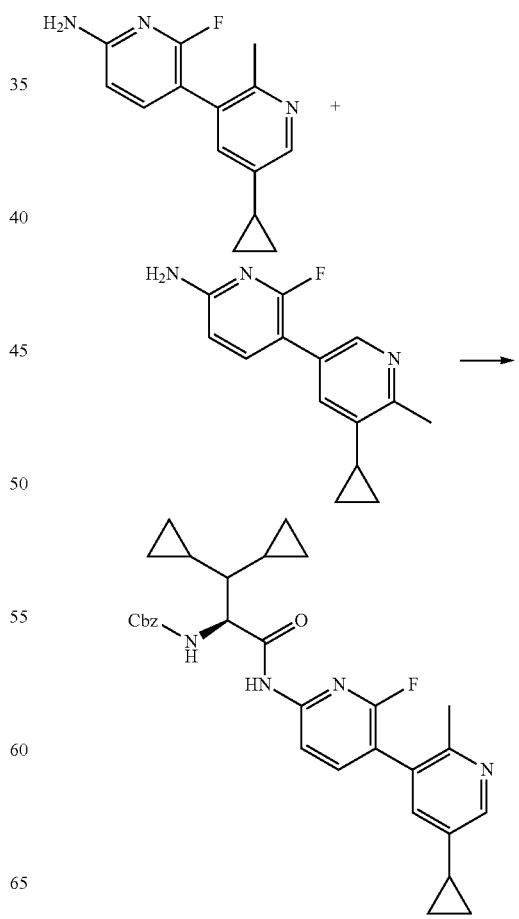

-continued

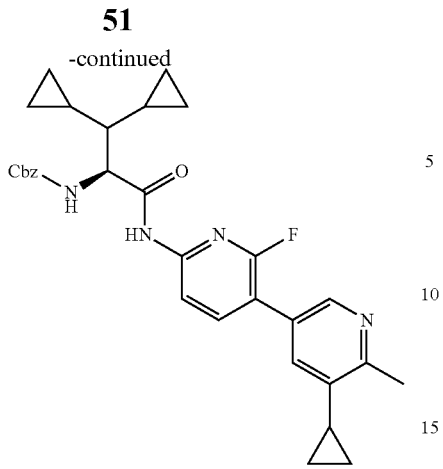

According to the method of Preparation 21 the compounds of Preparation 34 (340 mg, 1.40 mmol) were reacted with the compound of Preparation 17 (655 mg, 1.40 mmol) to afford the title compounds (450 mg, 60% yield) after purification by column chromatography (eluting with EtOAc in hexane). LCMS (METHOD 2) (ESI): m/z 529.5 [M+H]$^+$, RT=2.16 min. (YMC TRIART C18 50 mm×2.1 mm, 1.9 μm), 0.05% formic acid in MeCN, 0.05% formic acid in H$_2$O).

Preparation 36: (2S)-2-amino-3,3-dicyclopropyl-N-[5-(5-cyclopropyl-2-methyl-3-pyridyl)-6-fluoro-2-pyridyl]propenamide and (2S)-2-amino-3,3-dicyclopropyl-N-[5-(5-cyclopropyl-6-methyl-3-pyridyl)-6-fluoro-2-pyridyl]propenamide

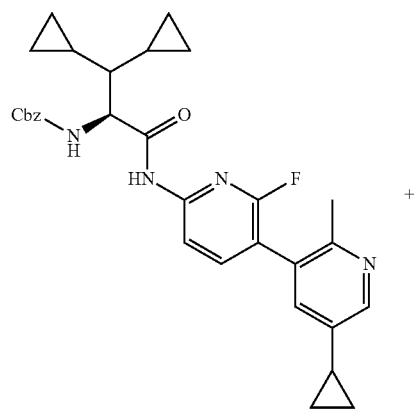

-continued

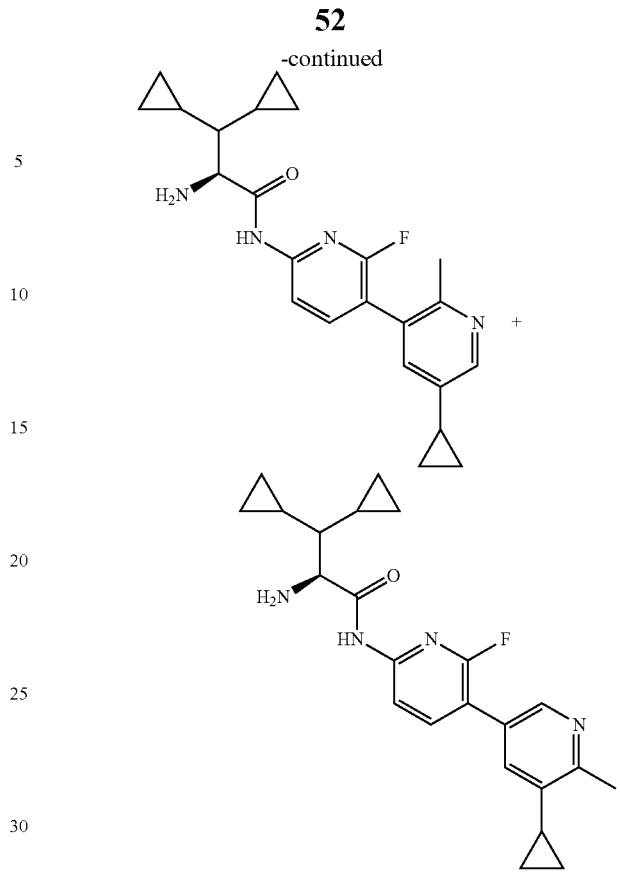

According to the method of Preparation 26 the compounds of Preparation 35 (440 mg, 0.83 mmol) were reacted in THF/EtOAc to afford the title compounds (320 mg, 97% yield). LCMS (METHOD 2) (ESI): m/z 395.5 [M+H]$^+$, RT=1.26 and 1.30 min. (YMC TRIART C18 50 mm×2.1 mm, 1.9 μm), 0.05% formic acid in MeCN, 0.05% formic acid in H$_2$O).

Preparation 37: N-[(1S)-2,2-dicyclopropyl-1-[[5-(5-cyclopropyl-2-methyl-3-pyridyl)-6-fluoro-2-pyridyl]carbamoyl]ethyl]-2-isopropyl-pyrazole-3-carboxamide and N-[(1S)-2,2-dicyclopropyl-1-[[5-(5-cyclopropyl-6-methyl-3-pyridyl)-6-fluoro-2-pyridyl]carbamoyl]ethyl]-2-isopropyl-pyrazole-3-carboxamide

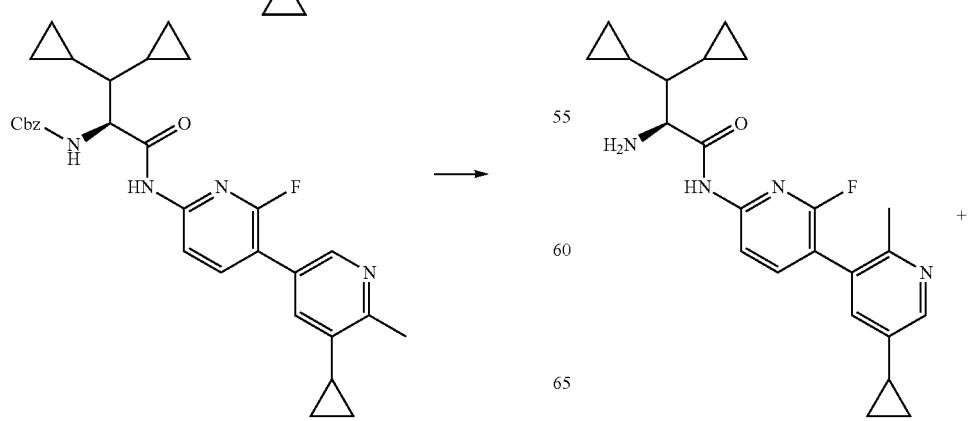

-continued

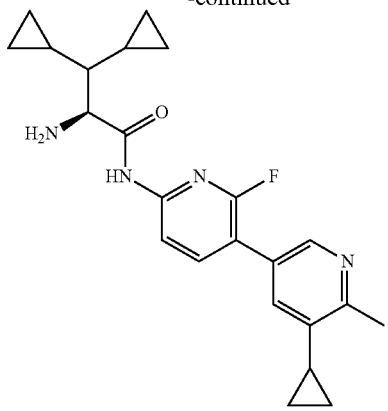

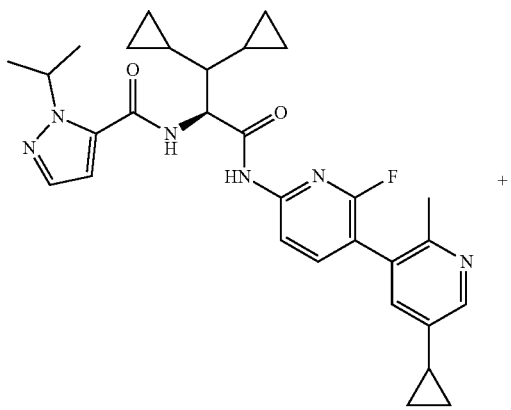

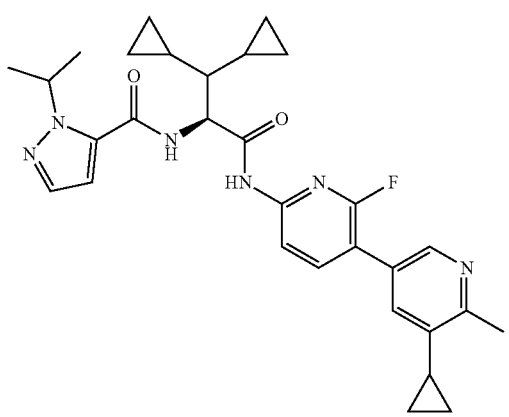

According to the method of Preparation 27 the compounds of Preparation 36 (310 mg, 0.79 mmol) were reacted with 2-isopropylpyrazole-3-carboxylic acid (121 mg, 0.79 mmol) to afford the title compounds (292 mg, 70% yield) after purification by column chromatography (eluting with EtOAc in hexane). LCMS (METHOD 2) (ESI): m/z 531.7 [M+H]+, RT=1.75 and 1.78 min. (YMC TRIART C18 50 mm×2.1 mm, 1.9 μm), 0.05% formic acid in MeCN, 0.05% formic acid in H$_2$O).

Preparation 38: benzyl N-[(1S)-1-(dicyclopropylmethyl)-2-[[6-fluoro-5-(4-methyl-3-pyridyl)-2-pyridyl]amino]-2-oxo-ethyl]carbamate

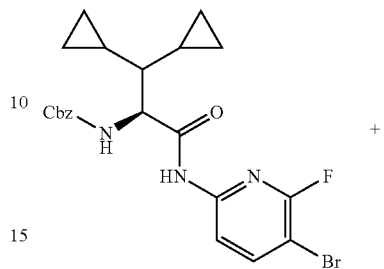

+

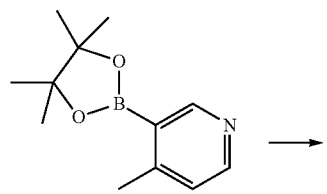

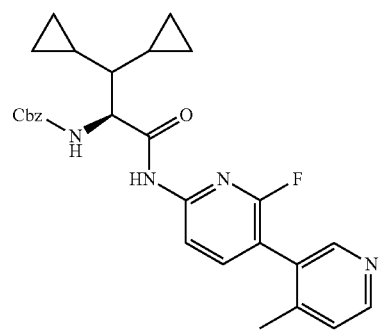

K$_3$PO$_4$ (804 mg, 3.78 mmol) was added to a solution of the compound of Preparation 11 (600 mg, 1.26 mmol) and 4-methyl-3-(4,4,5,5-tetramethyl-1,3,2-dioxaborolan-2-yl)pyridine (414 mg, 1.89 mmol) in 1,4-dioxane (10 mL) and H$_2$O (1 mL) in a microwave vial. The reaction mixture was thoroughly degassed and purged with nitrogen for 15 minutes. Pd(dppf)Cl$_2$·DCM (103 mg, 0.13 mmol) was added and the sealed reaction mixture was stirred at 120° C. for 2 hours. The cooled reaction mixture was filtered through Celite™ and washed with DCM (40 mL) and concentrated in vacuo. The obtained crude compound was purified by column chromatography (eluting with EtOAc in pet. ether) to afford the title compound (400 mg, 65% yield) as an off-white solid. LCMS (METHOD 2) (ESI): m/z 489.4 [M+H]+, RT=1.93 min. (Acquity BEH C18 (50 mm×2.1 mm), MeCN, H$_2$O).

Preparation 39: benzyl N-[(1S)-1-(dicyclopropylm-ethyl)-2-[[6-fluoro-5-(4-methyl-1-oxido-pyridin-1-ium-3-yl)-2-pyridyl]amino]-2-oxo-ethyl]carbamate

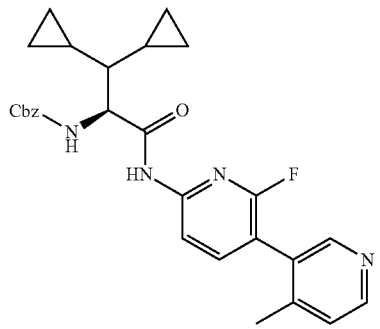

According to the method of Preparation 22 the compound of Preparation 38 (450 mg, 0.92 mmol) was reacted to afford the title compound (170 mg, 36% yield) as an off-white solid. LCMS (METHOD 2) (ESI): m/z 505.4 [M+H]⁺, RT=1.92 min. (Acquity BEH C18 (50 mm×2.1 mm), 0.05% formic acid in MeCN, 0.05% formic acid in H$_2$O).

Preparation 40: (2S)-2-amino-3,3-dicyclopropyl-N-[6-fluoro-5-(4-methyl-1-oxido-pyridin-1-ium-3-yl)-2-pyridyl]propenamide

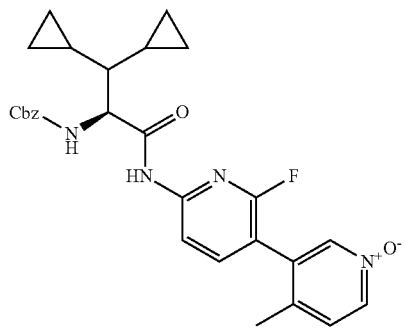

According to the method of Preparation 23 the compound of Preparation 39 (170 mg, 0.34 mmol) was reacted to afford the title compound as a tacky solid (98 mg, 79% yield). LCMS (METHOD 2) (ESI): m/z 371.5 [M+H]⁺, RT=1.23 min. (Acquity BEH C18 (50 mm×2.1 mm), 0.05% formic acid in MeCN, 0.05% formic acid in H$_2$O).

Preparation 41: benzyl N-[(1S)-1-(dicyclopropylm-ethyl)-2-[[6-fluoro-5-(2-methyl-3-pyridyl)-2-pyridyl]amino]-2-oxo-ethyl]carbamate

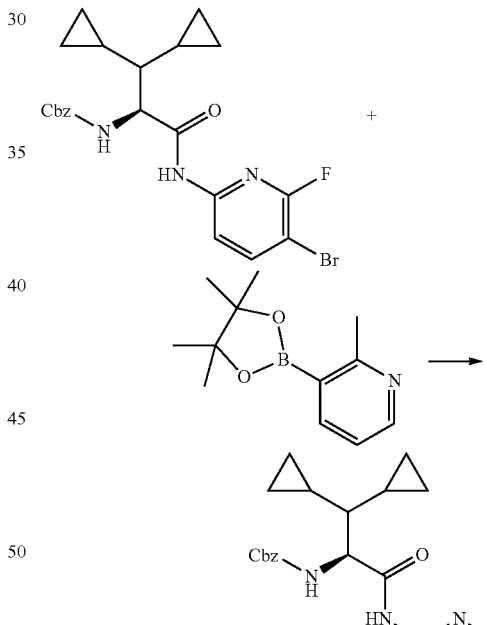

According to the method of Preparation 38 the compound of Preparation 11 (250 mg, 0.52 mmol) was reacted with 2-methyl-3-(4,4,5,5-tetramethyl-1,3,2-dioxaborolan-2-yl)pyridine (230 mg, 1.05 mmol) to afford the title compound (150 mg, 58% yield) as an off-white solid. LCMS (METHOD 2) (ESI): m/z 489.4 [M+H]⁺, RT=1.89 min. (Acquity BEH C18 (50 mm×2.1 mm), MeCN, H$_2$O).

Preparation 42: benzyl N-[(1S)-1-(dicyclopropylmethyl)-2-[[6-fluoro-5-(2-methyl-1-oxido-pyridin-1-ium-3-yl)-2-pyridyl]amino]-2-oxo-ethyl]carbamate

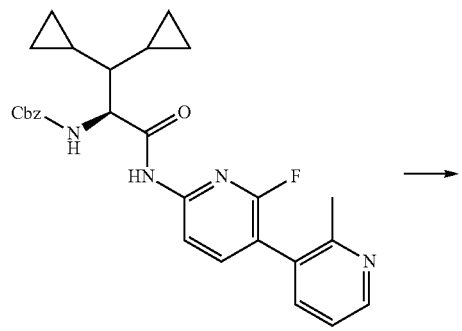

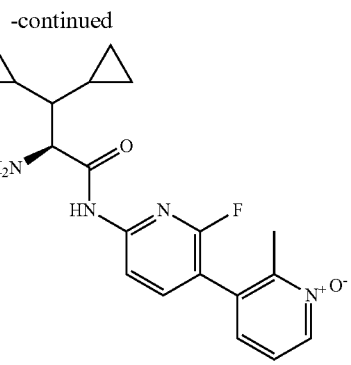

According to the method of Preparation 23 the compound of Preparation 42 (160 mg, 0.32 mmol) was reacted to afford the title compound as a tacky solid (107 mg, 91% yield). LCMS (METHOD 2) (ESI): m/z 371.4 [M+H]$^+$, RT=1.53 min. (Acquity BEH C18 (50 mm×2.1 mm), 0.05% formic acid in MeCN, 0.05% formic acid in H$_2$O).

Preparation 44: (2S)-2-amino-N-(5-bromo-6-chloro-2-pyridyl)-3,3-dicyclopropyl-propanamide hydrochloride salt

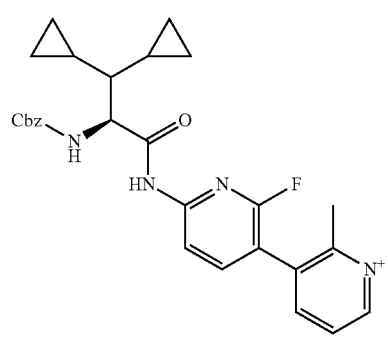

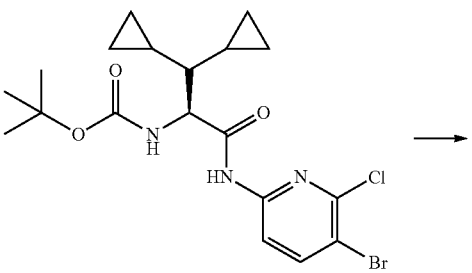

According to the method of Preparation 22 the compound of Preparation 41 (400 mg, 0.82 mmol) was reacted to afford the title compound (180 mg, 43% yield) as an off-white solid. LCMS (METHOD 2) (ESI): m/z 505.3 [M+H]$^+$, RT=1.93 min. (Acquity BEH C18 (50 mm×2.1 mm), 0.05% formic acid in MeCN, 0.05% formic acid in H$_2$O).

Preparation 43: (2S)-2-amino-3,3-dicyclopropyl-N-[6-fluoro-5-(2-methyl-1-oxido-pyridin-1-ium-3-yl)-2-pyridyl]propenamide

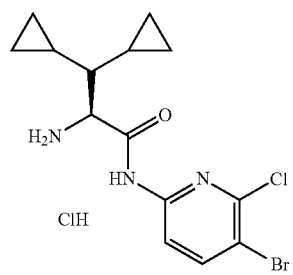

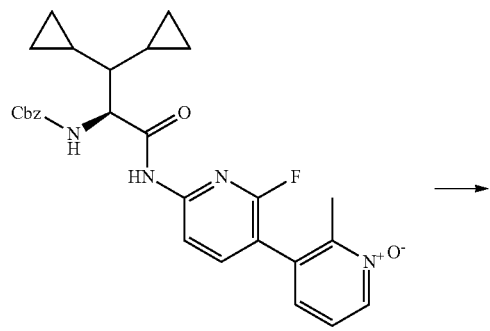

According to the method of Preparation 1, tert-butyl N-[(1S)-1-[(5-bromo-6-chloro-2-pyridyl)carbamoyl]-2,2-dicyclopropyl-ethyl]carbamate (synthesized according to Preparation 138 from WO2021250194) (2.38 g, 5.19 mmol) was reacted to give the title compound (2.05 g) as a pale orange foam. LCMS (METHOD 3) (ES): m/z 358.4, 360.4 [M+H]$^+$, RT=0.63 min.

Preparation 45: N-[(1S)-1-[(5-bromo-6-chloro-2-pyridyl)carbamoyl]-2,2-dicyclopropyl-ethyl]-2-isopropyl-pyrazole-3-carboxamide

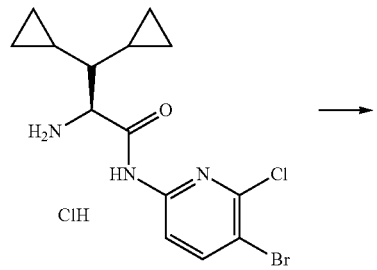

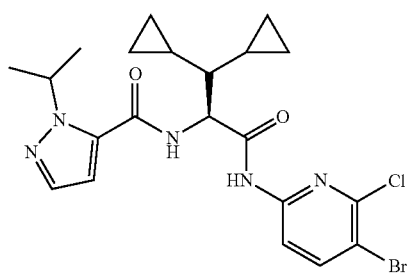

According to the method of Preparation 2 the compound of Preparation 44 (2.05 g, 5.19 mmol) was reacted with 2-isopropylpyrazole-3-carboxylic acid to give the title compound (2.00 g, 78%) as a pale yellow solid. LCMS (METHOD 4) (ES): m/z 494.4, 496.3 [M+H]$^+$, RT=0.90 min; $^1$H NMR (400 MHZ, DMSO-d$_6$) δ 11.14 (s, 1H), 8.46 (d, J=8.5 Hz, 1H), 8.20 (d, J=8.7 Hz, 1H), 8.03 (d, J=8.7 Hz, 1H), 7.51 (d, J=1.9 Hz, 1H), 6.91 (d, J=2.0 Hz, 1H), 5.37 (hept, J=6.6 Hz, 1H), 4.88 (t, J=7.9 Hz, 1H), 1.38 (d, J=6.6 Hz, 3H), 1.34 (d, J=6.6 Hz, 3H), 1.07-0.92 (m, 1H), 0.92-0.79 (m, 1H), 0.74 (q, J=7.4 Hz, 1H), 0.57-0.43 (m, 1H), 0.42-0.06 (m, 7H).

Preparation 46: N-[(1S)-1-[[6-chloro-5-(2,5-dimethyl-3-pyridyl)-2-pyridyl]carbamoyl]-2,2-dicyclopropyl-ethyl]-2-isopropyl-pyrazole-3-carboxamide

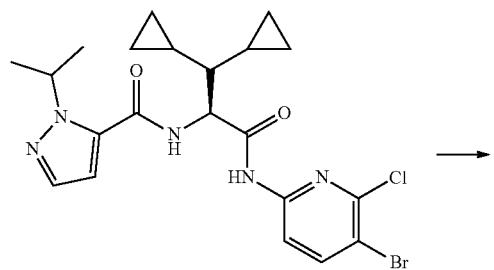

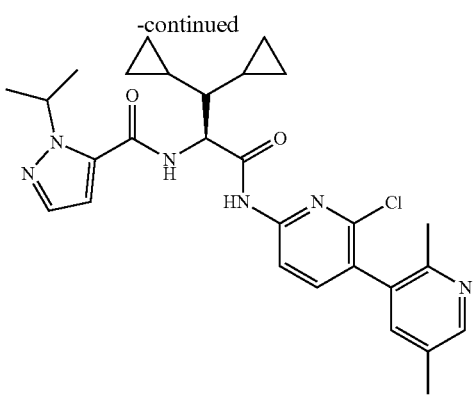

According to the method of Preparation 3 the compound of Preparation 45 was reacted with bis(pinacolato)diboron followed by 3-bromo-2,5-dimethyl-pyridine to give the title compound (277 mg, 49%) as a pale yellow solid as a mixture of atropisomers. LCMS (METHOD 3) (ES): m/z 521.8 [M+H]$^+$, RT=0.87 and 0.88 min; $^1$H NMR (600 MHz, DMSO-d$_6$) δ 11.14 and 11.11 (2×s, 1H), 8.50-8.44 (m, 1H), 8.36 (m, 1H), 8.16 (d, J=8.2 Hz, 1H), 7.85 and 7.83 (2×s, 1H), 7.51 (m, 1H), 7.48-7.40 (m, 1H), 6.95-6.87 (m, 1H), 5.44-5.33 (m, 1H), 4.95-4.86 (m, 1H), 2.30 (s, 3H), 2.24 (2×s, 3H), 1.39 (d, J=6.6 Hz, 3H), 1.35 (d, J=6.6 Hz, 3H), 1.04-0.94 (m, 1H), 0.93-0.83 (m, 1H), 0.77 (q, J=7.4 Hz, 1H), 0.54-0.45 (m, 1H), 0.43-0.36 (m, 1H), 0.35-0.14 (m, 6H).

Preparation 47: N-[(1S)-1-[[6-chloro-5-(5-fluoro-2-methyl-3-pyridyl)-2-pyridyl]carbamoyl]-2,2-dicyclopropyl-ethyl]-2-isopropyl-pyrazole-3-carboxamide

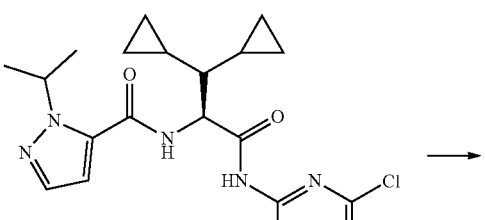

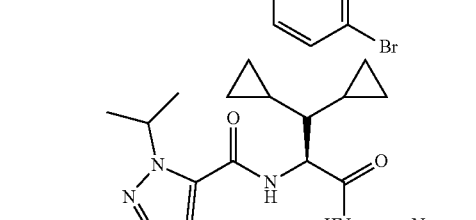

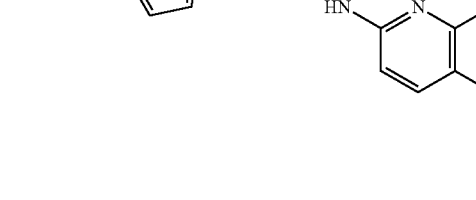

According to the method of Preparation 3 the compound of Preparation 45 was reacted with bis(pinacolato)diboron followed by 3-bromo-5-fluoro-2-methyl-pyridine to give the title compound (35 mg, 51%) as a beige solid. LCMS (METHOD 4) (ES): m/z 525.5 [M+H]$^+$, RT=0.80 min.

Preparation 48: 5-(2,5-dimethyl-3-pyridyl)-6-fluoro-pyridin-2-amine

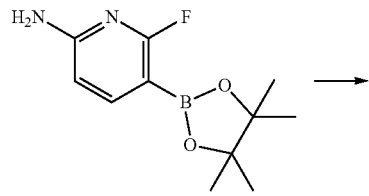

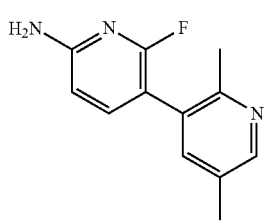

According to the method of Preparation 20 the compound of Preparation 19 (3.0 g, 12.6 mmol) was reacted with 3-bromo-2,5-dimethyl-pyridine to give the title compound (2.30 g, 84% yield). LCMS (METHOD 2) (ESI): m/z 218.1 [M+H]$^+$, RT=1.47 min. (YMC TRIAT C18 (50 mm×2.1 mm, 1.9 μm), 0.05% formic acid in MeCN, 0.05% formic acid in H$_2$O).

Preparation 49: benzyl N-[(1S)-1-(dicyclopropylmethyl)-2-[[5-(2,5-dimethyl-3-pyridyl)-6-fluoro-2-pyridyl]amino]-2-oxo-ethyl]carbamate

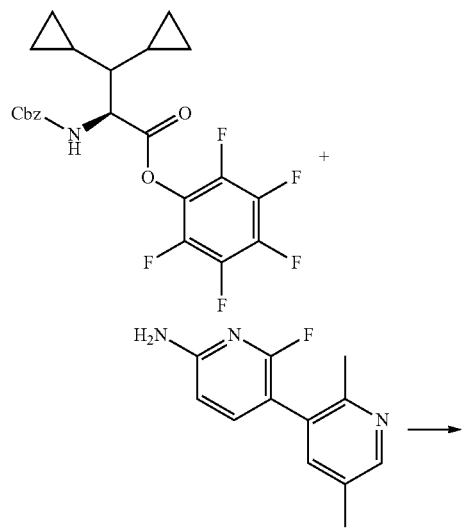

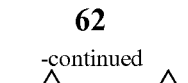

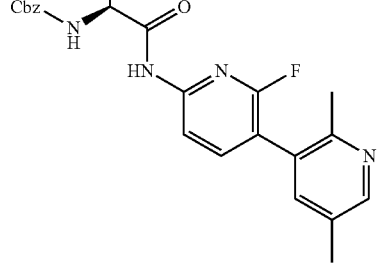

According to the method of Preparation 21 the compound of Preparation 48 (2.20 g, 10 mmol) was reacted with the compound of Preparation 17 (4.80 g, 10 mmol) to afford the title compound (3.20 g, 62% yield) after purification by column chromatography (eluting with 50% EtOAc in pet. ether). LCMS (METHOD 2) (ESI): m/z 503.6 [M+H]$^+$, RT=1.72 min. (YMC TRIART C18 50 mm×2.1 mm, 1.9 μm), 0.05% formic acid in MeCN, 0.05% formic acid in H$_2$O).

Preparation 50: (2S)-2-amino-3,3-dicyclopropyl-N-[5-(2,5-dimethyl-3-pyridyl)-6-fluoro-2-pyridyl]propanamide

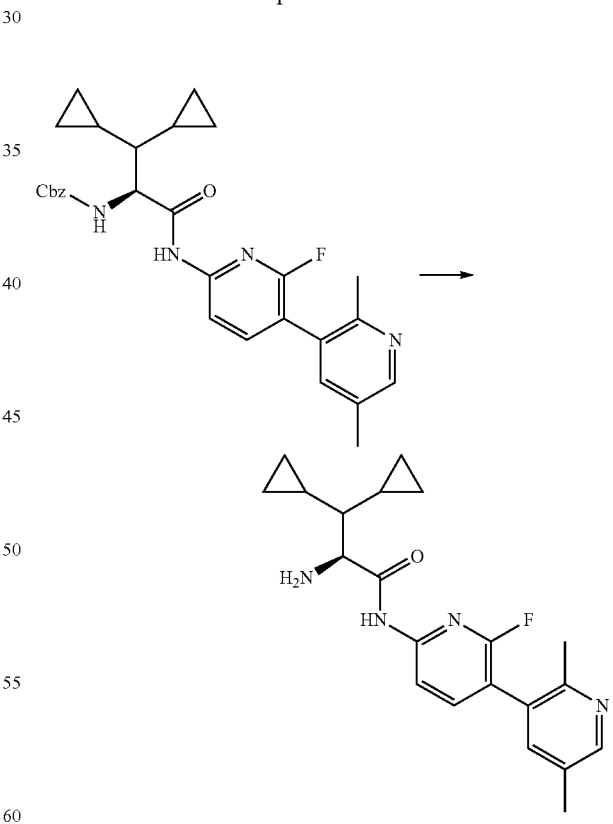

According to the method of Preparation 26 the compound of Preparation 49 (2.70 g, 5.4 mmol) was reacted to give the title compound (assumed 100% yield) as a pale yellow solid. LCMS (METHOD 2) (ESI): m/z 369.5 [M+H]$^+$, RT=4.08 min. (YMC TRIART C18 50 mm×2.1 mm, 1.9 μm), 0.05% formic acid in MeCN, 0.05% formic acid in H$_2$O).

Preparation 51: tert-butyl N-[(1S)-1-(dicyclopropyl-methyl)-2-[[5-(2,5-dimethyl-3-pyridyl)-6-fluoro-2-pyridyl]amino]-2-oxo-ethyl]carbamate

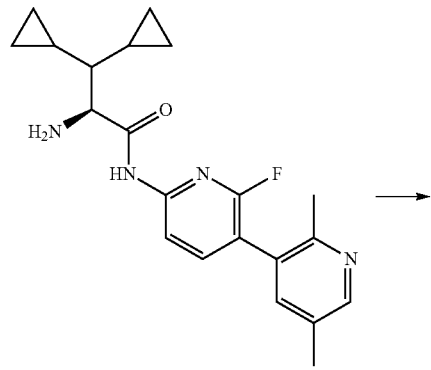

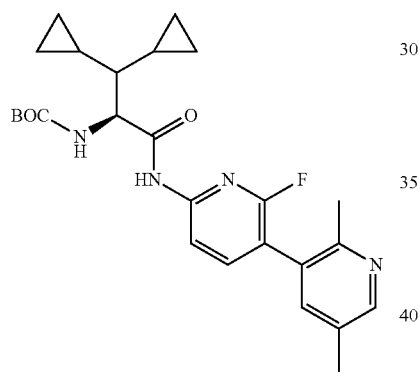

Triethylamine (742 mg, 7.33 mmol) was added to a stirred solution of the compound of Preparation 50 (900 mg, 2.44 mmol) in DCM (10 mL) at 0° C. After 10 minutes (Boc)$_2$O (639 mg, 2.93 mmol) was added and the mixture was stirred for 4 hours at room temperature. Water (50 mL) was added and the mixture was extracted with EtOAc (2×50 mL). The combined organic extracts were washed with brine (30 mL), dried over sodium sulfate, concentrated in vacuo and purified by column chromatography (eluting with 45% EtOAc in pet. ether) to give the title compound (1.1 g, 96% Yield). LCMS (METHOD 2) (ESI): m/z 469.5 [M+H]$^+$, RT=1.77 min. (Acquity BEH C18 (50 mm×2.1 mm), 0.05% formic acid in MeCN, 0.05% formic acid in H$_2$O).

Preparation 52: tert-butyl N-[(1S)-1-(dicyclopropyl-methyl)-2-[[5-(2,5-dimethyl-1-oxido-pyridin-1-ium-3-yl)-6-fluoro-2-pyridyl]amino]-2-oxo-ethyl]carbamate

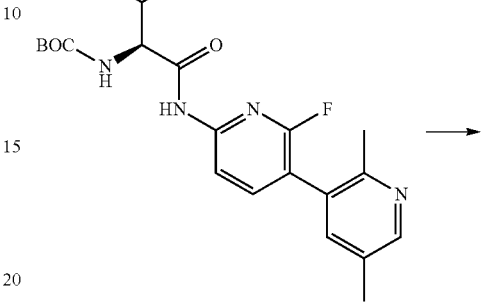

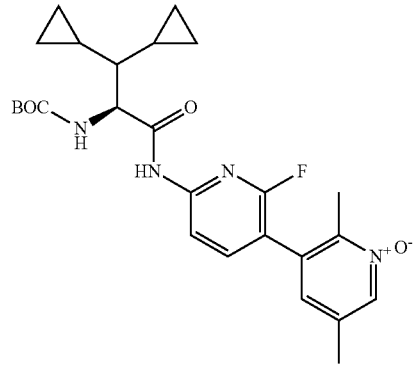

mCPBA (610 mg, 3.5 mmol) was added to a stirred solution of the compound of Preparation 51 (1.1 g, 2.3 mmol) in DCM (15 mL) at 0° C. The mixture was allowed to warm to room temperature and stirred for 2 hours. The reaction mixture was quenched with sat. aq. NaHCO$_3$ (25 mL) and extracted with DCM (2×50 mL). The combined organic layer was dried over sodium sulfate, concentrated in vacuo and the residue was washed with diethyl ether to afford the title compound (1.1 g, 97% Yield). LCMS (METHOD 2) (ESI): m/z 485.5 [M+H]$^+$, RT=1.97 min. (Acquity BEH C18 (50 mm×2.1 mm), 0.05% formic acid in MeCN, 0.05% formic acid in H$_2$O).

Preparation 53: (2S)-2-amino-3,3-dicyclopropyl-N-[5-(2,5-dimethyl-1-oxido-pyridin-1-ium-3-yl)-6-fluoro-2-pyridyl]propenamide hydrochloride

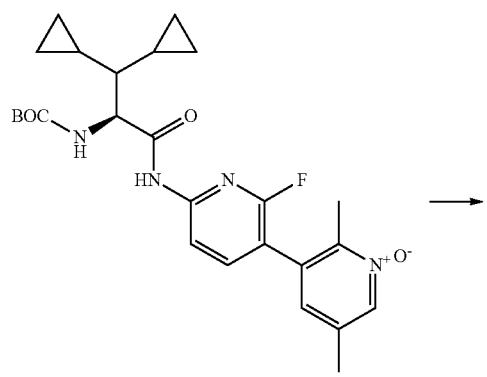

→

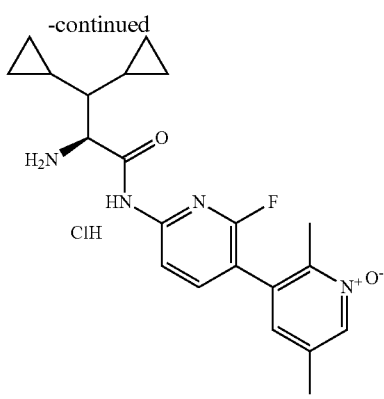

4M HCl in 1,4-dioxane (14 mL) was added to a stirred solution of the compound of Preparation 52 (1.4 g, 2.9 mmol) in 1,4-dioxane (15 mL) at 0° C. and the mixture was stirred for 16 hours at room temperature. The reaction mixture was concentrated in vacuo and the residue was washed with diethyl ether to afford the title compound (850 mg, 70% Yield). LCMS (METHOD 2) (ESI): m/z 385.3 [M+H]$^+$, RT=1.23 min. (Acquity BEH C18 (50 mm×2.1 mm), 0.05% formic acid in MeCN, 0.05% formic acid in H$_2$O).

Preparations 54 to 61

Preparations 54 to 61 were synthesized according to the method of Preparation 3 from the compound of Preparation 2 using the indicated bromopyridine or chloropyridine in the Suzuki coupling step.

| Prep. number | Name | Structure | Halopyridine starting material | LCMS details |
|---|---|---|---|---|
| 54 | N-[(1S)-2,2-dicyclopropyl-1-[[5-(4-cyclopropyl-3-pyridyl)-6-fluoro-2-pyridyl]carbamoyl]ethyl]-2-isopropyl-pyrazole-3-carboxamide | 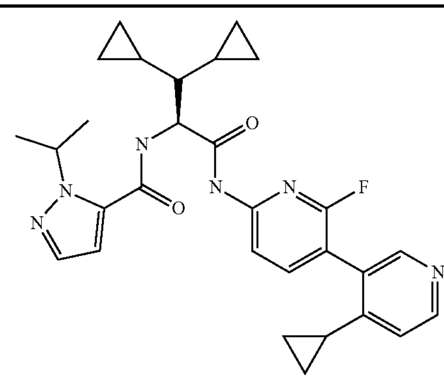 | | LCMS (ES): m/z 517.4 [M + H]$^+$, RT = 0.80 min (METHOD 4) |
| 55 | N-[(1S)-1-(dicyclopropyl-methyl)-2-[[5-[5-(difluoromethyl)-4-methyl-3-pyridyl]-6-fluoro-2-pyridyl]amino]-2-oxo-ethyl]-2-isopropyl-pyrazole-3-carboxamide | 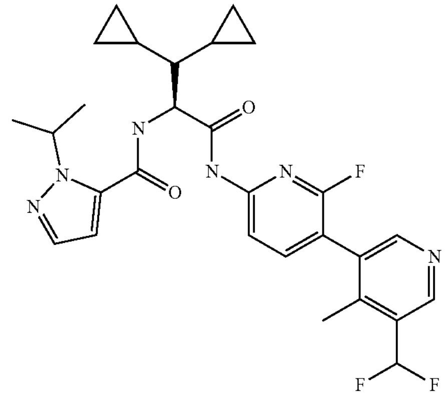 [SMILES: Cc1c(-c2ccc(NC(=O)[C@@H](NC(=O)c3ccnn3C(C)C)C(C3CC3)C3CC3)nc2F)cncc1C(F)F] | | LCMS (ES): m/z 539.6 [M − H]$^-$, RT = 0.87 min (METHOD 3) |

| Prep. number | Name | Structure | Halopyridine starting material | LCMS details |
|---|---|---|---|---|
| 56 | N-[(1S)-1-(dicyclopropyl-methyl)2-[[5-[5-(difluoromethyl)-2-methyl-3-pyridyl]-6-fluoro-2-pyridyl]amino]-2-oxo-ethyl]-2-isopropyl-pyrazole-3-carboxamide | 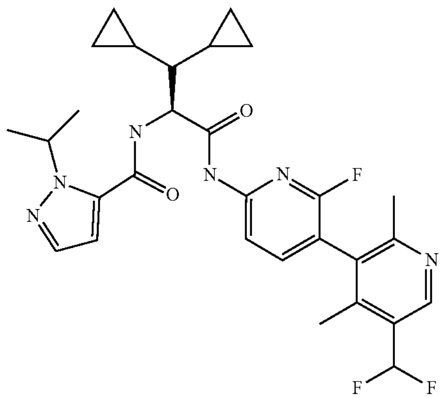 | | LCMS (ES): m/z 539.7 [M − H]⁻, RT = 0.87 min (METHOD 3) |
| 57 | N-[(1S)-1-(dicyclopropyl-methyl)-2-[[6-fluoro-5-[5-fluoro-4-(trifluoromethyl)-3-pyridyl]-2-pyridyl]amino]-2-oxo-ethyl]-2-isopropyl-pyrazole-3-carboxamide | 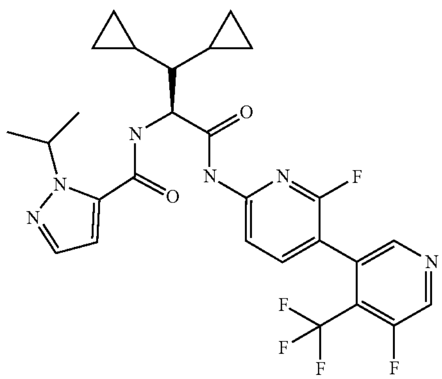 [SMILES: CC(C)n1nccc1C(=O)N[C@H](C(=O)Nc1ccc(-c2cncc(F)c2C(F)(F)F)c(F)n1)C(C1CC1)C1CC1] | | LCMS (ES): m/z 561.6 [M − H]⁻, RT = 0.92 min (METHOD 3) |
| 58 | N-[(1S)-1-(dicyclopropyl-methyl)-2-[[5-[4-(difluoromethyl)-3-pyridyl]-6-fluoro-2-pyridyl]amino]-2-oxo-ethyl]-2-isopropyl-pyrazole-3-carboxamide | 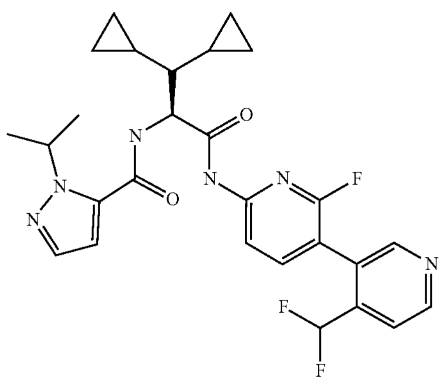 [SMILES: CC(C)n1nccc1C(=O)N[C@H](C(=O)Nc1ccc(-c2cnccc2C(F)F)c(F)n1)C(C1CC1)C1CC1] | | LCMS (ES): m/z 525.6 [M − H]⁻, RT = 0.84 min (METHOD 3) |
| 59 | N-[(1S)-1-(dicyclopropyl-methyl)-2-[[5-(4,5-dimethyl-3-pyridyl)-6-fluoro-2-pyridyl]amino]-2-oxo-ethyl]-2-isopropyl-pyrazole-3-carboxamide | 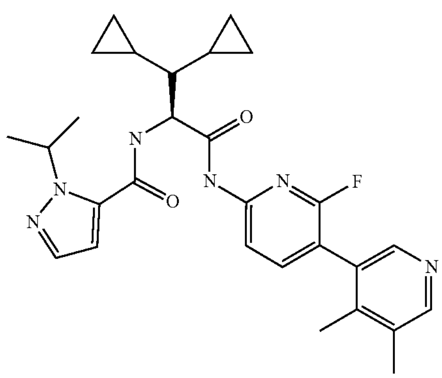 [SMILES: Cc1cncc(-c2ccc(NC(=O)[C@@H](NC(=O)c3ccnn3C(C)C)C(C3CC3)C3CC3)nc2F)c1C] | | LCMS (ES): m/z 503.7 [M − H]⁻, RT = 0.84 min (METHOD 3) |

| Prep. number | Name | Structure | Halopyridine starting material | LCMS details |
|---|---|---|---|---|
| 60 | N-[(1S)-1-(dicyclopropyl-methyl)-2-[[5-(4-ethyl-3-pyridyl)-6-fluoro-2-pyridyl]amino]-2-oxo-ethyl]-2-isopropyl-pyrazole-3-carboxamide | 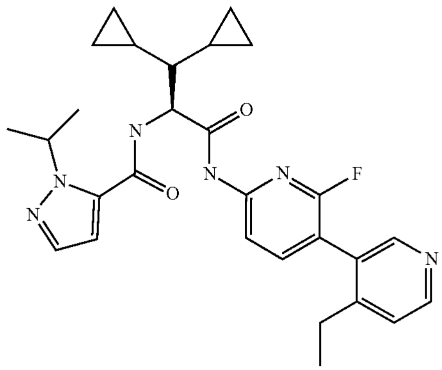 [SMILES: CCc1ccncc1-c1ccc(NC(=O)[C@@H](NC(=O)c2ccnn2C(C)C)C(C2CC2)C2CC2)nc1F] | (Br, 3-pyridyl with 4-ethyl) | LCMS (ES): m/z 503.7 [M − H]⁻, RT = 0.86 min (METHOD 3) |
| 61 | N-[(1S)-1-(dicyclopropyl-methyl)-2-[[5-(2-ethyl-5-methoxy-3-pyridyl)-6-fluoro-2-pyridyl]amino]-2-oxo-ethyl]-2-isopropyl-pyrazole-3-carboxamide | 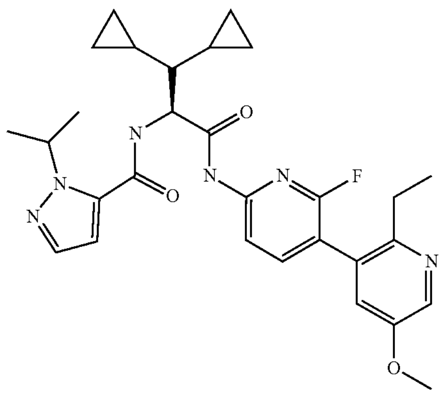 [SMILES: CCc1ncc(OC)cc1-c1ccc(NC(=O)[C@@H](NC(=O)c2ccnn2C(C)C)C(C2CC2)C2CC2)nc1F] | (Cl, 2-ethyl-5-methoxy-3-pyridyl) Preparation 73 | LCMS (ES): m/z 535.26 [M + H]⁺, RT = 1.08 min (METHOD 2) |

Preparation 62: 5-[2-chloro-4-(trifluoromethyl)-3-pyridyl]-6-fluoro-pyridin-2-amine Preparation 63: 6-fluoro-5-[2-methyl-4-(trifluoromethyl)-3-pyridyl]pyridin-2-amine

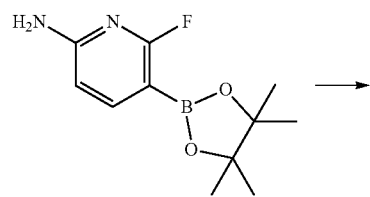

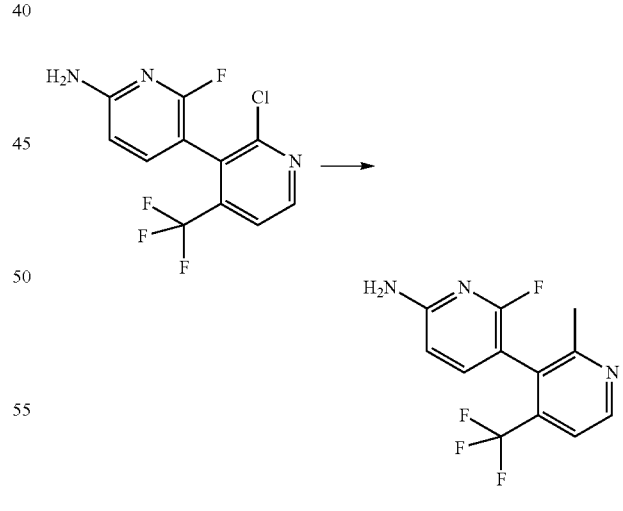

According to the method of Preparation 20 the compound of Preparation 19 (1.05 g, 4.41 mmol) was reacted with 2-chloro-3-iodo-4-(trifluoromethyl)pyridine to give the title compound (193 mg, 15% yield) contaminated with 6-fluoropyridin-2-amine. This material was used without further purification. LCMS (METHOD 3) (ES): m/z 292.3 [M+H]⁺, RT=0.68 min.

A mixture of the compound of Preparation 62 (325 mg, 1.11 mmol), methylboronic acid (200 mg, 3.34 mmol), K₂CO₃ (308 mg, 2.23 mmol) and Pd(dppf)Cl₂ (41 mg, 0.056 mmol) in degassed dioxane (6 mL) in a capped microwave vial was stirred at 120° C. for 3 hours. After cooling to room temperature, the mixture was concentrated in vacuo, redissolved in EtOAc (30 mL), washed with water (20 mL), dried (Na₂SO₄) and concentrated in vacuo. Purification by column chromatography (eluting with EtOAc:heptane) gave the title compound (155 mg, 51% Yield) as a pale yellow oil. LCMS (METHOD 3) (ES): m/z 272.4 [M+H]$^+$, RT=0.63 min.

Preparation 64: benzyl N-[(1S)-1-(dicyclopropylmethyl)-2-[[6-fluoro-5-[2-methyl-4-(trifluoromethyl)-3-pyridyl]-2-pyridyl]amino]-2-oxo-ethyl]carbamate

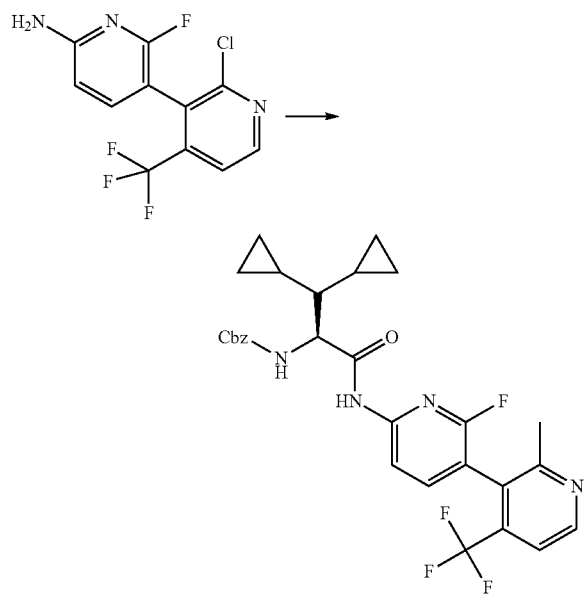

According to the Method of Preparation 11 the compound of Preparation 63 (155 mg, 0.572 mmol) was reacted with (2S)-2-(benzyloxycarbonylamino)-3,3-dicyclopropyl-propanoic acid (Preparation 349 from WO2021250194) (170 mg, 0.57 mmol) to give the title compound (125 mg, 39% Yield) as a beige solid. LCMS (METHOD 3) (ES): m/z 557.8 [M+H]$^+$, RT=0.94 min.

Preparation 65: N-[(1S)-1-(dicyclopropylmethyl)-2-[[6-fluoro-5-[2-methyl-4-(trifluoromethyl)-3-pyridyl]-2-pyridyl]amino]-2-oxo-ethyl]-2-isopropyl-pyrazole-3-carboxamide

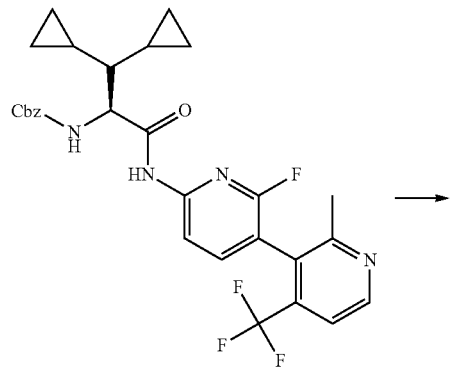

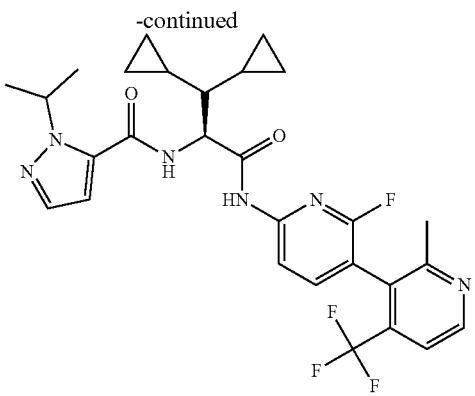

According to the method of Preparation 15 the compound of Preparation 64 (36 mg, 0.065 mmol) was reacted to give the title compound (28 mg, 78% Yield) as a colorless solid. LCMS (METHOD 3) (ES): m/z 559.8 [M+H]$^+$, RT=0.90 min.

Preparation 66: 6-chloro-5-(4,4,5,5-tetramethyl-1,3,2-dioxaborolan-2-yl)pyridin-2-amine

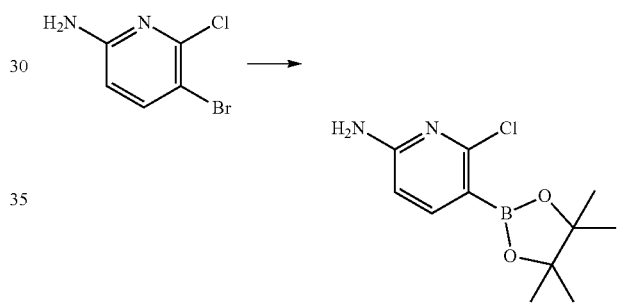

According to the method of Preparation 19 5-bromo-6-chloro-pyridin-2-amine (3.00 g, 14.5 mmol) was reacted to give the title compound (1.8 g, 49% Yield). LCMS (METHOD 2) (ESI): m/z 255.1 [M+H]$^+$, RT=0.93 min, Column: (Acquity BEH C18 (30 mm×3.0 mm, 1.7 μm); 0.05% formic acid in MeCN, 0.05% formic acid in H$_2$O).

Preparation 67: 6-chloro-5-(2,4-dimethyl-3-pyridyl)pyridin-2-amine

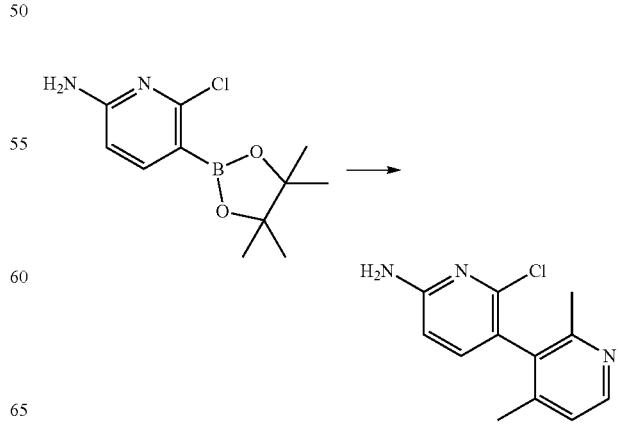

K₃PO₄ (1.75 g, 8.23 mmol) was added to a solution of the compound of Preparation 66 (2.0 g, 7.86 mmol) and 3-bromo-2,4-dimethyl-pyridine (1.46 g, 7.86 mmol) in 1,4-dioxane (20 mL) and H₂O (1 mL). The reaction mixture was thoroughly degassed for 30 minutes, Ruphos Pd G2 (305 mg, 0.39 mmol) was added and the sealed reaction mixture was stirred under microwave conditions at 120° C. for 1 hour. The cooled reaction mixture was filtered through Celite™ and diluted with water. The mixture was extracted with EtOAc (2×100 mL) and the combined organic extracts were dried over Na₂SO₄, filtered, and concentrated in vacuo. The obtained crude compound was purified by column chromatography (eluting with 30% EtOAc in pet. ether) to afford the title compound (800 mg, 42% yield). LCMS (METHOD 2) (ESI): m/z 234.2 [M+H]⁺, RT=0.72 min. (Acquity BEH C18 (50 mm×2.1 mm), 0.05% formic acid in MeCN, 0.05% formic acid in H₂O).

Preparation 68: benzyl N-[(1S)-1-[[6-chloro-5-(2,4-dimethyl-3-pyridyl)-2-pyridyl]carbamoyl]-2,2-dicyclopropyl-ethyl]carbamate

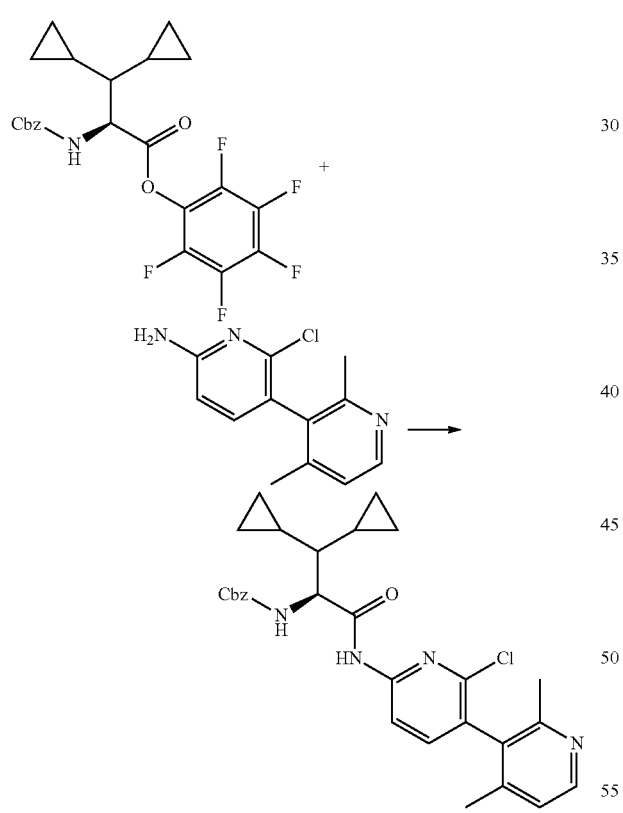

According to the method of Preparation 21 the compound of Preparation 67 (800 mg, 3.42 mmol) was reacted with the compound of Preparation 17 to give the title compound (1.50 g, 84% yield) as a mixture of atropisomers. LCMS (METHOD 2) (ESI): m/z 519.5 [M+H]⁺, RT=1.96 and 1.98 min. (Acquity BEH C18 (50 mm×2.1 mm), 0.05% formic acid in MeCN, 0.05% formic acid in H₂O).

Preparation 69: N-[(1S)-1-[[6-chloro-5-(2,4-dimethyl-3-pyridyl)-2-pyridyl]carbamoyl]-2,2-dicyclopropyl-ethyl]-2-isopropyl-pyrazole-3-carboxamide

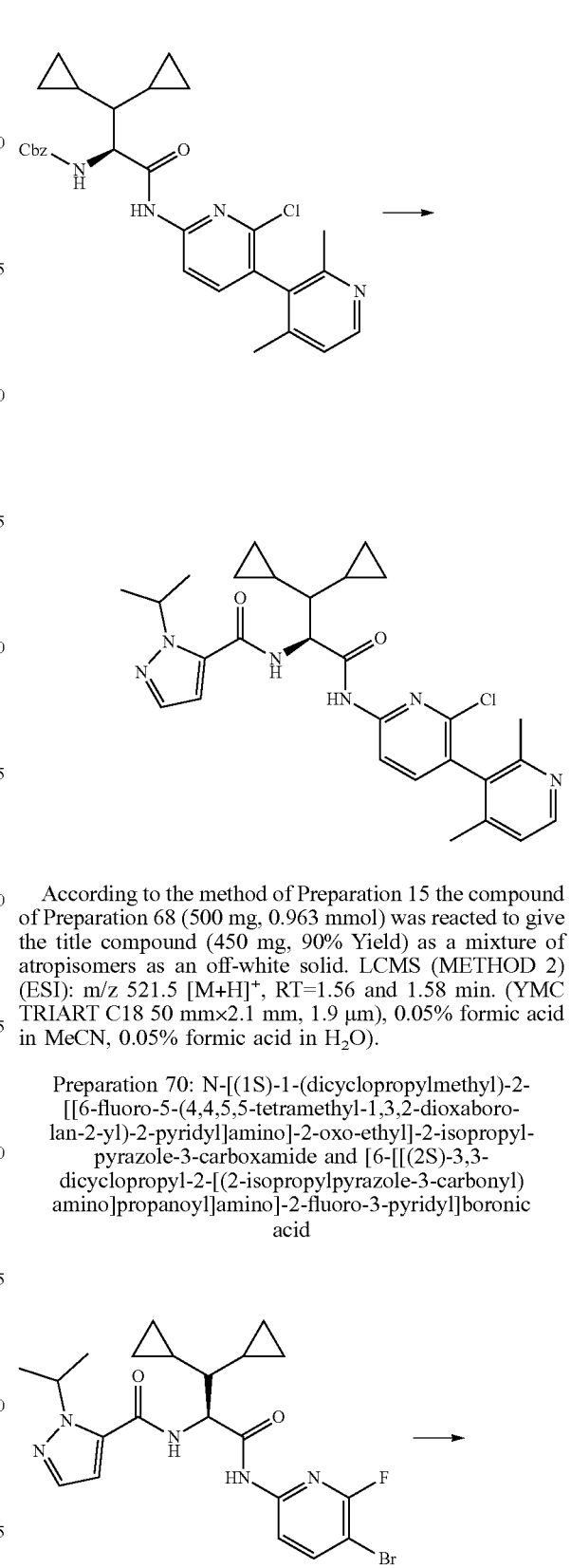

According to the method of Preparation 15 the compound of Preparation 68 (500 mg, 0.963 mmol) was reacted to give the title compound (450 mg, 90% Yield) as a mixture of atropisomers as an off-white solid. LCMS (METHOD 2) (ESI): m/z 521.5 [M+H]⁺, RT=1.56 and 1.58 min. (YMC TRIART C18 50 mm×2.1 mm, 1.9 μm), 0.05% formic acid in MeCN, 0.05% formic acid in H₂O).

Preparation 70: N-[(1S)-1-(dicyclopropylmethyl)-2-[[6-fluoro-5-(4,4,5,5-tetramethyl-1,3,2-dioxaborolan-2-yl)-2-pyridyl]amino]-2-oxo-ethyl]-2-isopropyl-pyrazole-3-carboxamide and [6-[[(2S)-3,3-dicyclopropyl-2-[(2-isopropylpyrazole-3-carbonyl)amino]propanoyl]amino]-2-fluoro-3-pyridyl]boronic acid

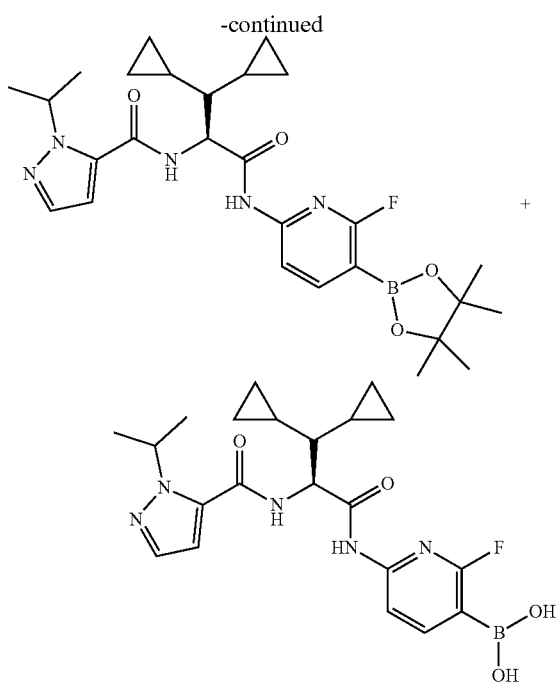

Pd(dppf)Cl₂ (33 mg, 0.045 mmol) was added to a degassed mixture of the compound of Preparation 2 (432 mg, 0.903 mmol), bis(pinacolato)diboron (275 mg, 1.08 mmol) and KOAc (266 mg, 2.71 mmol) in dry dioxane (15 mL) in a 2-necked flask. The mixture was stirred at 100° C. under N₂ for 1 hour, then cooled to room temperature and evaporated. EtOAc (30 mL) was added to the residue, the mixture was washed with water (15 mL), dried (Na₂SO₄) and evaporated to give a crude mixture of boronic acid and boronic ester (340 mg) that was used without further purification. LCMS (METHOD 3) (ES): m/z 444.5 [M+H]⁺, RT=0.71 min and m/z 526.6 [M+H]⁺, RT=0.96 min.

Preparation 71: 5-chloro-6-methyl-1-oxido-pyridin-1-ium-3-carbonitrile

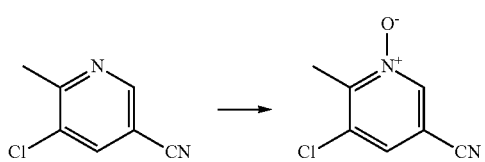

To a stirred solution of 5-chloro-6-methyl-pyridine-3-carbonitrile (150 mg, 0.983 mmol) in DCM (5 mL) at 0° C. was added mCPBA (676 mg, 1.97 mmol). The reaction mixture was stirred for 1 hour at room temperature then ice water (10 mL) was added. The mixture was extracted with DCM (100 mL) and the organic layer was washed with sat. aq. NaHCO₃ solution (20 mL), dried over anhydrous Na₂SO₄ and concentrated in vacuo to give the title compound (80 mg, 48% Yield) as a colorless solid. LCMS (METHOD 2) (ESI): m/z: 169.3 [M+H]⁺, RT=1.57 min. (Acquity BEH C18 (50 mm×2.1 mm), 0.05% formic acid in MeCN, 0.05% formic acid in H₂O); ¹H NMR (400 MHZ, CDCl₃) δ 8.41 (d, J=0.8 Hz, 1H), 7.49 (d, J=0.8 Hz, 1H), 2.67 (s, 3H).

Preparation 72: 3-Chloro-2-ethyl-5-hydroxy-pyridine

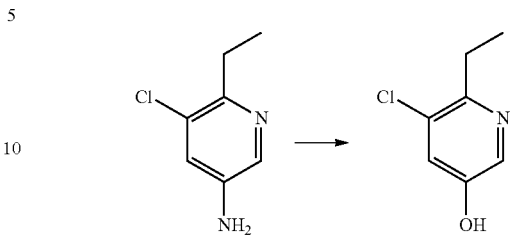

To a stirred solution of 3-amino-5-chloro-6-ethyl-pyridine (1.6 g, 10 mmol) in 10% aq. H₂SO₄ (16 mL) was added a solution of NaNO₂ (18 mmol) in 10 mL of water dropwise at 0-5° C. over a period of 10 minutes and the reaction maintained at 0° C. for additional 20 min. The mixture was then heated on a steam bath for 20 min at 90-100° C. The reaction progress was monitored by TLC & LCMS. After completion of reaction, the reaction mass was cooled to room temperature and neutralized with K₂CO₃ to pH 7. Then the reaction mixture was extracted with DCM (3×100 mL), the collected organic layer was dried over anhydrous Na₂SO₄ and concentrated in vacuo to afford crude mass. The crude compound was purified by column chromatography (eluting with 40% EtOAc in pet. ether) to afford the title compound (1 g, 5.39 mmol, 53%). ¹H NMR (400 MHZ, CDCl₃) δ ppm 10.15 (Br s, 1H), 8.07 (d, J=2.50 Hz, 1H), 7.30 (d, J=2.50 Hz, 1H), 2.90 (q, J=7.63 Hz, 2H), 1.25 (t, J=7.57 Hz, 3H); LCMS (ESI): m/z: 157.98 [M+H+] & m/z: 159.98 [M+2H+]; 85.18%; RT=0.72 min. (Acquity BEH C18 (30*3.0 mm, 1.7 μm), Mobile phase A: 0.05% FA in water, Mobile phase B: 0.05% FA in ACN).

Preparation 73: 3-Chloro-2-ethyl-5-methoxy-pyridine

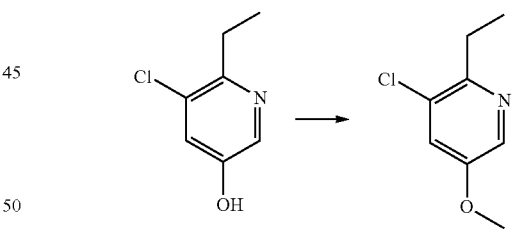

To a stirred solution of Preparation 72 (1 g, 6.34 mmol) in DMF (10 mL) was added K₂CO₃ (2.1 g, 15.86 mmol) and CH₃I (1.3 g, 9.51 mmol) at 0° C. and stirred at RT for 16 h. The reaction progress was monitored by TLC and LCMS. After completion of reaction, the reaction mixture was diluted with water (20 mL) and extracted with ethyl acetate (2×100 mL). The combined organic extract was washed with brine (20 mL), dried over anhydrous Na₂SO₄, filtered, and concentrated in vacuo, and purified by column chromatography (eluting with 30% EtOAc in pet. ether) to afford the title compound (750 mg, 3.84 mmol, 60%) as a light brown liquid. ¹H NMR (400 MHZ, CDCl₃) δ 8.15 (d, J=2.63 Hz, 1H), 7.20 (d, J=2.63 Hz, 1H), 3.84 (s, 3H), 2.89 (q, J=7.50 Hz, 2H), 1.27 (t, J=7.57 Hz, 3H); LCMS (ESI): m/z: 172.02 [M+H+] & m/z: 174.03 [M+2H+]; 88.18%; RT=0.97 min.

EXAMPLES

Example 1: N-[(1S)-1-(dicyclopropylmethyl)-2-[[6-fluoro-5-(5-methoxy-2-methyl-1-oxido-pyridin-1-ium-3-yl)-2-pyridyl]amino]-2-oxo-ethyl]-2-isopropyl-pyrazole-3-carboxamide

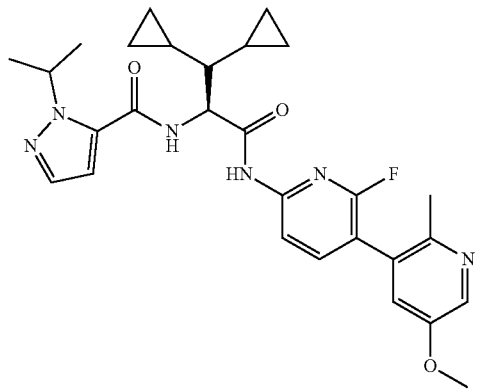

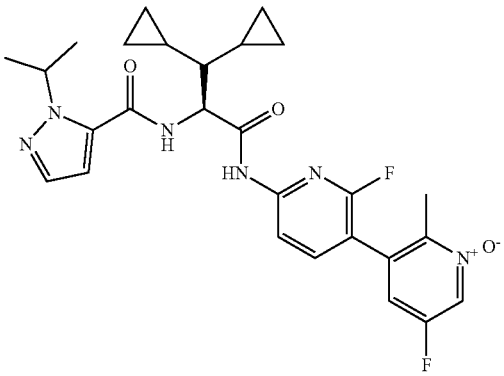

mCPBA (77%, 150 mg, 0.66 mmol) was added to a solution of the compound of Preparation 3 (310 mg, 0.60 mmol) in DCM (20 mL) and the mixture was stirred for 1 hour at room temperature. The reaction mixture was diluted with DCM (15 mL), washed with sat. aq. NaHCO$_3$ (6 mL), dried (Na$_2$SO$_4$) and evaporated. The crude product was taken up in MeCN (4 mL) and the product then crystallized. The solid was filtered off and dried in vacuo to give the title compound (236 mg, 74%) as an off-white solid. LCMS (ES): m/z 537.263 [M+H]$^+$, RT=2.31 min; $^1$H NMR (600 MHZ, DMSO-d$_6$) δ 11.08 (s, 1H), 8.49 (d, J=8.6 Hz, 1H), 8.22 (d, J=2.4 Hz, 1H), 8.12 (dd, J=8.2, 1.7 Hz, 1H), 8.02 (dd, J=10.0, 8.2 Hz, 1H), 7.52 (d, J=2.0 Hz, 1H), 7.07 (d, J=2.4 Hz, 1H), 6.92 (d, J=1.9 Hz, 1H), 5.38 (hept, J=6.6 Hz, 1H), 4.91 (t, J=8.0 Hz, 1H), 3.83 (s, 3H), 2.15 (s, 3H), 1.39 (d, J=6.6 Hz, 3H), 1.35 (d, J=6.6 Hz, 3H), 1.04-0.94 (m, 1H), 0.92-0.83 (m, 1H), 0.77 (td, J=9.5, 7.5 Hz, 1H), 0.55-0.45 (m, 1H), 0.43-0.35 (m, 1H), 0.35-0.12 (m, 6H).

Example 2: N-[(1S)-1-(dicyclopropylmethyl)-2-[[6-fluoro-5-(5-fluoro-2-methyl-1-oxido-pyridin-1-ium-3-yl)-2-pyridyl]amino]-2-oxo-ethyl]-2-isopropyl-pyrazole-3-carboxamide

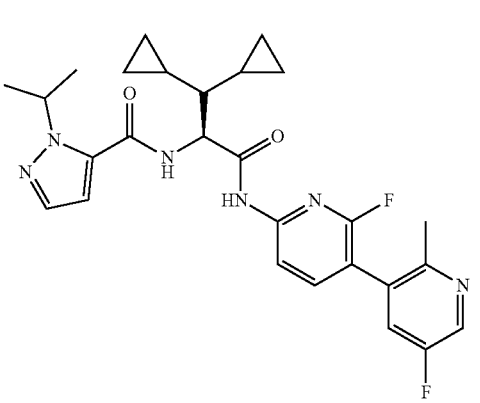

According to the Method of Example 1 the pyridine of Preparation 4 was oxidized to give the title compound (268 mg, 63%) as a colorless solid. LCMS (ES): m/z 525.243 [M+H]$^+$, RT=2.33 min; $^1$H NMR (600 MHz, DMSO-d$_6$) δ 10.89 (s, 1H), 8.46 (dd, J=4.6, 2.4 Hz, 1H), 8.26 (d, J=8.5 Hz, 1H), 7.90 (dd, J=8.3, 1.7 Hz, 1H), 7.82 (dd, J=10.0, 8.2 Hz, 1H), 7.28 (d, J=1.9 Hz, 1H), 7.25 (dd, J=8.3, 2.4 Hz, 1H), 6.69 (d, J=2.0 Hz, 1H), 5.15 (hept, J=6.7 Hz, 1H), 4.68 (t, J=8.0 Hz, 1H), 1.96 (s, 3H), 1.15 (d, J=6.6 Hz, 3H), 1.12 (d, J=6.6 Hz, 3H), 0.81-0.71 (m, 1H), 0.70-0.60 (m, 1H), 0.54 (td, J=9.6, 7.6 Hz, 1H), 0.30-0.22 (m, 1H), 0.21-0.12 (m, 1H), 0.12--0.11 (m, 6H).

Example 3: N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-isopropyl-pyrazole-3-carboxamide Example 4: N-[(1S)-1-(dicyclopropylmethyl)-2-[[5-(2,4-dimethyl-1-oxido-pyridin-1-ium-3-yl)-6-fluoro-2-pyridyl]amino]-2-oxo-ethyl]-2-isopropyl-pyrazole-3-carboxamide

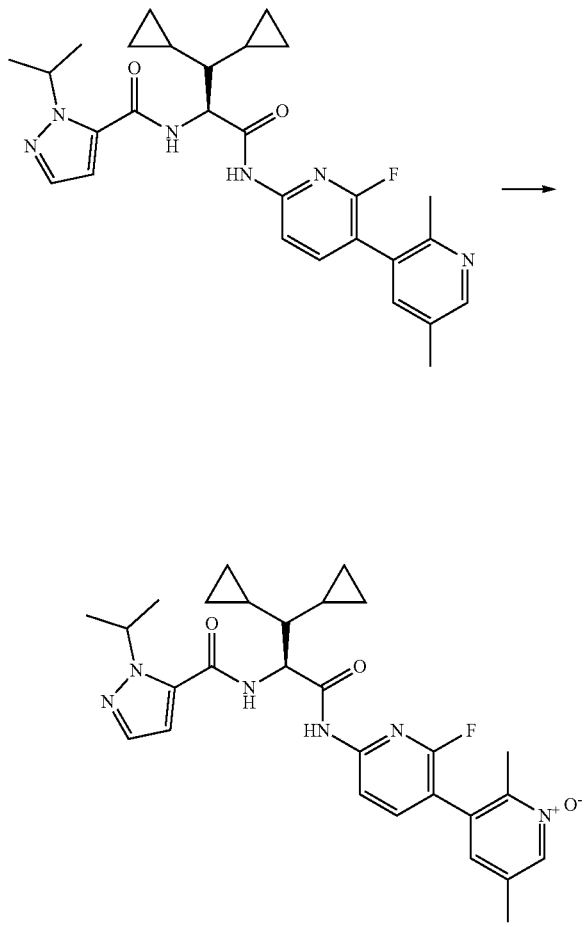

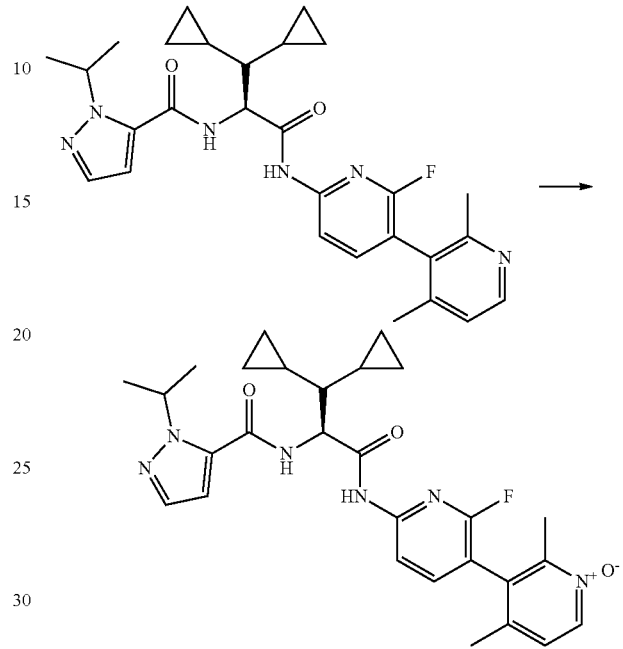

According to the Method of Example 1 the pyridine of Preparation 6 was oxidized to give the title compound (190 mg, 78%) as a 1:1 mixture of atropisomers as a colorless solid. LCMS (ES): m/z 521.267 [M+H]$^+$, RT=2.25 min; $^1$H NMR (400 MHZ, DMSO-d$_6$, 1:1-mixture of 2 atropisomers) δ 11.10 and 11.09 (2×s, 1H), 8.49 (d, J=8.4 Hz, 1H), 8.27 (d, J=6.6 Hz, 1H), 8.17-8.10 (m, 1H), 8.02-7.90 (m, 1H), 7.51 (d, J=1.9 Hz, 1H), 7.29 (d, J=6.7 Hz, 1H), 6.92 (d, J=2.0 Hz, 1H), 5.39 (hept, J=6.6 Hz, 1H), 4.97-4.85 (m, 1H), 2.13 and 2.12 (2×s, 3H), 2.02 and 2.01 (2×s, 2H), 1.39 (d, J=6.6 Hz, 3H), 1.35 (d, J=6.6 Hz, 3H), 1.06-0.93 (m, 1H), 0.93-0.82 (m, 1H), 0.82-0.70 (m, 1H), 0.54-0.44 (m, 1H), 0.44-0.12 (m, 7H).

Example 5: N-[(1S)-1-(dicyclopropylmethyl)-2-[[5-(2-ethyl-1-oxido-pyridin-1-ium-3-yl)-6-fluoro-2-pyridyl]amino]-2-oxo-ethyl]-2-isopropyl-pyrazole-3-carboxamide

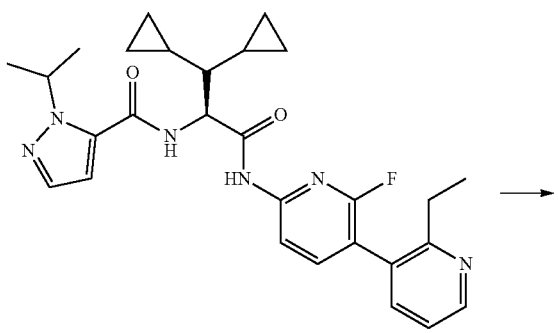

According to the Method of Example 1 the pyridine of Preparation 5 was oxidized to give the title compound (247 mg, 77%) as a colorless solid. LCMS (ES): m/z 521.268 [M+H]$^+$, RT=2.30 min; $^1$H NMR (600 MHz, DMSO-d$_6$) δ 11.07 (s, 1H), 8.48 (d, J=8.4 Hz, 1H), 8.28 (s, 1H), 8.12 (dd, J=8.2, 1.7 Hz, 1H), 8.01 (dd, J=10.0, 8.2 Hz, 1H), 7.51 (d, J=1.9 Hz, 1H), 7.17 (d, J=1.6 Hz, 1H), 6.92 (d, J=2.0 Hz, 1H), 5.38 (hept, J=6.7 Hz, 1H), 4.90 (t, J=8.0 Hz, 1H), 2.27 (s, 3H), 2.18 (s, 3H), 1.38 (d, J=6.6 Hz, 3H), 1.35 (d, J=6.6 Hz, 3H), 1.05-0.94 (m, 1H), 0.92-0.83 (m, 1H), 0.81-0.73 (m, 1H), 0.54-0.45 (m, 1H), 0.43-0.36 (m, 1H), 0.35-0.26 (m, 2H), 0.26-0.19 (m, 3H), 0.18-0.12 (m, 1H).

-continued

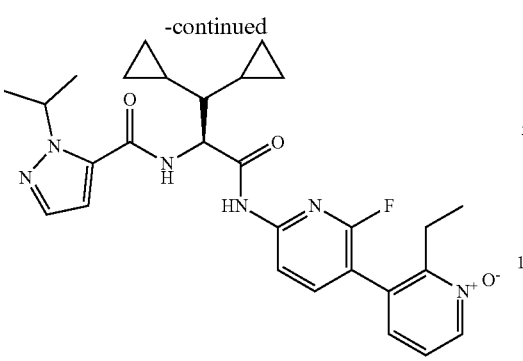

According to the Method of Example 1 the pyridine of Preparation 7 was oxidized to give the title compound (31 mg, 75%) as a colorless solid. LCMS (ES): m/z 521.268 [M+H]$^+$, RT=2.30 min; $^1$H NMR (400 MHZ, DMSO-d$_6$) δ 10.85 (s, 1H), 8.26 (d, J=8.4 Hz, 1H), 8.11 (dd, J=6.5, 1.2 Hz, 1H), 7.89 (dd, J=8.2, 1.7 Hz, 1H), 7.76 (dd, J=10.1, 8.1 Hz, 1H), 7.28 (d, J=1.9 Hz, 1H), 7.14 (dd, J=7.9, 6.4 Hz, 1H), 7.08-6.99 (m, 1H), 6.69 (d, J=2.0 Hz, 1H), 5.15 (hept, J=6.6 Hz, 1H), 4.67 (t, J=7.9 Hz, 1H), 2.56-2.34 (m, 2H), 1.15 (d, J=6.6 Hz, 3H), 1.11 (d, J=6.6 Hz, 3H), 0.81 (t, J=7.3 Hz, 3H), 0.78-0.70 (m, 1H), 0.69-0.59 (m, 1H), 0.54 (td, J=9.4, 7.4 Hz, 1H), 0.31-0.21 (m, 1H), 0.21--0.11 (m, 7H).

Example 6: N-[(1S)-1-(dicyclopropylmethyl)-2-[[6-fluoro-5-[1-oxido-4-(trifluoromethyl)pyridin-1-ium-3-yl]-2-pyridyl]amino]-2-oxo-ethyl]-2-isopropyl-pyrazole-3-carboxamide

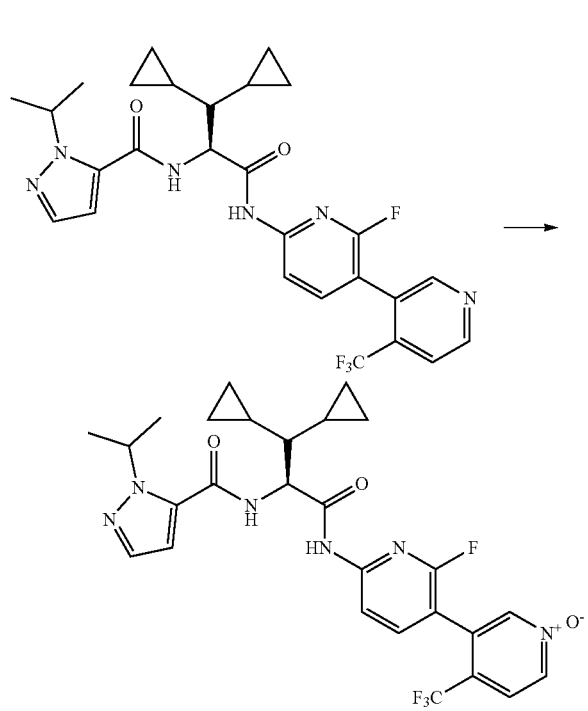

According to the Method of Example 1 the pyridine of Preparation 8 was oxidized to give the title compound (78 mg, 56%) as a colorless solid. LCMS (ES): m/z 561.224 [M+H]$^+$, RT=2.39 min; $^1$H NMR (400 MHZ, DMSO-d$_6$) δ 11.11 (s, 1H), 8.55 (s, 1H), 8.53-8.43 (m, 2H), 8.09 (dd, J=8.2, 1.8 Hz, 1H), 8.07-7.99 (m, 1H), 7.90 (d, J=6.9 Hz, 1H), 7.51 (d, J=2.0 Hz, 1H), 6.92 (d, J=2.0 Hz, 1H), 5.38 (hept, J=6.7 Hz, 1H), 4.89 (t, J=7.9 Hz, 1H), 1.38 (d, J=6.6 Hz, 3H), 1.35 (d, J=6.6 Hz, 3H), 1.05-0.93 (m, 1H), 0.93-0.82 (m, 1H), 0.82-0.70 (m, 1H), 0.56-0.44 (m, 1H), 0.45-0.09 (m, 7H).

Example 7: N-[(1S)-2,2-dicyclopropyl-1-[[5-(2-cyclopropyl-1-oxido-pyridin-1-ium-3-yl)-6-fluoro-2-pyridyl]carbamoyl]ethyl]-2-isopropyl-pyrazole-3-carboxamide

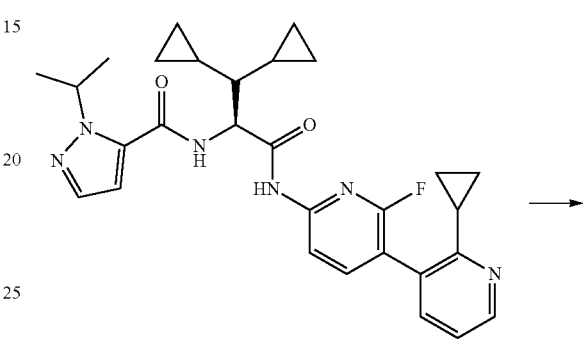

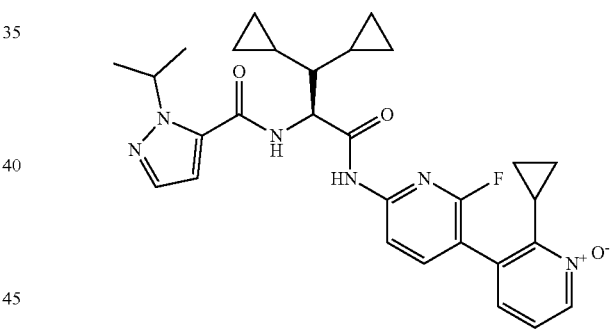

According to the Method of Example 1 the pyridine of Preparation 9 was oxidized to give the title compound (15 mg, 58%) as a colorless solid. LCMS (ES): m/z 533.268 [M+H]$^+$, RT=2.27 min; $^1$H NMR (400 MHZ, DMSO-d$_6$) δ 10.83 (s, 1H), 8.27 (d, J=8.5 Hz, 1H), 8.06 (dd, J=6.4, 1.2 Hz, 1H), 7.89 (dd, J=8.2, 1.8 Hz, 1H), 7.81 (dd, J=9.9, 8.2 Hz, 1H), 7.29 (d, J=2.0 Hz, 1H), 7.14 (dd, J=7.9, 6.4 Hz, 1H), 7.05 (dd, J=8.0, 1.3 Hz, 1H), 6.70 (d, J=2.0 Hz, 1H), 5.16 (hept, J=6.6 Hz, 1H), 4.68 (t, J=8.0 Hz, 1H), 1.69-1.55 (m, 1H), 1.16 (d, J=6.6 Hz, 3H), 1.12 (d, J=6.6 Hz, 3H), 0.84-0.70 (m, 1H), 0.70-0.59 (m, 1H), 0.60-0.48 (m, 3H), 0.33--0.15 (m, 10H).

Example 8: N-[(1S)-1-(dicyclopropylmethyl)-2-[[5-[5-(difluoromethoxy)-2-methyl-1-oxido-pyridin-1-ium-3-yl]-6-fluoro-2-pyridyl]amino]-2-oxo-ethyl]-2-isopropyl-pyrazole-3-carboxamide Example 9: N-[(1S)-1-(dicyclopropylmethyl)-2-[[6-fluoro-5-[5-(fluoromethoxy)-2-methyl-1-oxido-pyridin-1-ium-3-yl]-2-pyridyl]amino]-2-oxo-ethyl]-2-isopropyl-pyrazole-3-carboxamide

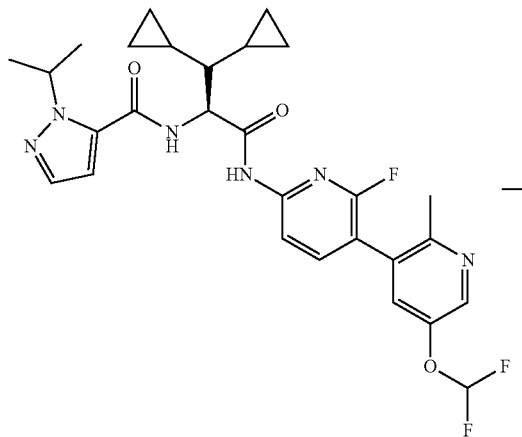

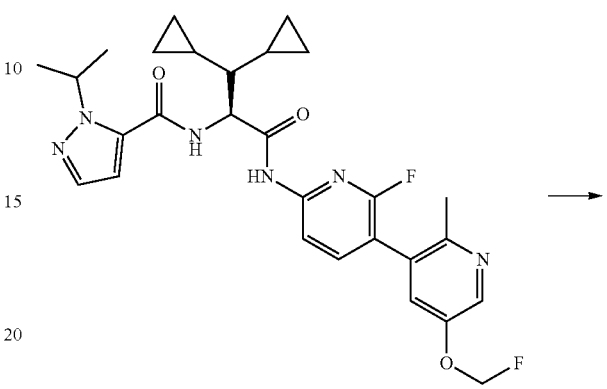

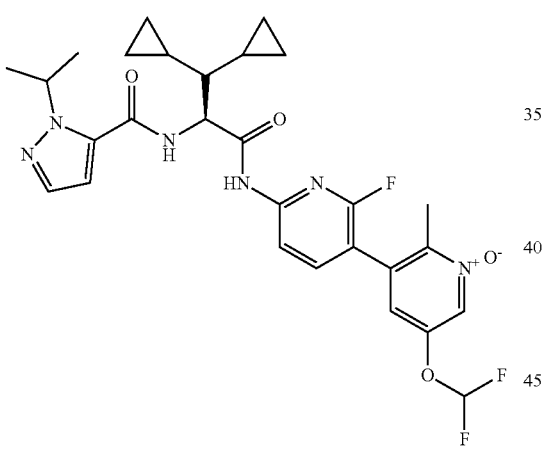

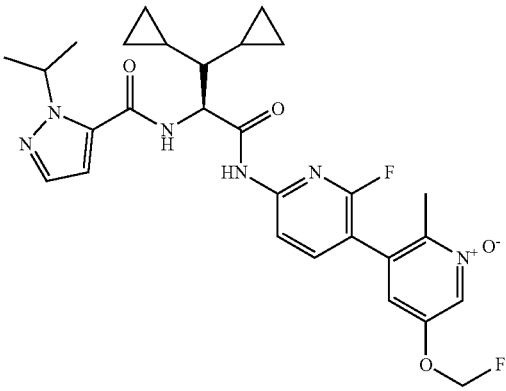

According to the Method of Example 1 the pyridine of Preparation 10 was oxidized to give the title compound (21 mg, 48%) as a colorless solid. LCMS (METHOD 4) (ES): m/z 573.6 [M+H]$^+$, RT=0.70 min; $^1$H NMR (400 MHZ, DMSO-d$_6$) δ 10.88 (s, 1H), 8.30-8.20 (m, 2H), 7.91 (dd, J=8.3, 1.9 Hz, 1H), 7.82 (dd, J=9.9, 8.2 Hz, 1H), 7.29 (d, J=1.9 Hz, 1H), 7.13 (t, J=72.9 Hz, 1H), 7.11 (d, J=2.3 Hz, 1H), 6.69 (d, J=2.0 Hz, 1H), 5.16 (hept, J=6.6 Hz, 1H), 4.68 (t, J=7.9 Hz, 1H), 1.98 (s, 3H), 1.16 (d, J=6.6 Hz, 3H), 1.12 (d, J=6.6 Hz, 3H), 0.83-0.71 (m, 1H), 0.71-0.59 (m, 1H), 0.54 (td, J=9.5, 7.4 Hz, 1H), 0.33-0.22 (m, 1H), 0.21--0.12 (m, 7H).

According to the Method of Example 1 the pyridine of Preparation 15 was oxidized to give the title compound (32 mg, 37%) as a colorless solid. LCMS (ES): m/z 555.254 [M+H]$^+$, RT=2.33 min; $^1$H NMR (600 MHz, DMSO-d$_6$) δ 11.10 (s, 1H), 8.49 (d, J=8.4 Hz, 1H), 8.38 (d, J=2.3 Hz, 1H), 8.13 (dd, J=8.2, 1.7 Hz, 1H), 8.05 (dd, J=10.0, 8.1 Hz, 1H), 7.52 (d, J=2.0 Hz, 1H), 7.25 (d, J=2.3 Hz, 1H), 6.92 (d, J=2.0 Hz, 1H), 5.94 (d, J=53.0 Hz, 2H), 5.39 (hept, J=6.6 Hz, 1H), 4.91 (t, J=8.0 Hz, 1H), 2.18 (s, 3H), 1.39 (d, J=6.6 Hz, 3H), 1.35 (d, J=6.6 Hz, 3H), 1.03-0.95 (m, 1H), 0.92-0.84 (m, 1H), 0.77 (td, J=9.5, 7.5 Hz, 1H), 0.54-0.46 (m, 1H), 0.44-0.36 (m, 1H), 0.36-0.19 (m, 5H), 0.19-0.12 (m, 1H).

Example 10: N-[(1S)-1-(dicyclopropylmethyl)-2-[[5-(5-ethoxy-2-methyl-1-oxido-pyridin-1-ium-3-yl)-6-fluoro-2-pyridyl]amino]-2-oxo-ethyl]-2-isopropyl-pyrazole-3-carboxamide

Example 11: N-[(1S)-1-[[5-(5-chloro-2-methyl-1-oxido-pyridin-1-ium-3-yl)-6-fluoro-2-pyridyl]carbamoyl]-2,2-dicyclopropyl-ethyl]-2-isopropyl-pyrazole-3-carboxamide

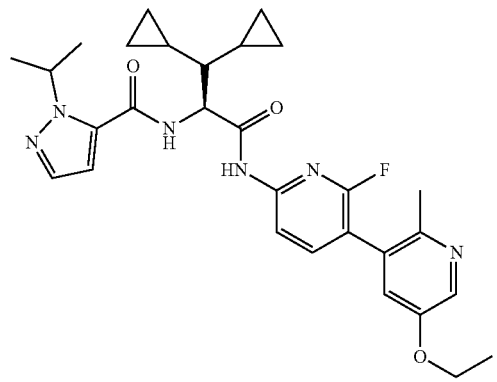

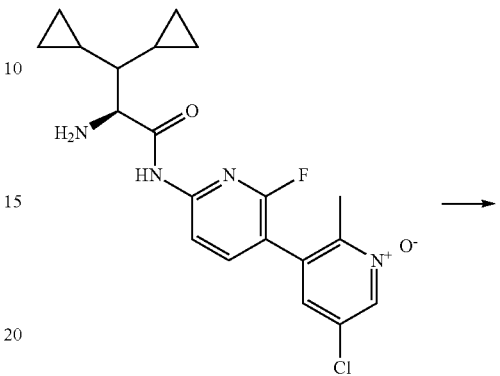

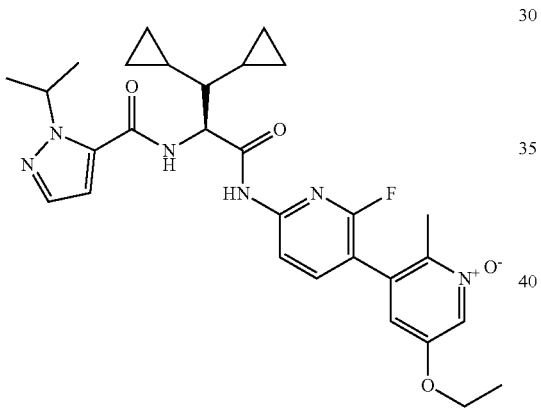

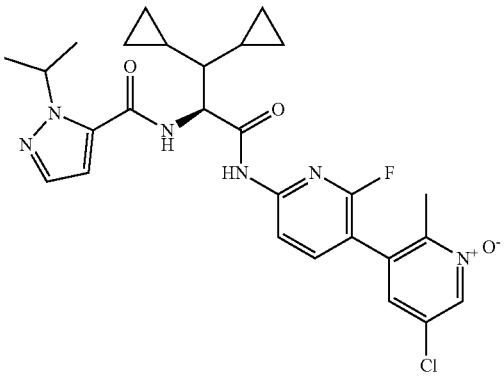

According to the Method of Example 1 the pyridine of Preparation 16 was oxidized to give the title compound (190 mg, 81%) as a colorless solid. LCMS (ES): m/z 551.278 [M+H]$^+$, RT=2.38 min; $^1$H NMR (600 MHZ, DMSO-d$_6$) δ 10.85 (s, 1H), 8.25 (d, J=8.4 Hz, 1H), 7.97 (d, J=2.3 Hz, 1H), 7.89 (dd, J=8.2, 1.7 Hz, 1H), 7.79 (dd, J=10.0, 8.2 Hz, 1H), 7.28 (d, J=1.9 Hz, 1H), 6.81 (d, J=2.3 Hz, 1H), 6.69 (d, J=2.0 Hz, 1H), 5.15 (hept, J=6.6 Hz, 1H), 4.68 (t, J=8.0 Hz, 1H), 3.88 (q, J=7.0 Hz, 2H), 1.91 (s, 3H), 1.15 (d, J=6.6 Hz, 3H), 1.12 (d, J=6.6 Hz, 3H), 1.09 (t, J=7.0 Hz, 3H), 0.80-0.71 (m, 1H), 0.69-0.61 (m, 1H), 0.53 (td, J=9.5, 7.5 Hz, 1H), 0.30-0.22 (m, 1H), 0.20-0.13 (m, 1H), 0.12--0.04 (m, 5H), −0.04--0.11 (m, 1H).

HATU (153 mg, 0.40 mmol) was added to a solution of the compound of Preparation 23 (300 mg, 0.33 mmol, approx. 50% pure), 2-isopropylpyrazole-3-carboxylic acid (50.3 mg, 0.33 mmol) and DIPEA (0.17 mL, 0.98 mmol) in DMF (5 mL) at 0° C. The reaction mixture was stirred and allowed to warm to room temperature over 1 hour. The reaction mixture was quenched with H$_2$O (20 mL) and extracted with EtOAc (2×50 mL). The combined organic phase was dried over Na$_2$SO$_4$, filtered, and concentrated in vacuo. The obtained crude compound was purified by prep. acidic HPLC to afford the title compound (29 mg, 16% yield) as a colorless solid. LCMS (ESI): m/z 541.213 [M+H]$^+$, RT=2.39 min; $^1$H NMR (400 MHZ, DMSO-d$_6$) δ=11.11 (s, 1H), 8.67 (d, J=1.6 Hz, 1H), 8.49 (d, J=8.4 Hz, 1H), 8.15-8.10 (m, 1H), 8.09-8.01 (m, 1H), 7.56 (d, J=1.6 Hz, 1H), 7.51 (d, J=1.8 Hz, 1H), 6.92 (d, J=1.9 Hz, 1H), 5.38 (td, J=6.6, 13.2 Hz, 1H), 4.90 (t, J=7.9 Hz, 1H), 2.20 (s, 3H), 1.38 (d, J=6.6 Hz, 3H), 1.34 (d, J=6.6 Hz, 3H), 1.05-0.93 (m, 1H), 0.92-0.82 (m, 1H), 0.81-0.71 (m, 1H), 0.54-0.44 (m, 1H), 0.44-0.10 (m, 7H); Chiral HPLC: 96.85% (RT: 2.22 min), Column: (R,R) WHELK-01 (4.6*150 mm) 3.5 μm, Co-Solvent: 0.5% DEA in Methanol, Column Temperature: 30° ° C., Flow: 3 mL/min, ABPR: 1500 psi.

Example 12: N-[(1S)-1-(dicyclopropylmethyl)-2-[[6-fluoro-5-[2-methyl-1-oxido-5-(trifluoromethyl)pyridin-1-ium-3-yl]-2-pyridyl]amino]-2-oxo-ethyl]-2-isopropyl-pyrazole-3-carboxamide Example 13: N-[(1S)-2,2-dicyclopropyl-1-[[5-(2-cyclopropyl-5-methyl-1-oxido-pyridin-1-ium-3-yl)-6-fluoro-2-pyridyl]carbamoyl]ethyl]-2-isopropyl-pyrazole-3-carboxamide

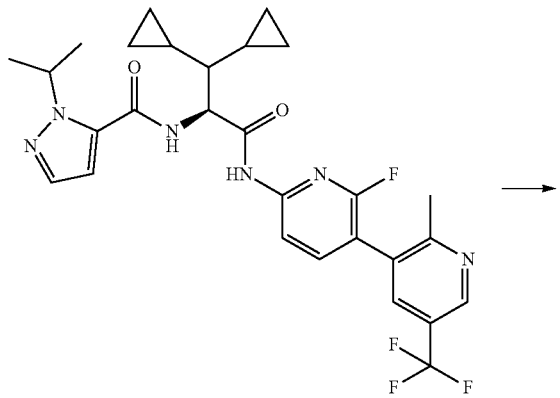

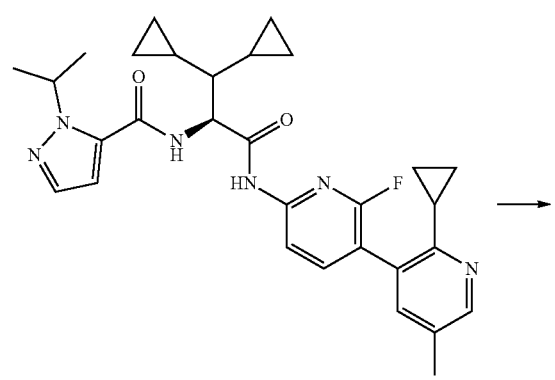

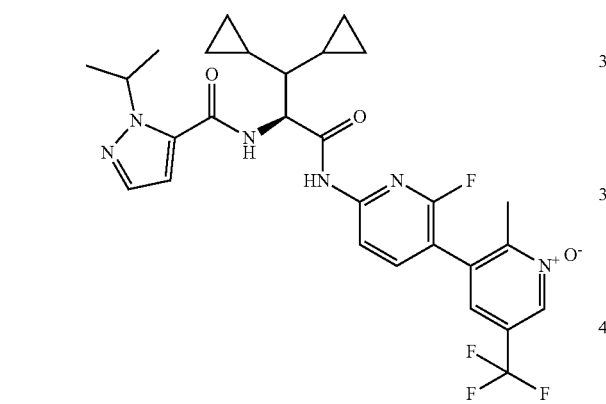

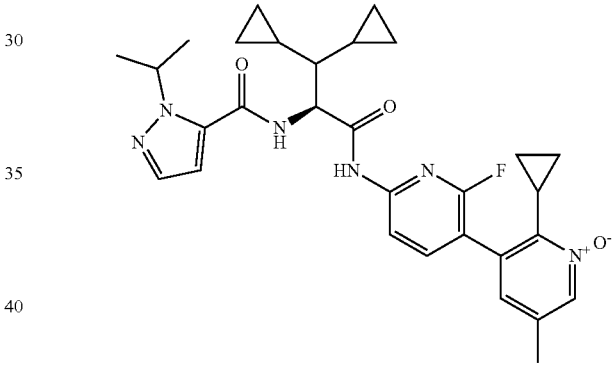

According to the method of Example 1 the compound of Preparation 27 (80.0 mg, 0.14 mmol) was reacted with mCPBA (50.6 mg, 0.21 mmol) to afford the title compound (23 mg, 29% yield) after prep. acidic HPLC. LCMS (METHOD 2) (ESI): m/z 575.31 [M+H]$^+$, RT=2.02 min, Column: (Acquity BEH C18 (50 mm×2.1 mm, 1.7 μm); 0.05% TFA in water with MeCN); $^1$H NMR (400 MHZ, DMSO-d$_6$) δ=11.12 (s, 1H), 8.90 (s, 1H), 8.52-8.45 (m, 1H), 8.17-8.04 (m, 2H), 7.77 (s, 1H), 7.54-7.48 (m, 1H), 6.92 (d, J=1.9 Hz, 1H), 5.38 (quin, J=6.6 Hz, 1H), 4.91 (t, J=7.9 Hz, 1H), 2.30 (s, 3H), 1.38 (d, J=6.5 Hz, 3H), 1.35 (d, J=6.6 Hz, 3H), 1.05-0.94 (m, 1H), 0.93-0.82 (m, 1H), 0.81-0.71 (m, 1H), 0.54-0.44 (m, 1H), 0.43-0.10 (m, 7H); Chiral HPLC: 99.84% (RT: 1.73 min); Column: (R,R) WHELK-01 (4.6*150 mm) 3.5 μm, Co-Solvent: 0.5% DEA in Methanol, Column Temperature: 30° ° C., Flow: 3 mL/min, ABPR: 1500 psi.

According to the method of Example 1 the compound of Preparation 32 (70.0 mg, 0.13 mmol) was reacted with mCPBA (32.6 mg, 0.13 mmol) to afford the title compound (33 mg, 45% yield) after prep. acidic HPLC. LCMS (ESI): m/z 547.283 [M+H]$^+$, RT=2.33 min; $^1$H NMR (400 MHZ, DMSO-d$_6$) δ=11.06 (s, 1H), 8.49 (d, J=8.5 Hz, 1H), 8.22 (s, 1H), 8.14-8.08 (m, 1H), 8.06-7.96 (m, 1H), 7.52 (d, J=1.9 Hz, 1H), 7.16 (s, 1H), 6.93 (d, J=2.0 Hz, 1H), 5.39 (td, J=6.6, 13.3 Hz, 1H), 4.90 (t, J=7.9 Hz, 1H), 2.25 (s, 3H), 1.84-1.74 (m, 1H), 1.38 (d, J=6.6 Hz, 3H), 1.35 (d, J=6.6 Hz, 3H), 1.03-0.93 (m, 1H), 0.92-0.82 (m, 1H), 0.81-0.69 (m, 3H), 0.54-0.45 (m, 1H), 0.44-0.07 (m, 9H); Chiral HPLC: 99.08% (RT: 1.91 min), Column: (R,R)WHELK-01 (4.6*150 mm) 5 μm, Co-Solvent: 0.5% DEA in Methanol, Column Temperature: 30° C., Flow: 3 ml/min, ABPR: 1500 psi.

Example 14: N-[(1S)-2,2-dicyclopropyl-1-[[5-(5-cyclopropyl-2-methyl-1-oxido-pyridin-1-ium-3-yl)-6-fluoro-2-pyridyl]carbamoyl]ethyl]-2-isopropyl-pyrazole-3-carboxamide and N-[(1S)-2,2-dicyclopropyl-1-[[5-(5-cyclopropyl-6-methyl-1-oxido-pyridin-1-ium-3-yl)-6-fluoro-2-pyridyl]carbamoyl]ethyl]-2-isopropyl-pyrazole-3-carboxamide

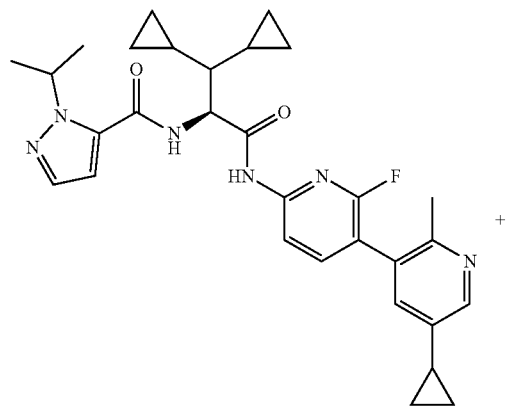

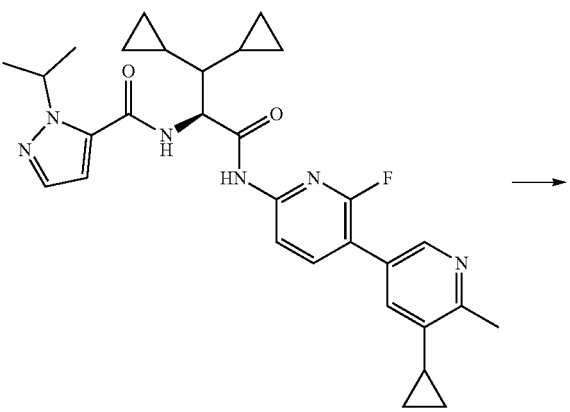

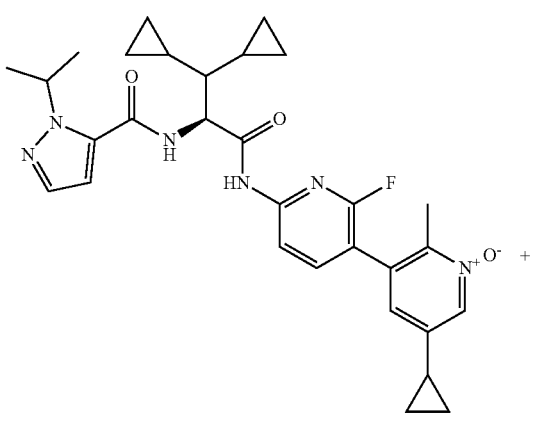

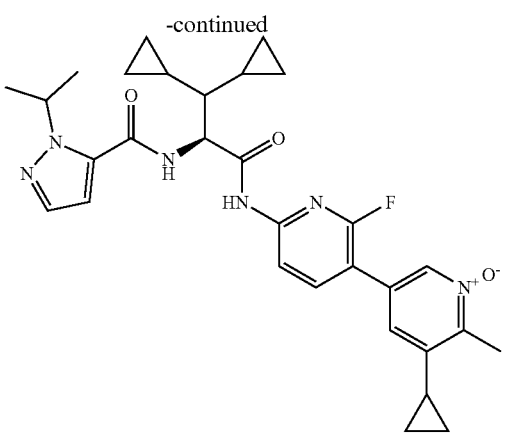

According to the method of Example 1 the compounds of Preparation 37 (200 mg, 0.38 mmol) were reacted with mCPBA (97.3 mg, 0.38 mmol) to afford the separated title compounds after prep. acidic HPLC (XBRIDGE 19×250 mm, 5 μm, 0.10% Formic acid in Water/MeCN).

Example 14a: N-[(1S)-2,2-dicyclopropyl-1-[[5-(5-cyclopropyl-2-methyl-1-oxido-pyridin-1-ium-3-yl)-6-fluoro-2-pyridyl]carbamoyl]ethyl]-2-isopropyl-pyrazole-3-carboxamide: (33 mg, 16% yield). LCMS (METHOD 2) (ESI): m/z 547.49 [M+H]$^+$, RT=5.35 min, Column: (Acquity BEH C18 (50 mm×2.1 mm, 1.7 μm) 0.05% FA in water with MeCN); $^1$H NMR (400 MHZ, DMSO-d$_6$) δ=11.10 (br s, 1H), 8.52 (d, J=8.4 Hz, 1H), 8.25 (s, 1H), 8.11 (d, J=7.9 Hz, 1H), 8.05-7.97 (m, 1H), 7.52 (s, 1H), 7.01 (s, 1H), 6.93 (s, 1H), 5.38 (td, J=6.6, 13.1 Hz, 1H), 4.90 (t, J=7.8 Hz, 1H), 2.17 (s, 3H), 1.98-1.89 (m, 1H), 1.38 (d, J=6.5 Hz, 3H), 1.34 (d, J=6.6 Hz, 3H), 0.99 (d, J=6.3 Hz, 3H), 0.92-0.70 (m, 4H), 0.56-0.43 (m, 1H), 0.43-0.08 (m, 7H); Chiral HPLC: 99.92% (RT: 3.52 min), Column: (R,R) WHELK-01 (4.6*250 mm) 5 μm, Co-Solvent: 0.5% DEA in Methanol, Column Temperature: 30° C., Flow: 4 mL/min, ABPR: 1500 psi.

Example 14b: N-[(1S)-2,2-dicyclopropyl-1-[[5-(5-cyclopropyl-6-methyl-1-oxido-pyridin-1-ium-3-yl)-6-fluoro-2-pyridyl]carbamoyl]ethyl]-2-isopropyl-pyrazole-3-carboxamide. 34 mg, 16% yield). LCMS (METHOD 2) (ESI): m/z 547.45 [M+H]$^+$, RT=5.41 min, Column: (Acquity BEH C18 (50 mm×2.1 mm, 1.7 μm) 0.05% FA in water with MeCN); $^1$H NMR (400 MHZ, DMSO-d$_6$) δ=11.09 (br s, 1H), 8.51 (br d, J=8.5 Hz, 1H), 8.41 (s, 1H), 8.23 (dd, J=8.4, 10.2 Hz, 1H), 8.09 (d, J=7.4 Hz, 1H), 7.51 (d, J=1.8 Hz, 1H), 7.18 (s, 1H), 6.93 (d, J=1.9 Hz, 1H), 5.38 (td, J=6.6, 13.2 Hz, 1H), 4.90 (t, J=7.9 Hz, 1H), 2.54 (s, 3H), 2.09-2.00 (m, 1H), 1.38 (d, J=6.6 Hz, 3H), 1.34 (d, J=6.6 Hz, 3H), 1.05-0.92 (m, 3H), 0.91-0.81 (m, 1H), 0.80-0.69 (m, 3H), 0.54-0.43 (m, 1H), 0.43-0.34 (m, 1H), 0.34-0.08 (m, 6H); Chiral HPLC: 96.22% (RT: 4.34 min), Column: (R,R)WHELK-01 (4.6*250 mm) 5 μm, Co-Solvent: 0.5% DEA in Methanol, Column Temperature: 30° C., Flow: 4 mL/min, ABPR: 1500 psi.

Example 15: N-[(1S)-1-(dicyclopropylmethyl)-2-[[6-fluoro-5-(4-methyl-1-oxido-pyridin-1-ium-3-yl)-2-pyridyl]amino]-2-oxo-ethyl]-2-isopropyl-pyrazole-3-carboxamide

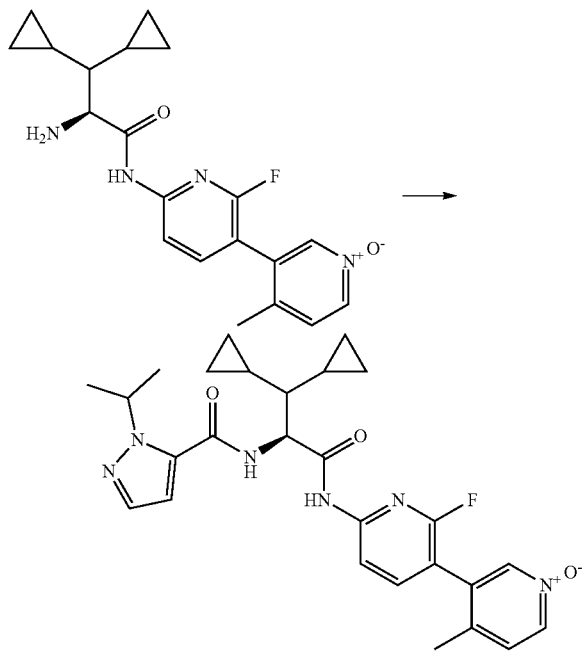

According to the method of Example 11 the compound of Preparation 40 (200 mg, 0.35 mmol) was reacted with 2-isopropylpyrazole-3-carboxylic acid (54.1 mg, 0.35 mmol) to afford the title compound (10 mg, 5% yield) after prep. acidic HPLC as an off-white solid. LCMS (ESI): m/z 507.253 [M+H]$^+$, RT=2.22 min; $^1$H NMR (400 MHZ, DMSO-d$_6$) δ=11.08 (s, 1H), 8.49 (d, J=8.4 Hz, 1H), 8.26 (s, 1H), 8.22 (d, J=6.5 Hz, 1H), 8.14-8.07 (m, 1H), 8.06-7.98 (m, 1H), 7.51 (d, J=1.5 Hz, 1H), 7.42 (d, J=6.5 Hz, 1H), 6.92 (d, J=1.6 Hz, 1H), 5.38 (td, J=6.4, 13.1 Hz, 1H), 4.90 (t, J=7.8 Hz, 1H), 2.14 (s, 3H), 1.38 (d, J=6.5 Hz, 4H), 1.34 (d, J=6.6 Hz, 3H), 1.05-0.92 (m, 1H), 0.92-0.82 (m, 1H), 0.81-0.71 (m, 1H), 0.54-0.44 (m, 1H), 0.44-0.10 (m, 7H); Chiral HPLC: 93.48% (RT: 3.66 min), Column: (R,R) WHELK-01 (4.6*150 mm) 3.5 μm, Co-Solvent: 0.5% DEA in Methanol, Column Temperature: 30° C., Flow: 3 mL/min, ABPR: 1500 psi.

Example 16: N-[(1S)-1-(dicyclopropylmethyl)-2-[[6-fluoro-5-(2-methyl-1-oxido-pyridin-1-ium-3-yl)-2-pyridyl]amino]-2-oxo-ethyl]-2-isopropyl-pyrazole-3-carboxamide

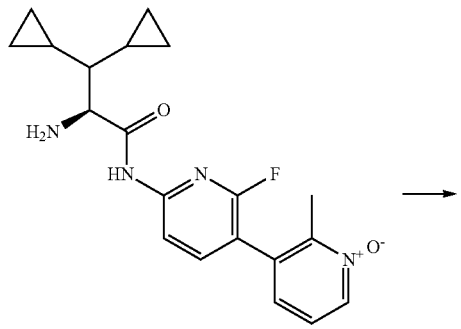

-continued

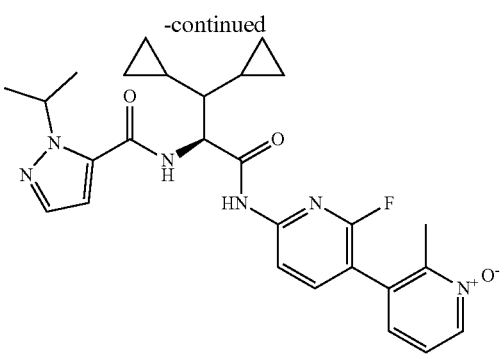

According to the method of Example 11 the compound of Preparation 43 (150 mg, 0.26 mmol) was reacted with 2-isopropylpyrazole-3-carboxylic acid (48.7 mg, 0.32 mmol) to afford the title compound (9 mg, 6% yield) after prep. acidic HPLC as an off-white solid. LCMS (ESI): m/z 507.252 [M+H]$^+$, RT=2.24 min; $^1$H NMR (400 MHZ, DMSO-d$_6$) δ=11.08 (s, 1H), 8.49 (d, J=8.5 Hz, 1H), 8.38 (d, J=6.5 Hz, 1H), 8.13 (d, J=8.0 Hz, 1H), 8.03 (d, J=8.0 Hz, 1H), 7.52 (d, J=1.5 Hz, 1H), 7.43-7.37 (m, 1H), 7.36-7.30 (m, 1H), 6.92 (d, J=1.5 Hz, 1H), 5.39 (td, J=6.5, 13.0 Hz, 1H), 4.91 (t, J=7.8 Hz, 1H), 2.24 (s, 3H), 1.39 (d, J=6.5 Hz, 3H), 1.35 (d, J=6.5 Hz, 3H), 1.06-0.93 (m, 1H), 0.91-0.82 (m, 1H), 0.81-0.72 (m, 1H), 0.55-0.45 (m, 1H), 0.44-0.08 (m, 7H); Chiral HPLC: 94.45% (RT: 4.23 min), Column: (R,R)WHELK-01 (4.6*150 mm) 3.5 μm, Co-Solvent: 0.5% DEA in Methanol, Column Temperature: 30° ° C., Flow: 3 mL/min, ABPR: 1500 psi.

Example 18: N-[(1S)-1-[[6-chloro-5-(2,5-dimethyl-1-oxido-pyridin-1-ium-3-yl)-2-pyridyl]carbamoyl]-2,2-dicyclopropyl-ethyl]-2-isopropyl-pyrazole-3-carboxamide

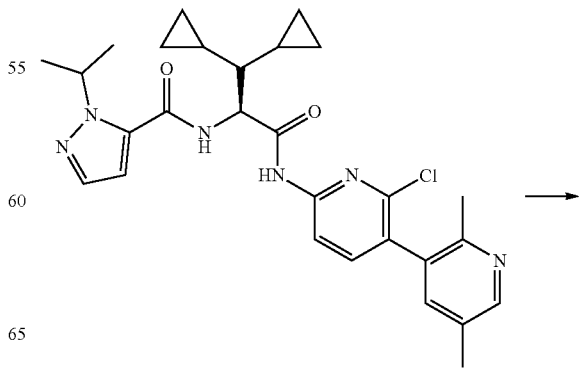

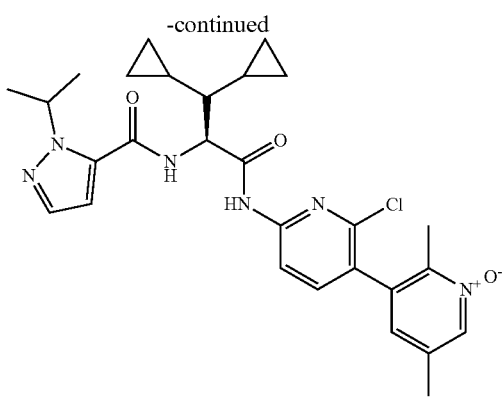

According to the Method of Example 1 the pyridine of Preparation 46 was oxidized to give the title compound (188 mg, 66%) as a colorless solid as a mixture of atropisomers. LCMS (ES): m/z 537.238 [M+H]$^+$, RT=2.34 min; $^1$H NMR (600 MHz, DMSO-d$_6$) δ 10.97 and 10.94 (s, 1H), 8.31-8.18 (m, 1H), 8.05 (s, 1H), 7.99-7.88 (m, 1H), 7.71-7.56 (m, 1H), 7.33-7.22 (m, 1H), 6.95-6.83 (m, 1H), 6.73-6.63 (m, 1H), 5.21-5.10 (m, 1H), 4.71-4.65 (m, 1H), 2.04 (2×s, 3H), 1.90 and 1.89 (2×s, 3H), 1.16 (d, J=6.6 Hz, 3H), 1.12 (2×d, J=6.6 Hz, 3H), 0.81-0.72 (m, 1H), 0.69-0.61 (m, 1H), 0.59-0.50 (m, 1H), 0.30-0.23 (m, 1H), 0.20-0.12 (m, 1H), 0.12--0.10 (m, 6H).

Example 19: N-[(1S)-1-[[6-chloro-5-(5-fluoro-2-methyl-1-oxido-pyridin-1-ium-3-yl)-2-pyridyl]carbamoyl]-2,2-dicyclopropyl-ethyl]-2-isopropyl-pyrazole-3-carboxamide

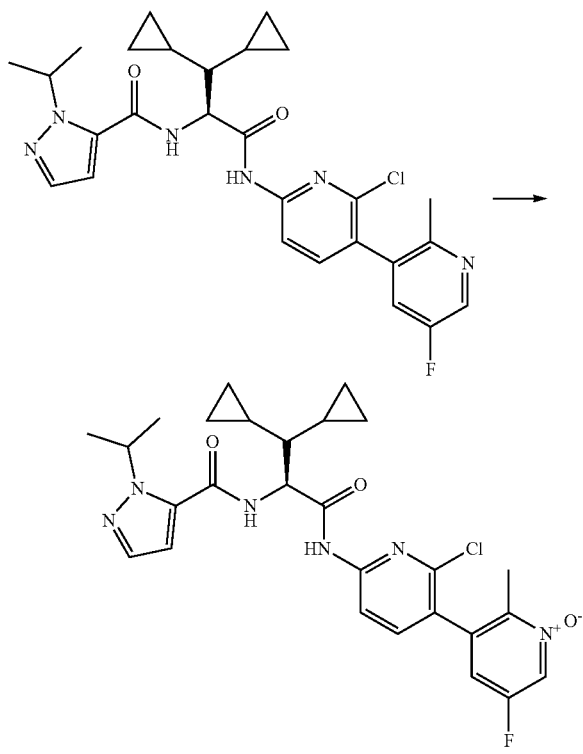

mg, 36%) as a colorless solid as a mixture of atropisomers. LCMS (ES): m/z 541.213 [M+H]$^+$, RT=2.37 min; $^1$H NMR (600 MHz, DMSO-d$_6$) δ 11.00 and 10.96 (2×s, 1H), 10.96, 8.51-8.42 (m, 1H), 8.30-8.19 (m, 1H), 7.99-7.93 (m, 1H), 7.72-7.67 (m, 1H), 7.30-7.26 (m, 1H), 7.24-7.17 (m, 1H), 6.71-6.67 (m, 1H), 5.19-5.10 (m, 1H), 4.71-4.64 (m, 1H), 1.89 and 1.88 (2×s, 3H), 1.15 (d, J=6.6 Hz, 3H), 1.11 (2×d, J=6.6 Hz, 3H), 0.81-0.72 (m, 1H), 0.69-0.60 (m, 1H), 0.57-0.50 (m, 1H), 0.30-0.22 (m, 1H), 0.20-0.12 (m, 1H), 0.11--0.10 (m, 6H).

Example 20: N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-propyl-pyrazole-3-carboxamide

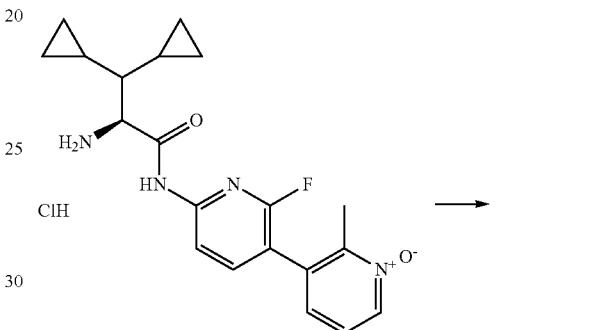

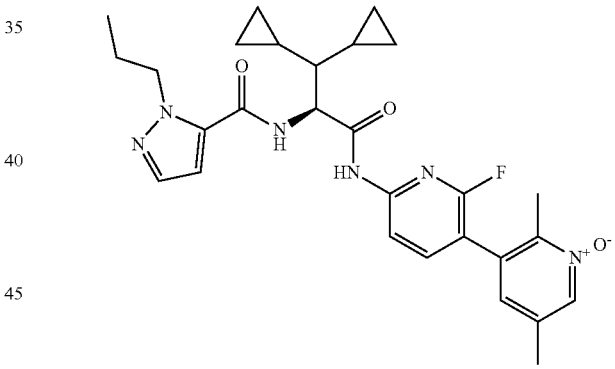

Solution A was prepared by adding DIPEA (0.23 mL, 171 mg, 1.32 mmol) to a solution of the compound of Preparation 53 (190 mg, 0.45 mmol) in DMF (4.50 mL). Solution B was prepared by dissolving HATU (180 mg, 0.47 mmol) in DMF (4.5 mL). Solution A (0.25 mL) was added to propanoic acid (4.3 mg, 0.028 mmol) followed by solution B (0.25 mL) and the mixture was shaken at room temperature for 1 hour. The crude reaction mixture was purified by basic prep. HPLC to give the title compound (7.3 mg, 56% Yield). LCMS (ES): m/z 521.267 [M+H]$^+$, RT=2.31 min; $^1$H NMR (400 MHZ, DMSO-d$_6$) δ 11.05 (s, 1H), 8.48 (d, J=8.5 Hz, 1H), 8.27 (s, 1H), 8.11 (dd, J=8.1, 1.8 Hz, 1H), 8.00 (dd, J=10.0, 8.2 Hz, 1H), 7.49 (d, J=2.0 Hz, 1H), 7.17 (s, 1H), 6.99 (d, J=2.0 Hz, 1H), 4.91 (t, J=8.0 Hz, 1H), 4.50-4.31 (m, 2H), 2.26 (s, 3H), 2.18 (s, 3H), 1.71 (h, J=7.3 Hz, 2H), 1.04-0.92 (m, 1H), 0.92-0.81 (m, 1H), 0.81-0.73 (m, 4H), 0.54-0.44 (m, 1H), 0.44-0.34 (m, 1H), 0.34-0.09 (m, 6H).

According to the Method of Example 1 the pyridine of Preparation 47 was oxidized to give the title compound (13

Example 21: 2-tert-butyl-N-[(1S)-1-(dicyclopropyl-methyl)-2-[[5-(2,5-dimethyl-1-oxido-pyridin-1-ium-3-yl)-6-fluoro-2-pyridyl]amino]-2-oxo-ethyl]pyrazole-3-carboxamide

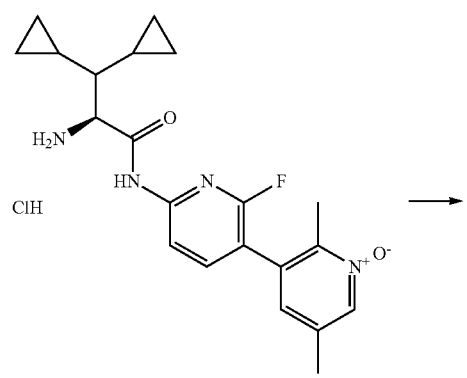

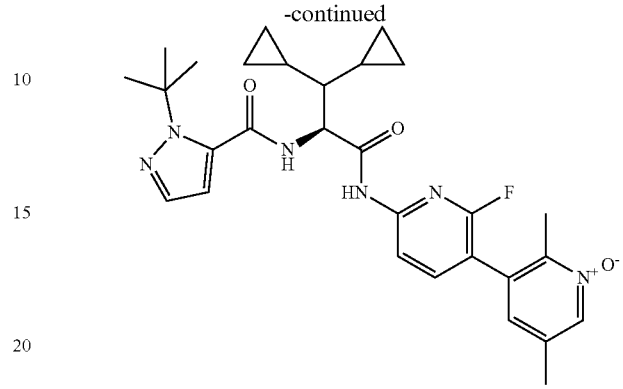

According to the method of Example 20 the compound of Preparation 53 (0.025 mmol) was reacted with 2-tert-butylpyrazole-3-carboxylic acid to give the title compound (3.1 mg, 23%). $^1$H NMR (400 MHZ, DMSO-$d_6$) Y 10.99 (s, 1H), 8.77 (d, J=8.4 Hz, 1H), 8.28 (s, 1H), 8.13-8.08 (m, 1H), 8.01 (dd, J=10.0, 8.2 Hz, 1H), 7.40 (d, J=1.8 Hz, 1H), 7.18 (s, 1H), 6.49 (d, J=1.9 Hz, 1H), 4.94-4.80 (m, 1H), 2.27 (s, 3H), 2.19 (s, 3H), 1.59 (s, 9H), 1.09-0.97 (m, 1H), 0.94-0.82 (m, 1H), 0.79-0.68 (m, 1H), 0.56-0.45 (m, 1H), 0.44-0.28 (m, 2H), 0.28-0.15 (m, 5H).

Examples 22 to 46

Examples 22 to 46 were synthesized according to the method of Example 20 from the compound of Preparation 53 and the appropriate carboxylic acid. The required carboxylic acids are either commercially available or their synthesis is described in WO2020127685 or WO2021250194.

| Example Number | Name | Structure | LCMS details |
|---|---|---|---|
| 22 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-isopropyl-isoxazole-4-carboxamide | 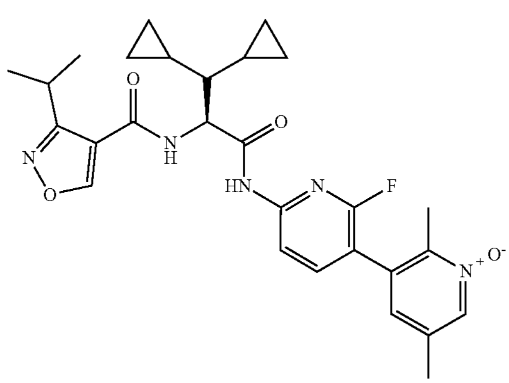 | (ES): m/z 522.251 [M + H]$^+$, RT = 2.35 min |

-continued

| Example Number | Name | Structure | LCMS details |
|---|---|---|---|
| 23 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-isopropyl-triazole-4-carboxamide | 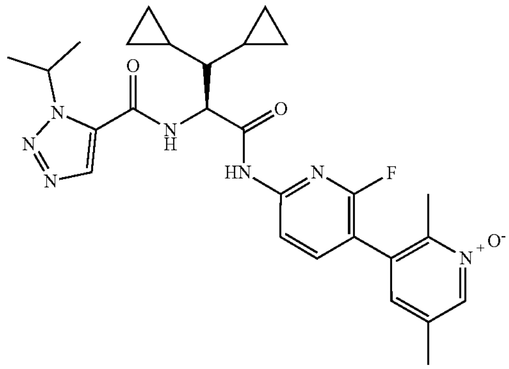 | (ES): m/z 522.262 [M + H]⁺, RT = 2.24 min |
| 24 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(2,2-difluoroethyl)pyrazole-3-carboxamide | 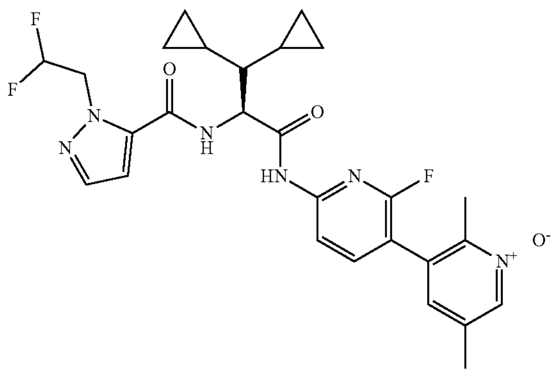 | (ES): m/z 543.233 [M + H]⁺, RT = 2.28 min |
| 25 | 2-cyclobutyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide | 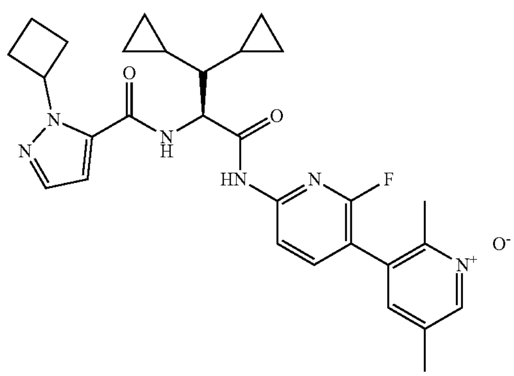 | (ES): m/z 533.268 [M + H]⁺, RT = 2.37 min |
| 26 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(difluoromethyl)pyrazole-3-carboxamide | 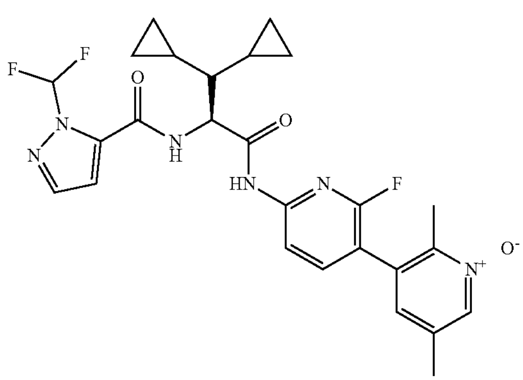 | (ES): m/z 529.217 [M + H]⁺, RT = 2.29 min |

| Example Number | Name | Structure | LCMS details |
|---|---|---|---|
| 27 | 2-cyclopropyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide | 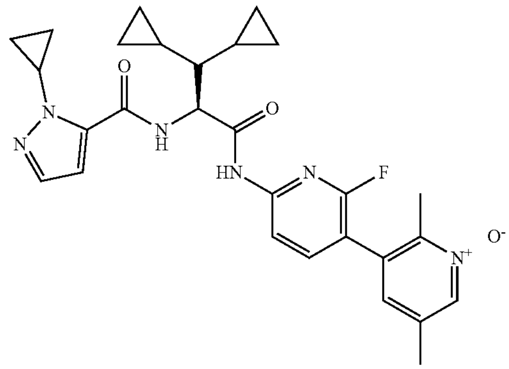 | (ES): m/z 519.252 [M + H]+, RT = 2.26 min |
| 28 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-isobutyl-pyrazole-3-carboxamide | 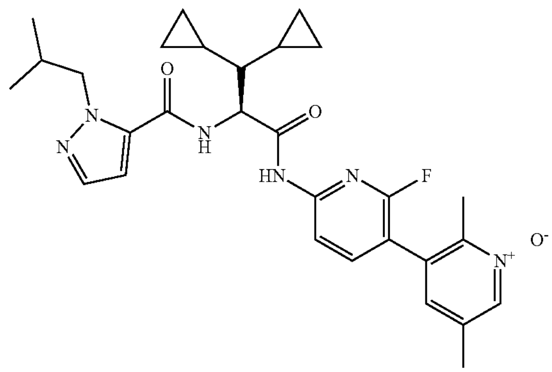 | (ES): m/z 535.283 [M + H]+, RT = 2.38 min |
| 29 | 2-(cyclopropylmethyl)-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide | 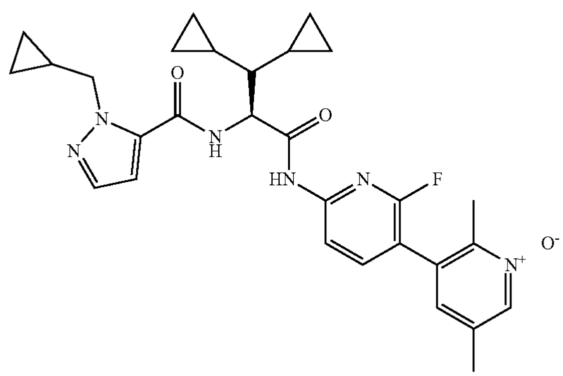 | (ES): m/z 533.268 [M + H]+, RT = 2.33 min |
| 30 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(3-hydroxybutyl)pyrazole-3-carboxamide | 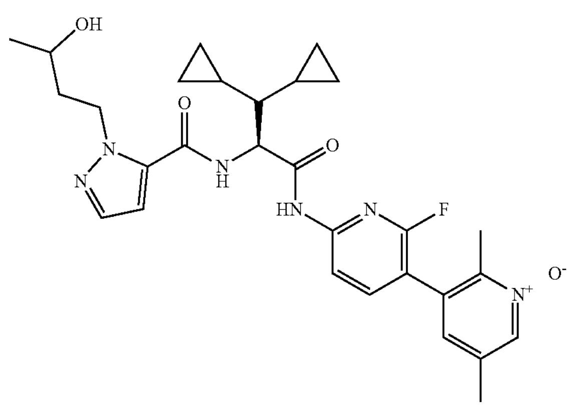 | (ES): m/z 549.4 [M − H]−, RT = 0.62 min (METHOD 4) |

-continued

| Example Number | Name | Structure | LCMS details |
|---|---|---|---|
| 31 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(4,4,4-trifluoro-3-hydroxy-butyl)pyrazole-3-carboxamide | 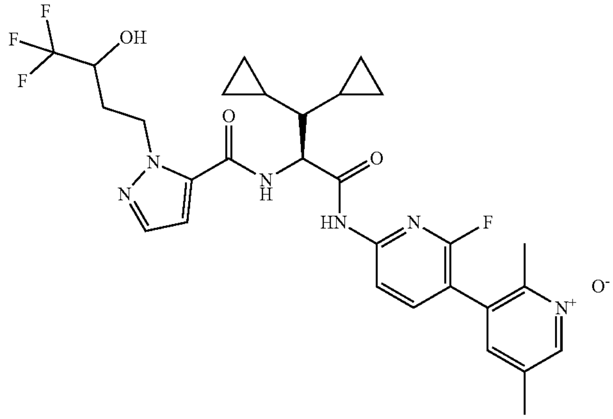 | (ES): m/z 603.3 [M − H]⁻, RT = 0.68 min (METHOD 4) |
| 32 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[(3,3-difluorocyclobutyl)methyl]-pyrazole-3-carboxamide | 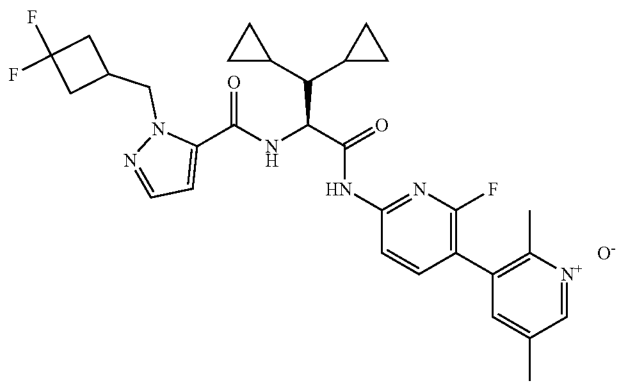 | (ES): m/z 583.264 [M + H]⁺, RT = 2.39 min |
| 33 | 4-cyclopropyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-1,2,5-oxadiazole-3-carboxamide | 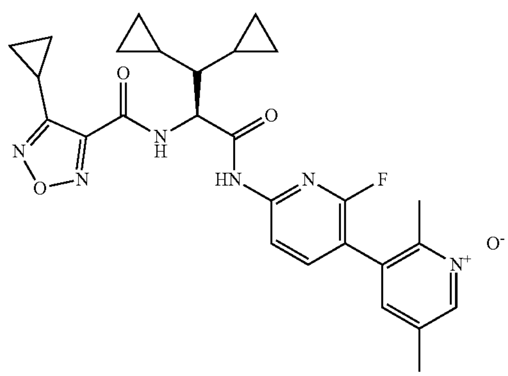 | (ESI): m/z 521.4 [M + H]⁺, RT = 2.06 min. (Acquity BEH C18 (50 mm × 2.1 mm), 0.05% FA in MeCN, 0.05 % FA in H₂O) (METHOD 2) |
| 34 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(3-hydroxypropyl)pyrazole-3-carboxamide | 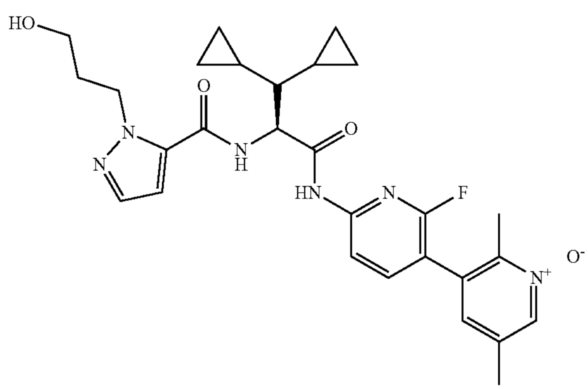 | (ESI): m/z 537.4 [M + H]⁺, RT = 1.64 min. (Acquity BEH C18 (50 mm × 2.1 mm), 0.05% FA in MeCN, 0.05 % FA in H₂O) (METHOD 2) |

-continued

| Example Number | Name | Structure | LCMS details |
|---|---|---|---|
| 35 | Diastereomer 1 of N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(2,2-difluoro-1-methyl-ethyl)pyrazole-3-carboxamide | 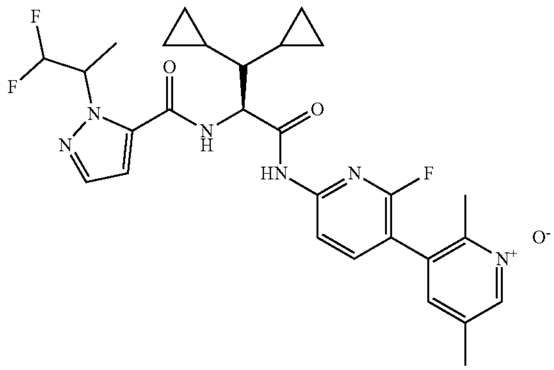 | (ES): m/z 557.249 [M + H]+, RT = 2.36 min |
| 36 | Diastereomer 2 of N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(2,2-difluoro-1-methyl-ethyl)pyrazole-3-carboxamide | 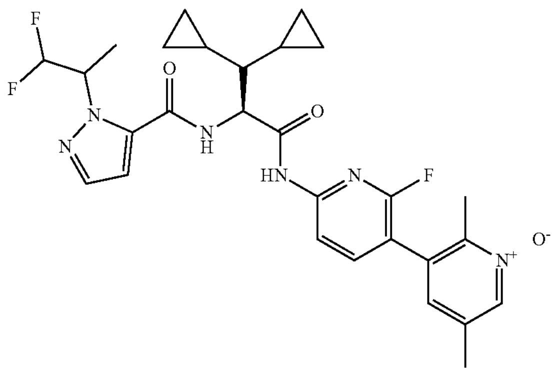 | (ES): m/z 557.249 [M + H]+, RT = 2.35 min |
| 37 | N-[(1S)-1-(dicyclopropylmethyl)-2-[5-(2,5-dimethyl-1-oxido-pyridin-1-ium-3-yl)-6-fluoro-2-pyridyl]amino]-2-oxo-ethyl]-2-[2-fluoro-1-(fluoromethyl)ethyl]-pyrazole-3-carboxamide | 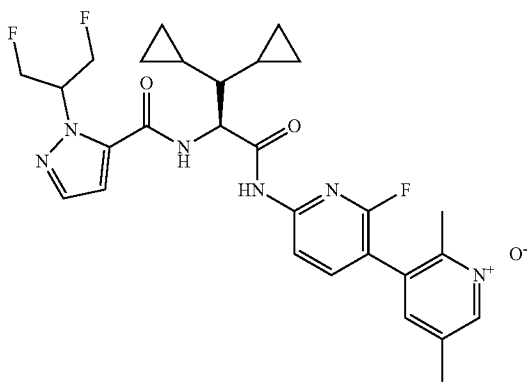 | (ES): m/z 557.249 [M + H]+, RT = 2.30 min |
| 38 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-methyl-isoxazole-4-carboxamide | 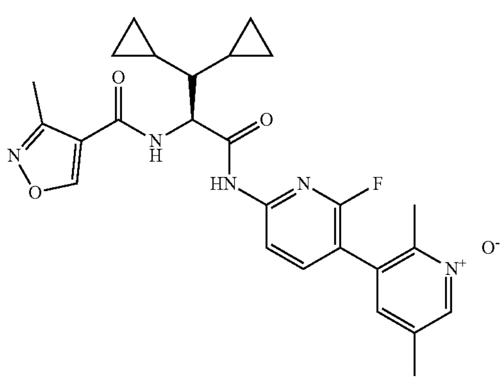 | (ES): m/z 494.220 [M + H]+, RT = 2.21 min |

| Example Number | Name | Structure | LCMS details |
|---|---|---|---|
| 39 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-ethyl-isoxazole-4-carboxamide | 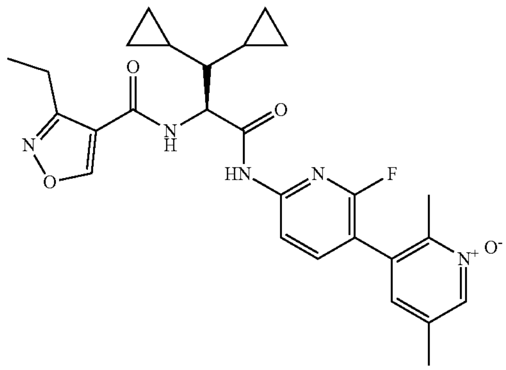 | (ES): m/z 508.236 [M + H]+, RT = 2.28 min |
| 40 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-4-methyl-1,2,5-oxadiazole-3-carboxamide | 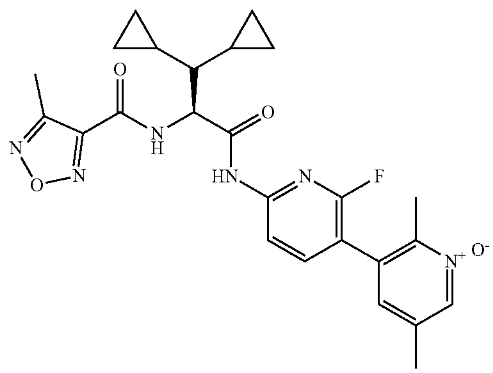 | (ES): m/z 495.216 [M + H]+, RT = 2.37 min |
| 41 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-ethyl-pyrazole-3-carboxamide | 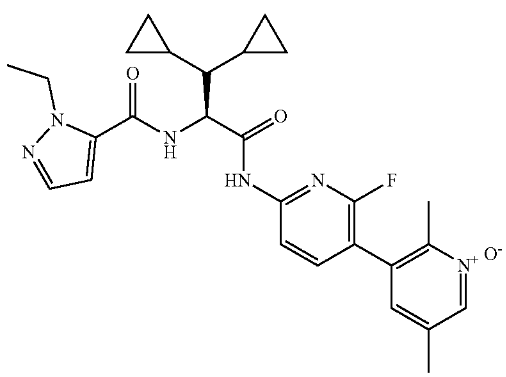 | (ES): m/z 507.252 [M + H]+, RT = 2.24 min |
| 42 | N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-methyl-pyrazole-3-carboxamide | 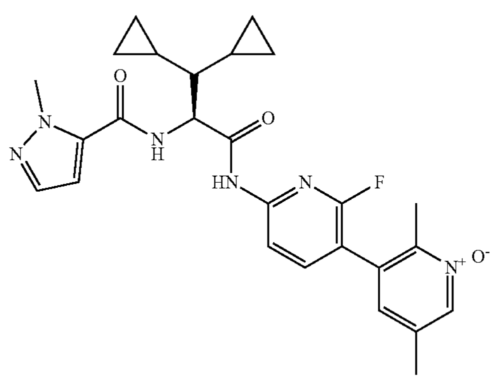 | (ES): m/z 493.236 [M + H]+, RT = 2.18 min |

Examples 47 to 53

Example 47 to 53 and 60 were synthesized according to the method of Example 1 from the pyridines of the indicated Preparations.

| Example number | Name | Structure | Precursor Prep. No. | LCMS details |
|---|---|---|---|---|
| 47 | N-[(1S)-2,2-dicyclopropyl-1-[[5-(4-cyclopropyl-1-oxido-pyridin-1-ium-3-yl)-6-fluoro-2-pyridyl]carbamoyl]ethyl]-2-isopropyl-pyrazole-3-carboxamide | 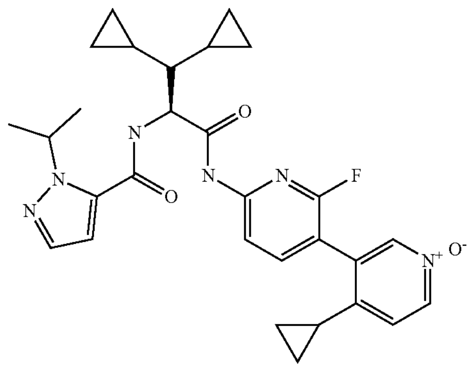 | 54 | (ES): m/z 533.268 [M + H]+, RT = 2.31 min |
| 48 | N-[(1S)-1-(dicyclopropyl-methyl)-2-[[5-[5-(difluoromethyl)-4-methyl-1-oxido-pyridin-1-ium-3-yl]-6-fluoro-2-pyridyl]amino]-2-oxo-ethyl]-2-isopropyl-pyrazole-3-carboxamide | 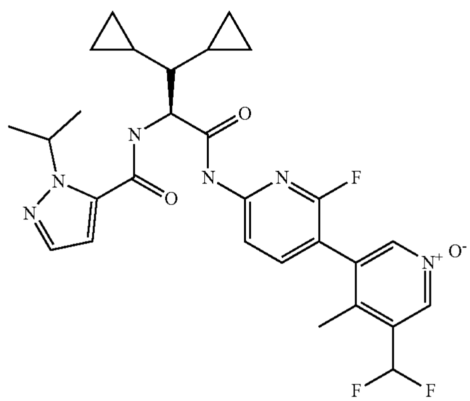 | 55 | (ES): m/z 557.249 [M + H]+, RT = 2.36 min |
| 49 | N-[(1S)-1-(dicyclopropyl-methyl)-2-[[5-[5-(difluoromethyl)-2-methyl-1-oxido-pyridin-1-ium-3-yl]-6-fluoro-2-pyridyl]amino]-2-oxo-ethyl]-2-isopropyl-pyrazole-3-carboxamide | 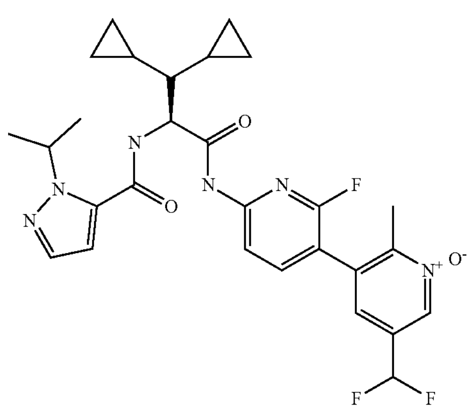 | 56 | (ES): m/z 557.248 [M + H]+, RT = 2.36 min |

| Example number | Name | Structure | Precursor Prep. No. | LCMS details |
|---|---|---|---|---|
| 50 | N-[(1S)-1-(dicyclopropyl-methyl)-2-[6-fluoro-5-[5-fluoro-1-oxido-4-(trifluoromethyl)pyridin-1-ium-3-yl]-2-pyridyl]amino]-2-oxo-ethyl]-2-isopropyl-pyrazole-3-carboxamide | 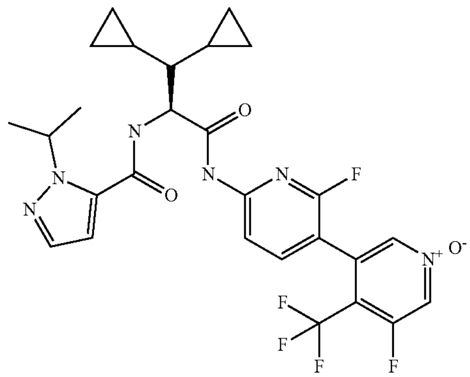 | 57 | (ES): m/z 579.215 [M + H]+, RT = 2.49 min |
| 51 | N-[(1S)-1-(dicyclopropyl-methyl)-2-[[5-[4-(difluoromethyl)-1-oxido-pyridin-1-ium-3-yl]-6-fluoro-2-pyridyl]amino]-2-oxo-ethyl]-2-isopropyl-pyrazole-3-carboxamide | 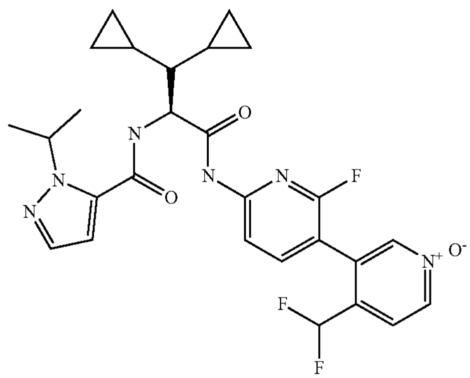 | 58 | (ES): m/z 543.233 [M + H]+, RT = 2.31 min |
| 52 | N-[(1S)-1-(dicyclopropylmethyl)-2-[[5-(4,5-dimethyl-1-oxido-pyridin-1-ium-3-yl)-6-fluoro-2-pyridyl]amino]-2-oxo-ethyl]-2-isopropyl-pyrazole-3-carboxamide | 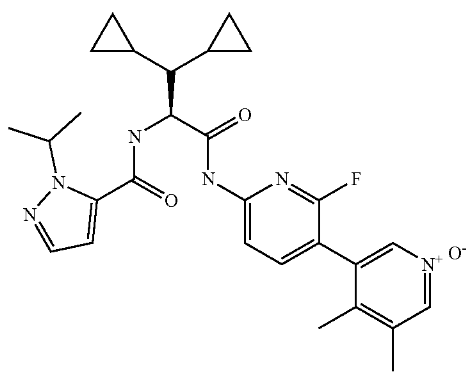 | 59 | (ES): m/z 521.267 [M + H]+, RT = 2.27 min |
| 53 | N-[(1S)-1-(dicyclopropyl-methyl)-2-[5-(4-ethyl-1-oxido-pyridin-1-ium-3-yl)-6-fluoro-2-pyridyl]amino]-2-oxo-ethyl]-2-isopropyl-pyrazole-3-carboxamide | 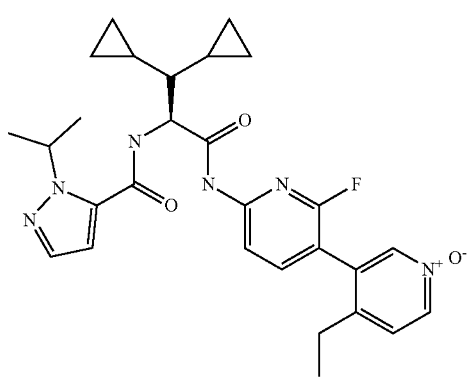 | 60 | (ES): m/z 521.268 [M + H]+, RT = 2.29 min |

| Example Number | Name | Structure | ¹H NMR (400 MHz, DMSO-d₆) |
|---|---|---|---|
| 43 | N-[(1S)-1-(dicyclopropyl-methyl)-2-[[5-(2,5-dimethyl-1-oxido-pyridin-1-ium-3-yl)-6-fluoro-2-pyridyl]amino]-2-oxo-ethyl]-2-(2,2,2-trifluoroethyl)pyrazole-3-carboxamide | 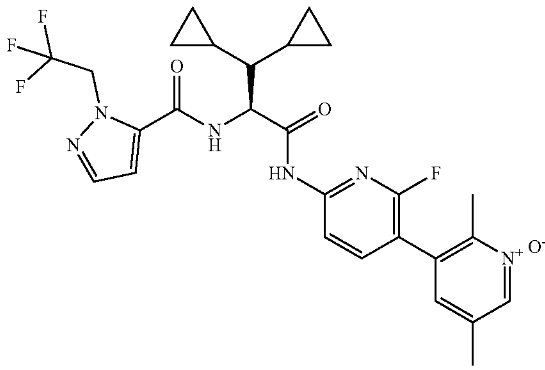 | δ 11.10 (s, 1H), 8.73 (d, J = 8.6 Hz, 1H), 8.28 (s, 1H), 8.11 (dd, J = 8.2, 1.8 Hz, 1H), 8.01 (dd, J = 10.0, 8.2 Hz, 1H), 7.70 (d, J = 2.0 Hz, 1H), 7.21 (d, J = 2.1 Hz, 1H), 7.17 (s, 1H), 5.62-5.40 (m, 2H), 4.96 (t, J = 8.0 Hz, 1H), 2.26 (s, 3H), 2.18 (s, 3H), 1.05-0.91 (m, 1H), 0.91-0.69 (m, 2H), 0.53-0.43 (m, 1H), 0.43-0.34 (m, 1H), 0.34-0.07 (m, 6H) |
| 44 | N-[(1S)-1-(dicyclopropyl-methyl)-2-[[5-(2,5-dimethyl-1-oxido-pyridin-1-ium-3-yl)-6-fluoro-2-pyridyl]amino]-2-oxo-ethyl]-2-sec-butyl-pyrazole-3-carboxamide | 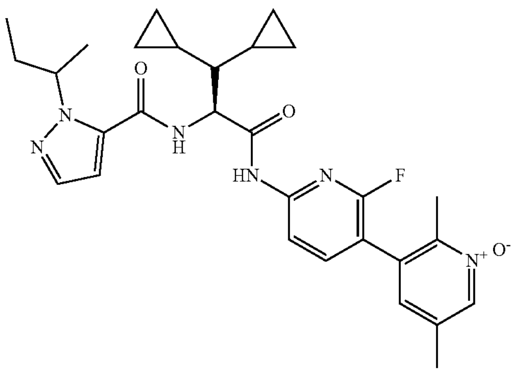 | δ 11.06 and 11.04 (2 × s, 1H), 8.50 and 8.45 (2 × d, J = 8.5 Hz, 1H), 8.28 (s, 1H), 8.14-8.08 (m, 1H), 8.01 (dd, J = 10.0, 8.2 Hz, 1H), 7.53 (d, J = 2.0 Hz, 1H), 7.17 (s, 1H), 6.92 and 6.88 (2 × d, J = 2.0 Hz, 1H), 5.29-5.11 (m, 1H), 4.95-4.84 (m, 1H), 2.26 (s, 3H), 2.18 (s, 3H), 1.90-1.59 (m, 2H), 1.38 and 1.34 (2 × d, J = 6.6 Hz, 3H), 1.03-0.93 (m, 1H), 0.92-0.82 (m, 1H), 0.82-0.71 (m, 1H), 0.67 and 0.60 (2 × t, J = 7.4 Hz, 3H), 0.54 - 0.44 (m, 1H), 0.43-0.34 (m, 1H), 0.34-0.10 (m, 6H) |
| 45 | N-[(1S)-1-(dicyclopropyl-methyl)-2-[[5-(2,5-dimethyl-1-oxido-pyridin-1-ium-3-yl)-6-fluoro-2-pyridyl]amino]-2-oxo-ethyl]-2-(2,2-difluoropropyl)pyrazole-3-carboxamide | 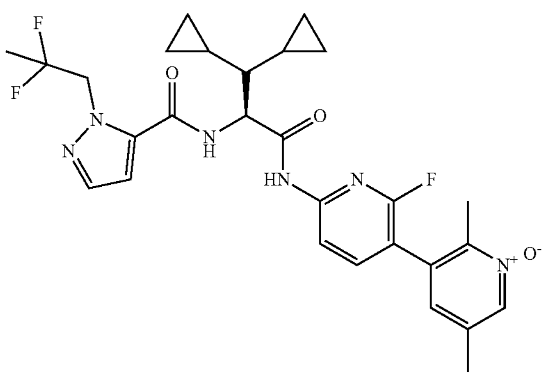 | δ 11.06 (s, 1H), 8.63 (d, J = 8.6 Hz, 1H), 8.28 (s, 1H), 8.11 (dd, J = 8.2, 1.8 Hz, 1H), 8.01 (dd, J = 10.0, 8.2 Hz, 1H), 7.62 (d, J = 2.0 Hz, 1H), 7.17 (s, 1H), 7.09 (d, J = 2.0 Hz, 1H), 5.18-4.97 (m, 2H), 4.94 (t, J = 8.0 Hz, 1H), 2.26 (s, 3H), 2.18 (s, 3H), 1.53 (t, J = 19.1 Hz, 3H), 1.05-0.91 (m, 1H), 0.91-0.67 (m, 2H), 0.57-0.44 (m, 1H), 0.44-0.09 (m, 7H) |
| 46 | N-[(1S)-1-(dicyclopropyl-methy-)-2-[[5-(2,5-dimethyl-1-oxido-pyridin-1-ium-3-yl)-6-fluoro-2-pyridyl]amino]-2-oxo-ethyl]-2-[(1S)-2-hydroxy-1-methyl-ethyl]pyrazole-3-carboxamide | 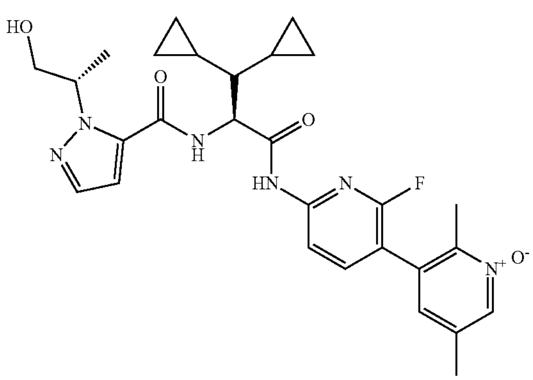 | δ 11.07 (s, 1H), 8.48 (d, J = 8.4 Hz, 1H), 8.28 (s, 1H), 8.11 (dd, J = 8.1, 1.7 Hz, 1H), 8.01 (dd, J = 10.0, 8.2 Hz, 1H), 7.52 (d, J = 2.0 Hz, 1H), 7.17 (s, 1H), 6.92 (d, J = 2.0 Hz, 1H), 5.28 (h, J = 6.7 Hz, 1H), 4.95-4.85 (m, 2H), 3.77-3.66 (m, 1H), 3.66-3.53 (m, 1H), 2.27 (s, 3H), 2.19 (s, 3H), 1.32 (d, J = 6.7 Hz, 3H), 1.03-0.93 (m, 1H), 0.92-0.82 (m, 1H), 0.82-0.72 (m, 1H), 0.56-0.45 (m, 1H), 0.44-0.29 (m, 2H), 0.29-0.14 (m, 5H) |

Example 54: Atropisomer 1 of N-[(1S)-1-(dicyclopropylmethyl)-2-[[6-fluoro-5-[2-methyl-1-oxido-4-(trifluoromethyl)pyridin-1-ium-3-yl]-2-pyridyl]amino]-2-oxo-ethyl]-2-isopropyl-pyrazole-3-carboxamide and Example 55: Atropisomer 2 of N-[(1S)-1-(dicyclopropylmethyl)-2-[[6-fluoro-5-[2-methyl-1-oxido-4-(trifluoromethyl)pyridin-1-ium-3-yl]-2-pyridyl]amino]-2-oxo-ethyl]-2-isopropyl-pyrazole-3-carboxamide

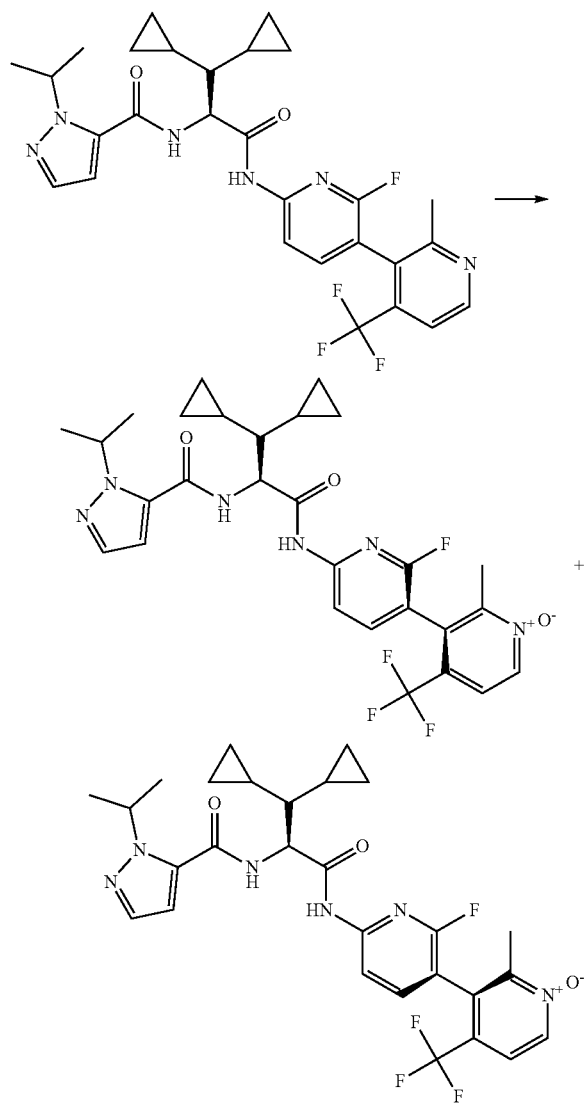

According to the method of Example 1 the compound of Preparation 65 (28 mg, 0.050 mmol) was reacted with mCPBA to give a mixture of atropisomers. The individual atropisomers were isolated as colorless solids after separation by prep. basic HPLC.

Example 54: Peak 1 (8.8 mg, 31% Yield). LCMS (ES): m/z 575.240 [M+H]+, RT=2.42 min; $^1$H NMR (600 MHZ, DMSO-$d_6$) δ 11.15 (s, 1H), 8.57 (d, J=6.9 Hz, 1H), 8.49 (d, J=8.3 Hz, 1H), 8.14 (dd, J=8.1, 1.6 Hz, 1H), 8.00 (t, J=9.0 Hz, 1H), 7.79 (d, J=7.0 Hz, 1H), 7.51 (d, J=1.9 Hz, 1H), 6.92 (d, J=1.9 Hz, 1H), 5.39 (hept, J=6.6 Hz, 1H), 4.90 (t, J=7.9 Hz, 1H), 2.12 (s, 3H), 1.38 (d, J=6.5 Hz, 3H), 1.35 (d, J=6.6 Hz, 3H), 1.04-0.94 (m, 1H), 0.92-0.83 (m, 1H), 0.82-0.70 (m, 1H), 0.56-0.44 (m, 1H), 0.45-0.37 (m, 1H), 0.37-0.27 (m, 2H), 0.27-0.19 (m, 3H), 0.20-0.11 (m, 1H).

Example 55: Peak 2 (7.9 mg, 27% Yield). LCMS (ES): m/z 575.240 [M+H]+, RT=2.44 min; $^1$H NMR (600 MHz, DMSO-$d_6$) δ 11.13 (s, 1H), 8.57 (d, J=6.9 Hz, 1H), 8.49 (d, J=8.4 Hz, 1H), 8.14 (dd, J=8.2, 1.7 Hz, 1H), 8.00 (dd, J=9.9, 8.2 Hz, 1H), 7.79 (d, J=7.0 Hz, 1H), 7.51 (d, J=1.9 Hz, 1H), 6.92 (d, J=2.0 Hz, 1H), 5.38 (hept, J=6.6 Hz, 1H), 4.90 (t, J=7.9 Hz, 1H), 2.14 (s, 3H), 1.38 (d, J=6.5 Hz, 3H), 1.34 (d, J=6.6 Hz, 3H), 1.03-0.95 (m, 1H), 0.92-0.83 (m, 1H), 0.81-0.73 (m, 1H), 0.53-0.45 (m, 1H), 0.43-0.36 (m, 1H), 0.35-0.20 (m, 4H), 0.20-0.11 (m, 2H).

Example 56: Atropisomer 1 of N-[(1S)-1-[[6-chloro-5-(2,4-dimethyl-1-oxido-pyridin-1-ium-3-yl)-2-pyridyl]carbamoyl]-2,2-dicyclopropyl-ethyl]-2-isopropyl-pyrazole-3-carboxamide and Example 57: Atropisomer 2 of N-[(1S)-1-[[6-chloro-5-(2,4-dimethyl-1-oxido-pyridin-1-ium-3-yl)-2-pyridyl]carbamoyl]-2,2-dicyclopropyl-ethyl]-2-isopropyl-pyrazole-3-carboxamide

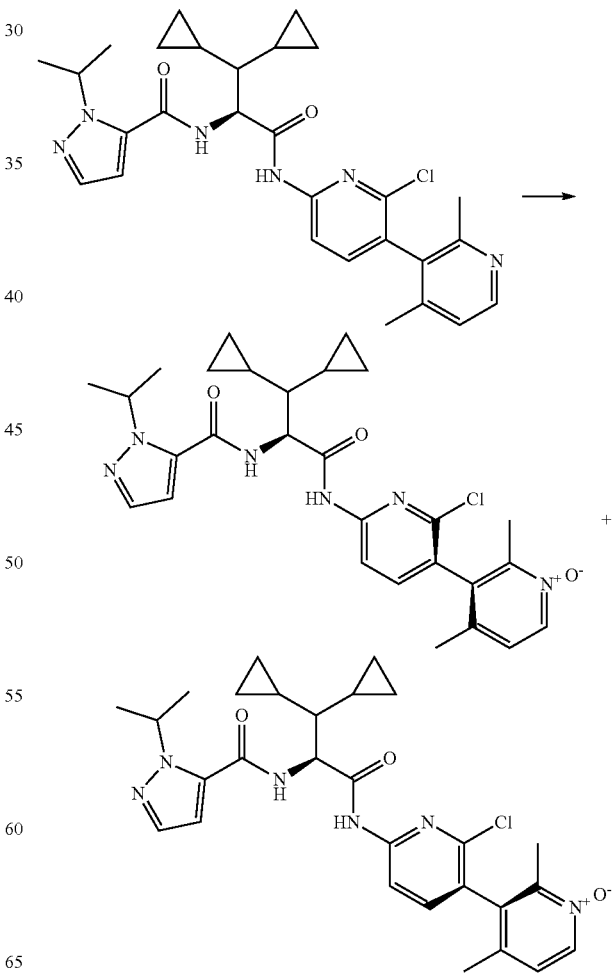

According to the method of Example 1 the compound of Preparation 69 (450 mg, 0.864 mmol) was reacted with mCPBA to give a mixture of atropisomers. The individual atropisomers were isolated as colorless solids after separation by acidic prep. HPLC.

Example 56: Peak 1 (80 mg, 17% Yield). LCMS (METHOD 2) (ESI): m/z 537.4 [M+H]$^+$, RT=1.88 min. (Acquity BEH C18 (50 mm×2.1 mm), 0.05% formic acid in MeCN, 0.05% formic acid in H$_2$O); $^1$H NMR (400 MHZ, DMSO-d$_6$) δ 11.22 (s, 1H), 8.49 (d, J=8.38 Hz, 1H), 8.27 (d, J=6.63 Hz, 1H), 8.21 (d, J=8.38 Hz, 1H), 7.85 (d, J=8.38 Hz, 1H), 7.51 (d, J=1.75 Hz, 1H), 7.30 (d, J=6.63 Hz, 1H), 6.92 (d, J=2.00 Hz, 1H), 5.31-5.47 (m, 1H), 4.90 (t, J=7.82 Hz, 1H), 2.07 (s, 3H), 1.97 (s, 3H), 1.38 (d, J=6.57 Hz, 3H), 1.34 (d, J=6.57 Hz, 3H), 0.94-1.05 (m, 1H), 0.83-0.92 (m, 1H), 0.72-0.82 (m, 1H), 0.45-0.56 (m, 1H), 0.36-0.44 (m, 1H), 0.14-0.34 (m, 6H).

Example 57: Peak 2 (80 mg, 17% Yield). LCMS (METHOD 2) (ESI): m/z 537.4 [M+H]$^+$, RT=1.89 min. (Acquity BEH C18 (50 mm×2.1 mm), 0.05% formic acid in MeCN, 0.05% formic acid in H$_2$O); $^1$H NMR (400 MHZ, DMSO-d$_6$) δ 11.21 (s, 1H), 8.49 (d, J=8.38 Hz, 1H), 8.28 (d, J=6.63 Hz, 1H), 8.21 (d, J=8.25 Hz, 1H), 7.86 (d, J=8.25 Hz, 1H), 7.52 (d, J=1.88 Hz, 1H), 7.30 (d, J=6.63 Hz, 1H), 6.92 (d, J=2.00 Hz, 1H), 5.35-5.43 (m, 1H), 4.91 (t, J=7.88 Hz, 1H), 2.08 (s, 3H), 1.96 (s, 3H), 1.39 (d, J=6.57 Hz, 3H), 1.35 (d, J=6.57 Hz, 3H), 0.94-1.04 (m, 1H), 0.83-0.91 (m, 1H), 0.72-0.81 (m, 1H), 0.47-0.54 (m, 1H), 0.31-0.47 (m, 2H), 0.14-0.31 (m, 5H).

Example 58: N-[(1S)-1-(dicyclopropylmethyl)-2-[[6-fluoro-5-(2-methyl-5-methylsulfonyl-1-oxido-pyridin-1-ium-3-yl)-2-pyridyl]amino]-2-oxo-ethyl]-2-isopropyl-pyrazole-3-carboxamide

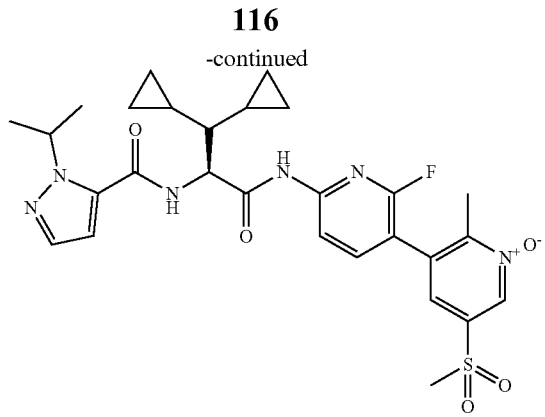

According to the method of Preparation 28, the compounds of Preparation 70 (0.206 mmol) were reacted with 3-bromo-2-methyl-5-methylsulfonyl-1-oxido-pyridin-1-ium (formed by mCPBA oxidation of 3-bromo-2-methyl-5-methylsulfanyl-pyridine) (74 mg, 0.28 mmol) to give the title compound (11.9 mg, 10% Yield) as a pale brown solid after purification by acidic prep. HPLC. LCMS (METHOD 2) (ESI): m/z 585.4 [M+H]$^+$, RT=1.86 min. (Acquity BEH C18 (50 mm×2.1 mm), 0.05% formic acid in MeCN, 0.05% formic acid in H$_2$O); $^1$H NMR (400 MHZ, DMSO-d$_6$) δ 11.18 (s, 1H), 8.80 (d, J=1.25 Hz, 1H), 8.54 (br d, J=8.51 Hz, 1H), 8.06-8.18 (m, 2H), 7.79 (d, J=1.38 Hz, 1H), 7.52 (d, J=1.88 Hz, 1H), 6.93 (d, J=2.00 Hz, 1H), 5.39 (hept, J=6.61 Hz, 1H), 4.90 (t, J=7.94 Hz, 1H), 3.42 (s, 3H), 2.31 (s, 3H), 1.34-1.41 (m, 6H), 0.96-1.03 (m, 1H), 0.85-0.93 (m, 1H), 0.75-0.81 (m, 1H), 0.44-0.53 (m, 1H), 0.36-0.43 (m, 1H), 0.12-0.34 (m, 6H).

Example 59: N-[(1S)-1-[[5-(5-cyano-2-methyl-1-oxido-pyridin-1-ium-3-yl)-6-fluoro-2-pyridyl]carbamoyl]-2,2-dicyclopropyl-ethyl]-2-isopropyl-pyrazole-3-carboxamide

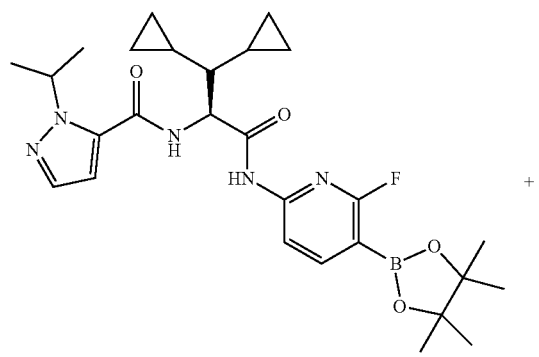

+

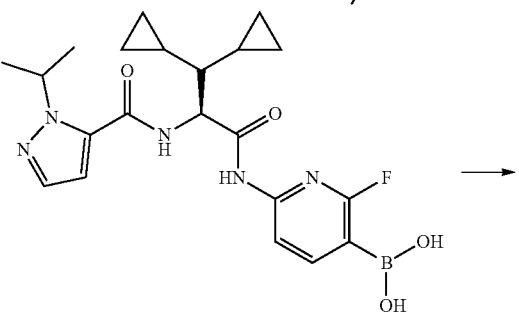

+

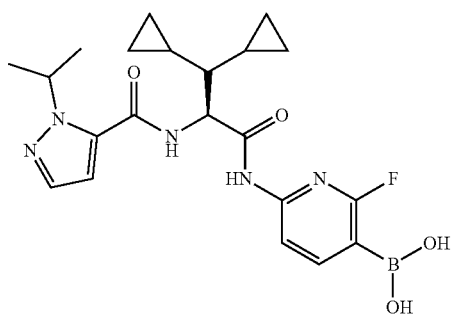

→

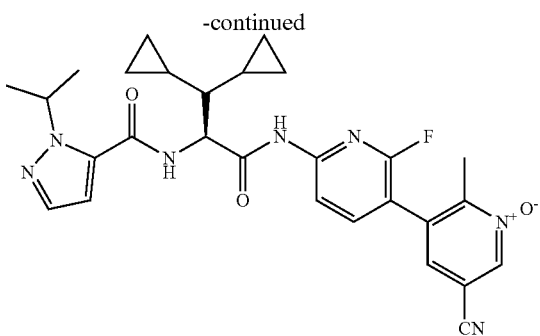

According to the method of Preparation 28, the compounds of Preparation 70 (0.206 mmol) were reacted with the compound of Preparation 70 (42 mg, 0.25 mmol) to give the title compound (9.8 mg, 9% Yield) as a pale brown solid after purification by acidic prep. HPLC. LCMS (METHOD 2) (ESI): m/z 530.4 [M+H]$^+$, RT=1.93 min. (Acquity BEH C18 (50 mm×2.1 mm), 0.05% formic acid in MeCN, 0.05% formic acid in H$_2$O); $^1$H NMR (400 MHZ, DMSO-d$_6$) δ 11.20 (br s, 1H), 9.03 (s, 1H), 8.56 (br d, J=8.51 Hz, 1H), 8.11-8.16 (m, 1H), 8.03-8.09 (m, 1H), 7.89 (s, 1H), 7.51 (d, J=1.75 Hz, 1H), 6.93 (d, J=1.88 Hz, 1H), 5.33-5.44 (m, 1H), 4.90 (t, J=7.82 Hz, 1H), 2.28 (s, 3H), 1.38 (d, J=6.63 Hz, 3H), 1.34 (d, J=6.63 Hz, 3H), 0.93-1.02 (m, 1H), 0.82-0.92 (m, 1H), 0.73-0.81 (m, 1H), 0.45-0.53 (m, 1H), 0.34-0.42 (m, 1H), 0.26-0.34 (m, 2H), 0.13-0.25 (m, 4H).

Example 60: N-[(1S)-1-(dicyclopropylmethyl)-2-[[6-fluoro-5-(5-methoxy-2-ethyl-1-oxido-pyridin-1-ium-3-yl)-2-pyridyl]amino]-2-oxo-ethyl]-2-isopropyl-pyrazole-3-carboxamide

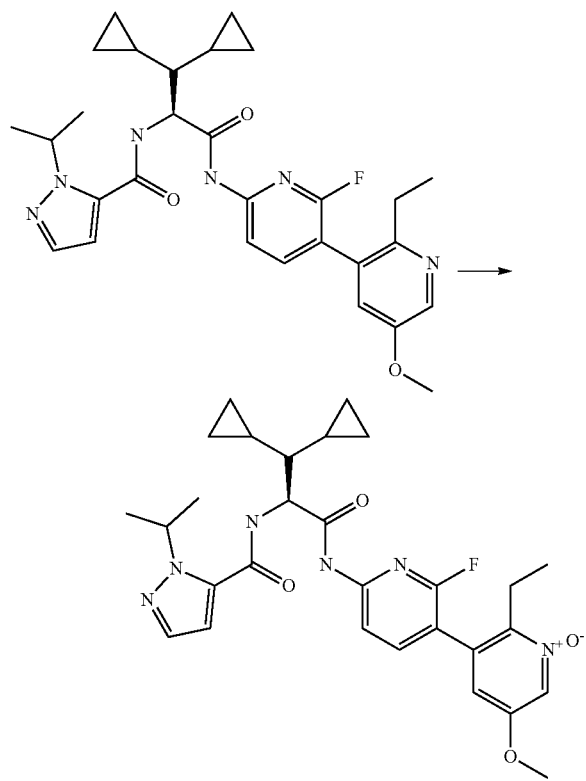

According to the Method of Example 1, the pyridine of Preparation 61 was oxidized to give the title compound (25 mg, 16%) as an off-white solid after purification by acidic prep. HPLC. LCMS (METHOD 2) (ESI): m/z 551.38 [M+H]$^+$, RT=1.92 min. (Acquity BEH C18 (50 mm×2.1 mm), 0.05% formic acid in MeCN, 0.05% formic acid in H$_2$O); $^1$H NMR (400 MHz, DMSO-d$_6$) δ 11.08 (s, 1H), 8.49 (br d, J=8.50 Hz, 1H), 8.19 (d, J=2.25 Hz, 1H), 8.08-8.12 (m, 1H), 7.95-8.03 (m, 1H), 7.51 (d, J=1.63 Hz, 1H), 7.04 (d, J=2.13 Hz, 1H), 6.92 (d, J=1.8 Hz, 1H), 5.38 (hept, J=6.6 Hz, 1H), 4.90 (t, J=7.82 Hz, 1H), 3.82 (s, 3H), 2.56-2.64 (m, 2H), 1.36 (dd, J=15.57, 6.57 Hz, 6H), 1.03-0.99 (m, 3H), 0.98-0.92 (m, 1H), 0.90-0.84 (m, 1H), 0.80-0.73 (m, 1H), 0.52-0.45 (m, 1H), 0.42-0.35 (m, 1H), 0.34-0.14 (m, 6H).

Example 61: Inhibition of Human IL-17-Induced SEAP Reporter Gene Activity in HEK-Blue™ IL-17 Cells 50 nL test compounds in 100% DMSO were added into each well reserved for test compounds in a 384-well ViewPlates (Perkin Elmer), by the use of acoustic pipetting. The remaining wells received an equal volume of DMSO, as vehicle control, or VETRANAL® (Merck) in DMSO, as a positive control for cytotoxicity. Subsequently, 5 μl of an anti-IL-17A monoclonal antibody (final concentration 150 ng/ml) was added to the positive control wells. All wells containing test compounds and wells prepared to yield maximum stimulation received 5 μL of human TH-17 supernatant corresponding to 2 ng/ml IL-17A final concentration (measured by IL-17A AlphaLisa® SureFire®, Perkin Elmer). Finally, 45 μl HEK-Blue™ IL-17 cells (Invivogen) were added to all the wells resulting in a density of 12500 cells/well and incubated in a humid incubator at 37° C., 5% CO$_2$, overnight. The HEK-Blue™ IL-17 cells, anti-IL-17A antibody and TH-17 supernatant were all diluted in DMEM with high glucose (Sigma) supplemented with 10% FBS, 1% P/S (Life technologies) and HEK-Blue™ selection (Invivogen).

After incubation, 5 μl of the supernatant was transferred from the cell plate to a new Viewplate and 45 μl Quanti-Blue™ solution, a SEAP detection reagent, was added, and the Quanti-Blue™/cell supernatant was incubated at 37° C. The plate was inspected for color development (5 to 60 minutes) and read using Envision, Perkin Elmer, plate reader (absorbance at 620 nm). The SEAP levels were calculated as percent of controls. Reduction of the amount of SEAP indicates decreased IL-17 signalling. Concentration response curves were fitted using a four-parameter logistic equation. Relative IC$_{50}$ and Emax were reported from curves showing acceptable fit (r2>0.9). Cytotoxicity was measured in the cell-containing Viewplate following addition of 7 μL PrestoBlue (Thermo Fisher) and incubation for 2.5-3 hours at room temperature, by measuring fluorescence at 615 nm (excitation at 535 nm). Fluorescence was directly proportional to the amount of metabolic activity. Reduction of fluorescence signal indicated cytotoxicity.

Compounds of the present invention were tested in the assay of Example 61. The results are summarized in Table 1.

TABLE 1

| Example No. | HEK Blue™ assay EC$_{50}$ (nM) |
|---|---|
| 1 | 11 |
| 2 | 19 |
| 3 | 10 |
| 4 | 14 |
| 5 | 34 |
| 6 | 12 |
| 7 | 2700 |
| 8 | 42 |
| 9 | 22 |
| 10 | 60 |
| 11 | 14 |
| 12 | 13 |
| 13 | 33 |
| 14a | 28 |
| 14b | 1488 |
| 15 | 73 |
| 16 | 35 |
| 18 | 12 |
| 19 | 28 |
| 20 | 11 |
| 21 | 510 |
| 22 | 9.1 |
| 23 | 20 |
| 25 | 18 |
| 26 | 84 |
| 27 | 25 |
| 28 | 28 |
| 29 | 11 |
| 30 | 33 |
| 31 | 23 |
| 32 | 19 |
| 35 | 14 |
| 36 | 9.4 |
| 37 | 16 |
| 38 | 27 |
| 39 | 18 |
| 40 | 52 |
| 41 | 19 |
| 42 | 33 |
| 43 | 32 |
| 44 | 14 |
| 45 | 34 |
| 46 | 80 |
| 47 | 39 |
| 48 | 10 |
| 49 | 12 |
| 50 | 30 |
| 51 | 54 |
| 52 | 44 |
| 53 | 56 |
| 54 | 3.6 |
| 55 | 22 |

Example 62: Inhibition of Recombinant IL-17AA-Induced SEAP Reporter Gene Activity in HEK-Blue™ IL-17 Cells The assay was run according to the protocol provided by InvivoGen. Briefly, the HEK-Blue™ IL-17 cells (Invivogen, cat #hkb-il17) were suspended in the complete culture medium and seeded in a 96 well plate in a volume of 80 µl in a density of 50,000 cells per well the day before the assay. 10 µl of a solution of the test compounds were added in a serial gradient dilution to the cells followed by the addition of 10 µl IL-17A (R&D Systems cat #7955-IL) in a final concentration of 2 ng/ml. The plate was incubated overnight. The QUANTI-Blue™ solution was used to determine the SEAP activity; 180 µl QUANTI-Blue™ solution and 20 µl of the supernatant from the cell plate were mixed and incubated for 1 hour at 37 degrees Celsius. SEAP levels were measured using a spectrophotometer at 650 nm.

Compounds of the present invention were tested in the assay of Example 62. The results are summarized in Table 2.

TABLE 2

| Example No. | HEK Blue™ assay EC$_{50}$ (nM) |
|---|---|
| 1 | 11 |
| 3 | 17 |
| 56 | 4.6 |
| 57 | 740 |
| 58 | 100 |
| 59 | 46 |
| 60 | 31 |

Example 63: Human Liver Microsome (HLM) Clearance Assay

Metabolic stability in human liver microsomes was measured as compound clearance following 40 min incubation with human liver microsomes (0.5 mg/mL) and NADPH (1 mM) at a test compound concentration of 0.5 µM. Samples were taken out before addition of NADPH, and at 5, 10, 20 and 40 minutes thereafter and protein precipitation using cold acetonitrile with added internal standard was performed prior to centrifugation and sample analysis using compound specific LCMS/MS methods. Control incubations in buffer and without NADPH were performed in the same manner. Compound depletion was determined and apparent clearance (CL$_{app}$) was calculated.

Compounds of the present invention were tested in the assay of Example 63. The results are summarized in Table 3.

TABLE 3

| Example No. | HLM Cl$_{app}$ (mL/min/kg) |
|---|---|
| 1 | 12 |
| 2 | <8 |
| 3 | <8 |
| 4 | 9 |
| 5 | <8 |
| 6 | 14 |
| 7 | <8 |
| 8 | 8 |
| 9 | <8 |
| 10 | 22 |
| 11 | <8 |
| 12 | <8 |
| 13 | 14 |
| 14 | 12 |
| 15 | <8 |
| 16 | <8 |
| 18 | <8 |
| 19 | <8 |
| 20 | 74 |
| 22 | 73 |
| 23 | <8 |
| 24 | <8 |
| 25 | 250 |
| 26 | <8 |
| 27 | <8 |
| 28 | >750 |
| 29 | 8 |
| 32 | 23 |
| 47 | <8 |
| 48 | <8 |
| 49 | <8 |

TABLE 3-continued

| Example No. | HLM Cl$_{app}$ (mL/min/kg) |
| --- | --- |
| 50 | 10 |
| 51 | <8 |
| 52 | <8 |
| 53 | <8 |
| 54 | 63 |
| 55 | 41 |
| 56 | 16 |
| 57 | 18 |
| 58 | 10 |
| 59 | <9 |

Example 64: Solubility Assay

The solubility was determined by shaking the test compound (10 μL of a 10 mM DMSO stock solution) in 990 μL 0.067 M phosphate buffer at pH 6.5 for 24 hours. After centrifugation, the supernatant was analyzed by HPLC-UV. The solubility was defined as the concentration of the test substance in the selected solvent. It was determined by correlation with an external standard calibration curve.

Compounds of the present invention were tested in the assay of Example 64. The results are summarized in Table 4.

TABLE 4

| Example No. | Solubility at pH 6.5 (μg/mL) |
| --- | --- |
| 1 | 29 |
| 2 | 26 |
| 3 | 45 |
| 4 | 74 |
| 5 | 35 |
| 6 | 5 |
| 7 | 38 |
| 8 | 8 |
| 9 | 23 |
| 10 | 9 |
| 11 | 6.5 |
| 12 | 6 |
| 13 | 26 |
| 14 | <1 |
| 15 | 97 |
| 16 | 60 |
| 18 | 26 |
| 19 | 18 |
| 20 | 38 |
| 22 | 28 |
| 48 | 19 |
| 49 | 18 |
| 50 | <1 |
| 51 | 25 |
| 52 | 4 |
| 53 | 39 |
| 54 | <1 |
| 55 | <1 |
| 56 | <1 |
| 57 | <1 |
| 58 | 14 |
| 59 | 29 |

EMBODIMENTS

Embodiment 1. A compound having the formula (I)

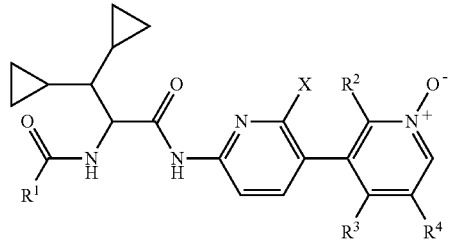

(I)

wherein X is fluoro or chloro;
R$^1$ is selected from

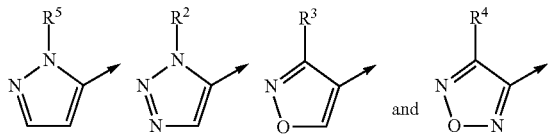

wherein R$^5$ is independently selected from (C$_1$-C$_4$)alkyl, (C$_3$-C$_4$)cycloalkyl, and —CH$_2$—(C$_3$-C$_4$)cycloalkyl, wherein said (C$_1$-C$_4$)alkyl, (C$_3$-C$_4$)cycloalkyl, and —CH$_2$—(C$_3$-C$_4$)cycloalkyl may optionally be substituted with substituents independently selected from one hydroxy group and 1, 2 or 3 fluoro;
R$^2$ is selected from hydrogen, (C$_1$-C$_3$)alkyl, cyclopropyl, and chloro, wherein said (C$_1$-C$_3$)alkyl may optionally be substituted with one or more fluoro;
R$^3$ is selected from hydrogen, (C$_1$-C$_3$)alkyl, cyclopropyl, and chloro, wherein said (C$_1$-C$_3$)alkyl may optionally be substituted with one or more fluoro; and
R$^4$ is selected from hydrogen, (C$_1$-C$_3$)alkyl, cyclopropyl, (C$_1$-C$_2$)alkoxy, cyano, methylsulfone, fluoro, and chloro; wherein said (C$_1$-C$_3$)alkyl and (C$_1$-C$_2$)alkoxy may optionally be substituted with one or more fluoro;
provided that at least one of R$^2$ and R$^3$ is different from hydrogen;
or pharmaceutically acceptable salts thereof.

Embodiment 2. The compound according to embodiment 1 having the formula (II)

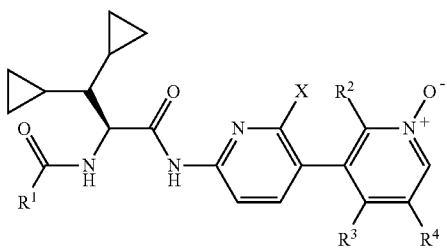

(II)

wherein X, R$^1$, R$^2$, R$^3$, R$^4$, and R$^5$ are as defined in embodiment 1; or pharmaceutically acceptable salts thereof.

Embodiment 3. The compound according to embodiment 1 having the formula (III)

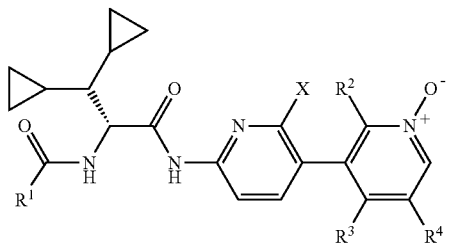

(III)

wherein X, R¹, R², R³, R⁴, and R⁵ are as defined in embodiment 1; or pharmaceutically acceptable salts thereof.

Embodiment 4. The compound according to any one of embodiments 1-3 wherein R¹ is

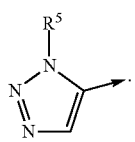

Embodiment 5. The compound according to embodiment 4 wherein R⁵ is independently selected from $(C_1-C_4)$alkyl, $(C_3-C_4)$cycloalkyl, and —CH$_2$—$(C_3-C_4)$cycloalkyl, wherein said $(C_1-C_4)$alkyl, $(C_3-C_4)$cycloalkyl, and —CH$_2$—$(C_3-C_4)$cycloalkyl may optionally be substituted with substituents independently selected from 1, 2 or 3 fluoro.

Embodiment 6. The compound according to embodiment 5 wherein R⁵ is $(C_1-C_4)$alkyl, wherein said $(C_1-C_4)$alkyl, may optionally be substituted with substituents independently selected from 1, 2 or 3 fluoro.

Embodiment 7. The compound according to embodiment 6 wherein R⁵ is $(C_1-C_4)$alkyl.

Embodiment 8. The compound according to embodiment 7 wherein R⁵ is propan-2-yl.

Embodiment 9. The compound according to any one of embodiments 4 to 8 wherein

R² is selected from hydrogen and methyl.

Embodiment 10. The compound according to any one of embodiments 4 to 8 wherein

R² is selected from hydrogen and methyl;

R³ is selected from hydrogen, methyl, and trifluoromethyl; and

R⁴ is selected from hydrogen, methyl, cyclopropyl, $(C_1-C_2)$alkoxy, fluoro, and chloro; wherein said methyl and $(C_1-C_2)$alkoxy may optionally be substituted with one or more fluoro.

Embodiment 11. The compound according to any one of embodiments 9 or 10 wherein R² is methyl.

Embodiment 12. The compound according to any one of embodiments 1-3 wherein R¹ is

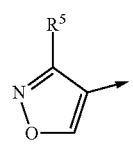

Embodiment 13. The compound according to embodiment 12 wherein R⁵ is independently selected from $(C_1-C_4)$alkyl, $(C_3-C_4)$cycloalkyl, and —CH$_2$—$(C_3-C_4)$cycloalkyl, wherein said $(C_1-C_4)$alkyl, $(C_3-C_4)$cycloalkyl, and —CH$_2$—$(C_3-C_4)$cycloalkyl may optionally be substituted with substituents independently selected from 1, 2 or 3 fluoro.

Embodiment 14. The compound according to embodiment 13 wherein R⁵ is $(C_1-C_4)$alkyl, wherein said $(C_1-C_4)$alkyl, may optionally be substituted with substituents independently selected from 1, 2 or 3 fluoro.

Embodiment 15. The compound according to embodiment 14 wherein R⁵ is $(C_1-C_4)$alkyl.

Embodiment 16. The compound according to embodiment 15 wherein R⁵ is propan-2-yl.

Embodiment 17. The compound according to any one of embodiments 12-16 wherein

R² is selected from hydrogen or methyl.

Embodiment 18. The compound according to any one of embodiments 12-16 wherein

R² is selected from hydrogen and methyl;

R³ is selected from hydrogen, methyl, and trifluoromethyl; and

R⁴ is selected from hydrogen, methyl, cyclopropyl, $(C_1-C_2)$alkoxy, fluoro, and chloro; wherein said methyl and $(C_1-C_2)$alkoxy may optionally be substituted with one or more fluoro.

Embodiment 19. The compound according to any one of embodiments 17 or 18 wherein R² is methyl.

Embodiment 20. The compound according to any one of embodiments 1-3 wherein R¹ is

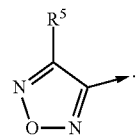

Embodiment 21. The compound according to embodiment 20 wherein R⁵ is independently selected from $(C_1-C_4)$alkyl, $(C_3-C_4)$cycloalkyl, and —CH$_2$—$(C_3-C_4)$cycloalkyl, wherein said $(C_1-C_4)$alkyl, $(C_3-C_4)$cycloalkyl, and —CH$_2$—$(C_3-C_4)$cycloalkyl may optionally be substituted with substituents independently selected from 1, 2 or 3 fluoro.

Embodiment 22. The compound according to embodiment 21 wherein R⁵ is $(C_1-C_4)$alkyl, wherein said $(C_1-C_4)$alkyl, may optionally be substituted with substituents independently selected from 1, 2 or 3 fluoro.

Embodiment 23. The compound according to embodiment 22 wherein R⁵ is $(C_1-C_4)$alkyl.

Embodiment 24. The compound according to embodiment 23 wherein R⁵ is propan-2-yl.

Embodiment 25. The compound according to any one of embodiments 20-24 wherein R² is selected from hydrogen and methyl.

Embodiment 26. The compound according to any one of embodiments 20-24 wherein

R² is selected from hydrogen and methyl;

R³ is selected from hydrogen, methyl, and trifluoromethyl; and

R⁴ is selected from hydrogen, methyl, cyclopropyl, $(C_1-C_2)$alkoxy, fluoro, and chloro; wherein said methyl and $(C_1-C_2)$alkoxy may optionally be substituted with one or more fluoro.

Embodiment 27. The compound according to any one of embodiments 25 or 26 wherein R² is methyl.

Embodiment 28. The compound according to any one of embodiments 1-3 wherein R¹ is

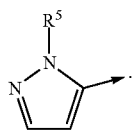

Embodiment 29. The compound according to embodiment 28 wherein $R^5$ is independently selected from $(C_1-C_4)$alkyl, $(C_3-C_4)$cycloalkyl, and —$CH_2$—$(C_3-C_4)$cycloalkyl, wherein said $(C_1-C_4)$alkyl, $(C_3-C_4)$cycloalkyl, and —$CH_2$—$(C_3-C_4)$cycloalkyl may optionally be substituted with substituents independently selected from 1, 2 or 3 fluoro.

Embodiment 30. The compound according to embodiment 29 wherein $R^5$ is $(C_1-C_4)$alkyl, wherein said $(C_1-C_4)$alkyl may optionally be substituted with substituents independently selected from 1, 2 or 3 fluoro.

Embodiment 31. The compound according to embodiment 30 wherein $R^5$ is $(C_1-C_4)$alkyl.

Embodiment 32. The compound according to embodiment 31 wherein $R^5$ is propan-2-yl.

Embodiment 33. The compound according to any one of embodiments 28-32 wherein
$R^2$ is selected from hydrogen and methyl.

Embodiment 34. The compound according to any one of embodiments 28-32 wherein
$R^2$ is selected from hydrogen and methyl;
$R^3$ is selected from hydrogen, methyl, and trifluoromethyl; and
$R^4$ is selected from hydrogen, methyl, cyclopropyl, $(C_1-C_2)$alkoxy, fluoro, and chloro; wherein said methyl and $(C_1-C_2)$alkoxy may optionally be substituted with one or more fluoro.

Embodiment 35. The compound according to any one of embodiments 33 or 34 wherein $R^2$ is methyl.

Embodiment 36. The compound according to any one of the embodiments above wherein the N-oxide moiety

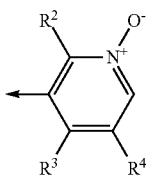
(I)

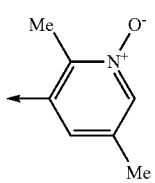 A

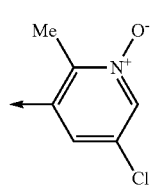 B in the compound of formula (I), (II) or (II) is selected from moiety A, B, C, D, E and F:

-continued

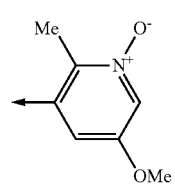 C

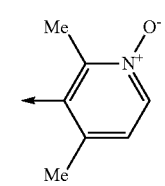 D

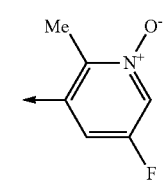 E

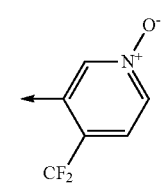 F

Embodiment 37. The embodiment according to any one of embodiments 1-36 wherein X is chloro.

Embodiment 38. The compound according to any one of embodiments 1-36 wherein X is fluoro.

The invention claimed is:

1. A compound according to formula (I)

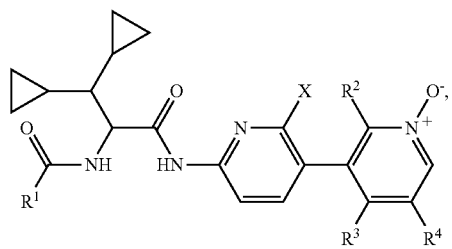
(I)

wherein X is fluoro or chloro;
$R^1$ is selected from

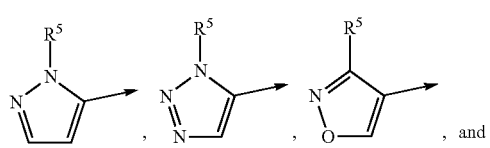, and

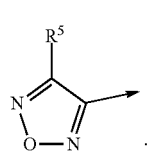

wherein R⁵ is independently selected from (C₁-C₄)alkyl, (C₃-C₄)cycloalkyl, and —CH₂—(C₃-C₄)cycloalkyl, wherein said (C₁-C₄)alkyl, (C₃-C₄)cycloalkyl, and —CH₂—(C₃-C₄)cycloalkyl are optionally substituted with substituents independently selected from one hydroxy group and 1, 2, or 3 fluoro;

R² is selected from hydrogen, (C₁-C₃)alkyl, cyclopropyl, and chloro, wherein said (C₁-C₃)alkyl is optionally substituted with one or more fluoro;

R³ is selected from hydrogen, (C₁-C₃)alkyl, cyclopropyl, and chloro, wherein said (C₁-C₃)alkyl is optionally substituted with one or more fluoro; and R⁴ is selected from hydrogen, (C₁-C₃)alkyl, cyclopropyl, (C₁-C₂)alkoxy, cyano, methylsulfone, fluoro, and chloro; wherein said (C₁-C₃)alkyl and (C₁-C₂)alkoxy are optionally substituted with one or more fluoro;

provided that at least one of R² and R³ is not hydrogen;

or pharmaceutically acceptable salts thereof.

2. The compound according to claim 1, wherein the compound is selected from compounds according to formula (II)

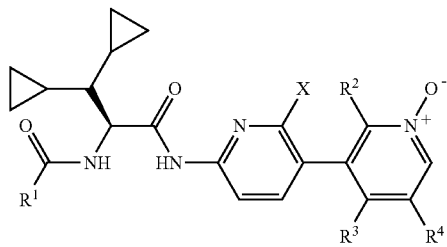

(II)

wherein R¹, R², R³, R⁴, and R⁵ are as defined in claim 1; or pharmaceutically acceptable salts thereof.

3. The compound according to claim 1, wherein R¹ is

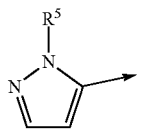

4. The compound according to claim 1, wherein R⁵ is independently selected from (C₁-C₄)alkyl, (C₃-C₄)cycloalkyl, and —CH₂—(C₃-C₄)cycloalkyl, wherein said (C₁-C₄)alkyl, (C₃-C₄)cycloalkyl, and —CH₂—(C₃-C₄)cycloalkyl are optionally substituted with substituents independently selected from 1, 2, or 3 fluoro.

5. The compound according to claim 4, wherein R⁵ is (C₁-C₄)alkyl, wherein said (C₁-C₄)alkyl is optionally substituted with substituents independently selected from 1, 2, or 3 fluoro.

6. The compound according to claim 5, wherein R⁵ is (C₁-C₄)alkyl.

7. The compound according to claim 6, wherein R⁵ is propan-2-yl.

8. The compound according to claim 1, wherein R² is selected from hydrogen and methyl.

9. The compound according to claim 1, wherein
R² is selected from hydrogen and methyl;
R³ is selected from hydrogen, methyl, and trifluoromethyl; and
R⁴ is selected from hydrogen, methyl, cyclopropyl, (C₁-C₂)alkoxy, fluoro, and chloro; wherein said methyl and (C₁-C₂)alkoxy are optionally substituted with one or more fluoro.

10. The compound according to claim 1, wherein R² is methyl.

11. The compound according to claim 1, wherein X is chloro.

12. The compound according to claim 1, wherein X is fluoro.

13. The compound according to claim 1, wherein the compound is selected from:
N-[(1S)-1-(dicyclopropylmethyl)-2-[[6-fluoro-5-(5-methoxy-2-methyl-1-oxido-pyridin-1-ium-3-yl)-2-pyridyl]amino]-2-oxo-ethyl]-2-isopropyl-pyrazole-3-carboxamide;
N-[(1S)-1-(dicyclopropylmethyl)-2-[[6-fluoro-5-(5-fluoro-2-methyl-1-oxido-pyridin-1-ium-3-yl)-2-pyridyl]amino]-2-oxo-ethyl]-2-isopropyl-pyrazole-3-carboxamide;
N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-isopropyl-pyrazole-3-carboxamide;
N-[(1S)-1-(dicyclopropylmethyl)-2-[[5-(2,4-dimethyl-1-oxido-pyridin-1-ium-3-yl)-6-fluoro-2-pyridyl]amino]-2-oxo-ethyl]-2-isopropyl-pyrazole-3-carboxamide;
N-[(1S)-1-(dicyclopropylmethyl)-2-[[5-(2-ethyl-1-oxido-pyridin-1-ium-3-yl)-6-fluoro-2-pyridyl]amino]-2-oxo-ethyl]-2-isopropyl-pyrazole-3-carboxamide;
N-[(1S)-1-(dicyclopropylmethyl)-2-[[6-fluoro-5-[1-oxido-4-(trifluoromethyl)pyridin-1-ium-3-yl]-2-pyridyl]amino]-2-oxo-ethyl]-2-isopropyl-pyrazole-3-carboxamide;
N-[(1S)-2,2-dicyclopropyl-1-[[5-(2-cyclopropyl-1-oxido-pyridin-1-ium-3-yl)-6-fluoro-2-pyridyl]carbamoyl]ethyl]-2-isopropyl-pyrazole-3-carboxamide;
N-[(1S)-1-(dicyclopropylmethyl)-2-[[5-[5-(difluoromethoxy)-2-methyl-1-oxido-pyridin-1-ium-3-yl]-6-fluoro-2-pyridyl]amino]-2-oxo-ethyl]-2-isopropyl-pyrazole-3-carboxamide;
N-[(1S)-1-(dicyclopropylmethyl)-2-[[6-fluoro-5-[5-(fluoromethoxy)-2-methyl-1-oxido-pyridin-1-ium-3-yl]-2-pyridyl]amino]-2-oxo-ethyl]-2-isopropyl-pyrazole-3-carboxamide;
N-[(1S)-1-(dicyclopropylmethyl)-2-[[5-(5-ethoxy-2-methyl-1-oxido-pyridin-1-ium-3-yl)-6-fluoro-2-pyridyl]amino]-2-oxo-ethyl]-2-isopropyl-pyrazole-3-carboxamide;
N-[(1S)-1-[[5-(5-chloro-2-methyl-1-oxido-pyridin-1-ium-3-yl)-6-fluoro-2-pyridyl]carbamoyl]-2,2-dicyclopropyl-ethyl]-2-isopropyl-pyrazole-3-carboxamide;
N-[(1S)-1-(dicyclopropylmethyl)-2-[[6-fluoro-5-[2-methyl-1-oxido-5-(trifluoromethyl)pyridin-1-ium-3-yl]-2-pyridyl]amino]-2-oxo-ethyl]-2-isopropyl-pyrazole-3-carboxamide;
N-[(1S)-2,2-dicyclopropyl-1-[[5-(2-cyclopropyl-5-methyl-1-oxido-pyridin-1-ium-3-yl)-6-fluoro-2-pyridyl]carbamoyl]ethyl]-2-isopropyl-pyrazole-3-carboxamide;
N-[(1S)-2,2-dicyclopropyl-1-[[5-(5-cyclopropyl-2-methyl-1-oxido-pyridin-1-ium-3-yl)-6-fluoro-2-pyridyl]carbamoyl]ethyl]-2-isopropyl-pyrazole-3-carboxamide;
N-[(1S)-1-(dicyclopropylmethyl)-2-[[6-fluoro-5-(4-methyl-1-oxido-pyridin-1-ium-3-yl)-2-pyridyl]amino]-2-oxo-ethyl]-2-isopropyl-pyrazole-3-carboxamide;

N-[(1S)-1-(dicyclopropylmethyl)-2-[[6-fluoro-5-(2-methyl-1-oxido-pyridin-1-ium-3-yl)-2-pyridyl]amino]-2-oxo-ethyl]-2-isopropyl-pyrazole-3-carboxamide;

N-[(1S)-1-[[6-chloro-5-(2,5-dimethyl-1-oxido-pyridin-1-ium-3-yl)-2-pyridyl]carbamoyl]-2,2-dicyclopropyl-ethyl]-2-isopropyl-pyrazole-3-carboxamide;

N-[(1S)-1-[[6-chloro-5-(5-fluoro-2-methyl-1-oxido-pyridin-1-ium-3-yl)-2-pyridyl]carbamoyl]-2,2-dicyclopropyl-ethyl]-2-isopropyl-pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-propyl-pyrazole-3-carboxamide;

2-tert-butyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-isopropyl-isoxazole-4-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-isopropyl-triazole-4-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(2,2-difluoroethyl)pyrazole-3-carboxamide;

2-cyclobutyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(difluoromethyl)pyrazole-3-carboxamide;

2-cyclopropyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-isobutyl-pyrazole-3-carboxamide;

2-(cyclopropylmethyl)-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(3-hydroxybutyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(4,4,4-trifluoro-3-hydroxy-butyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[(3,3-difluorocyclobutyl)methyl]pyrazole-3-carboxamide;

4-cyclopropyl-N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-1,2,5-oxadiazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(3-hydroxypropyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[(1S*)-2,2-difluoro-1-methyl-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[(1S*)-2,2-difluoro-1-methyl-ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[2-fluoro-1-(fluoromethyl)ethyl]pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-methyl-isoxazole-4-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-3-ethyl-isoxazole-4-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-4-methyl-1,2,5-oxadiazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-ethyl-pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-methyl-pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(2,2,2-trifluoroethyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-sec-butyl-pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-(2,2-difluoropropyl)pyrazole-3-carboxamide;

N-[(1S)-1-(dicyclopropylmethyl)-2-[[5-(2,5-dimethyl-1-oxido-pyridin-1-ium-3-yl)-6-fluoro-2-pyridyl]amino]-2-oxo-ethyl]-2-[(1S)-2-hydroxy-1-methyl-ethyl]pyrazole-3-carboxamide N-[(1S)-2,2-dicyclopropyl-1-[[5-(4-cyclopropyl-1-oxido-pyridin-1-ium-3-yl)-6-fluoro-2-pyridyl]carbamoyl]ethyl]-2-isopropyl-pyrazole-3-carboxamide;

N-[(1S)-1-(dicyclopropylmethyl)-2-[[5-[5-(difluoromethyl)-4-methyl-1-oxido-pyridin-1-ium-3-yl]-6-fluoro-2-pyridyl]amino]-2-oxo-ethyl]-2-isopropyl-pyrazole-3-carboxamide;

N-[(1S)-1-(dicyclopropylmethyl)-2-[[5-[5-(difluoromethyl)-2-methyl-1-oxido-pyridin-1-ium-3-yl]-6-fluoro-2-pyridyl]amino]-2-oxo-ethyl]-2-isopropyl-pyrazole-3-carboxamide;

N-[(1S)-1-(dicyclopropylmethyl)-2-[[6-fluoro-5-[5-fluoro-1-oxido-4-(trifluoromethyl)pyridin-1-ium-3-yl]-2-pyridyl]amino]-2-oxo-ethyl]-2-isopropyl-pyrazole-3-carboxamide;

N-[(1S)-1-(dicyclopropylmethyl)-2-[[5-[4-(difluoromethyl)-1-oxido-pyridin-1-ium-3-yl]-6-fluoro-2-pyridyl]amino]-2-oxo-ethyl]-2-isopropyl-pyrazole-3-carboxamide;

N-[(1S)-1-(dicyclopropylmethyl)-2-[[5-(4,5-dimethyl-1-oxido-pyridin-1-ium-3-yl)-6-fluoro-2-pyridyl]amino]-2-oxo-ethyl]-2-isopropyl-pyrazole-3-carboxamide;

N-[(1S)-1-(dicyclopropylmethyl)-2-[[5-(4-ethyl-1-oxido-pyridin-1-ium-3-yl)-6-fluoro-2-pyridyl]amino]-2-oxo-ethyl]-2-isopropyl-pyrazole-3-carboxamide;

Atropisomer 1 of N-[(1S)-1-(dicyclopropylmethyl)-2-[[6-fluoro-5-[2-methyl-1-oxido-4-(trifluoromethyl)pyridin-1-ium-3-yl]-2-pyridyl]amino]-2-oxo-ethyl]-2-isopropyl-pyrazole-3-carboxamide;

Atropisomer 2 of N-[(1S)-1-(dicyclopropylmethyl)-2-[[6-fluoro-5-[2-methyl-1-oxido-4-(trifluoromethyl)pyridin-1-ium-3-yl]-2-pyridyl]amino]-2-oxo-ethyl]-2-isopropyl-pyrazole-3-carboxamide;

Atropisomer 1 of N-[(1S)-1-[[6-chloro-5-(2,4-dimethyl-1-oxido-pyridin-1-ium-3-yl)-2-pyridyl]carbamoyl]-2,2-dicyclopropyl-ethyl]-2-isopropyl-pyrazole-3-carboxamide;

Atropisomer 2 of N-[(1S)-1-[[6-chloro-5-(2,4-dimethyl-1-oxido-pyridin-1-ium-3-yl)-2-pyridyl]carbamoyl]-2,2-dicyclopropyl-ethyl]-2-isopropyl-pyrazole-3-carboxamide;

N-[(1S)-1-(dicyclopropylmethyl)-2-[[6-fluoro-5-(2-methyl-5-methylsulfonyl-1-oxido-pyridin-1-ium-3-yl)-2-pyridyl]amino]-2-oxo-ethyl]-2-isopropyl-pyrazole-3-carboxamide;

N-[(1S)-1-[[5-(5-cyano-2-methyl-1-oxido-pyridin-1-ium-3-yl)-6-fluoro-2-pyridyl]carbamoyl]-2,2-dicyclopropyl-ethyl]-2-isopropyl-pyrazole-3-carboxamide; and N-[(1S)-1-(dicyclopropylmethyl)-2-[[6-fluoro-5-(5-methoxy-2-ethyl-1-oxido-pyridin-1-ium-3-yl)-2-pyridyl]amino]-2-oxo-ethyl]-2-isopropyl-pyrazole-3-carboxamide;

or pharmaceutically acceptable salts thereof.

14. A compound selected from N-[(1S)-1-(dicyclopropylmethyl)-2-[[6-fluoro-5-(5-methoxy-2-methyl-1-oxido-pyridin-1-ium-3-yl)-2-pyridyl]amino]-2-oxo-ethyl]-2-isopropyl-pyrazole-3-carboxamide and a pharmaceutically acceptable salt thereof.

15. A method for treating an IL-17 mediated disease, disorder, or condition comprising administering to a patient in need thereof an effective amount of at least one compound according to claim 1, wherein the disease, disorder or condition is selected from inflammatory bowel disease, rheumatoid arthritis, psoriasis, plaque psoriasis, pustular psoriasis, and psoriatic arthritis.

16. The method according to claim 15, wherein the disease, disorder or condition is selected from psoriasis, psoriatic arthritis, plaque psoriasis, and pustular psoriasis.

17. The method according to claim 15, wherein the disease, disorder, or condition is an autoimmune disease.

18. The method according to claim 15, wherein the disease, disorder, or condition is psoriasis.

19. A pharmaceutical composition comprising a compound according to claim 1 and at least one additive, wherein the at least one additive is selected from pharmaceutically acceptable vehicles, excipients, and pharmaceutically acceptable carriers.

20. The pharmaceutical composition according to claim 19, wherein the pharmaceutical composition further comprises at least one therapeutically active compound.

* * * * *